(12) United States Patent
Li et al.

(10) Patent No.: US 12,060,617 B2
(45) Date of Patent: *Aug. 13, 2024

(54) MARKER GENES FOR PROSTATE CANCER CLASSIFICATION

(71) Applicant: PROSTATYPE GENOMICS AB, Stockholm (SE)

(72) Inventors: Chunde Li, Södertälje (SE); Zhuochun Peng, Solna (SE); Lambert Skoog, Stockholm (SE)

(73) Assignee: PROSTATYPE GENOMICS AB, Stockholm (SE)

( * ) Notice: Subject to any disclaimer, the term of this patent is extended or adjusted under 35 U.S.C. 154(b) by 626 days.

This patent is subject to a terminal disclaimer.

(21) Appl. No.: 16/904,789

(22) Filed: Jun. 18, 2020

(65) Prior Publication Data

US 2021/0017606 A1   Jan. 21, 2021

Related U.S. Application Data

(63) Continuation of application No. 15/725,678, filed on Oct. 5, 2017, now abandoned, which is a continuation of application No. 14/352,107, filed as application No. PCT/EP2012/071077 on Oct. 24, 2012, now Pat. No. 9,790,555.

(30) Foreign Application Priority Data

Oct. 24, 2011 (SE) .................................. 1150982-5

(51) Int. Cl.
  *C12Q 1/68*   (2018.01)
  *C12Q 1/6886* (2018.01)
  *G01N 33/574* (2006.01)

(52) U.S. Cl.
  CPC ..... *C12Q 1/6886* (2013.01); *G01N 33/57434* (2013.01); *C12Q 2600/118* (2013.01); *C12Q 2600/158* (2013.01)

(58) Field of Classification Search
  None
  See application file for complete search history.

(56) References Cited

U.S. PATENT DOCUMENTS

| | | | |
|---|---|---|---|
| 9,790,555 B2 * | 10/2017 | Li | .................... G01N 33/57434 |
| 2001/0053519 A1 | 12/2001 | Fodor et al. | |
| 2002/0038464 A1 | 3/2002 | Charron et al. | |
| 2003/0054419 A1 | 3/2003 | Slawin et al. | |
| 2009/0298082 A1 | 12/2009 | Klee et al. | |
| 2010/0056445 A1 | 3/2010 | Sharma et al. | |
| 2010/0233691 A1 | 9/2010 | Bankaitis-Davis et al. | |
| 2011/0166030 A1 | 7/2011 | Wang et al. | |
| 2018/0080088 A1 | 3/2018 | Li et al. | |

FOREIGN PATENT DOCUMENTS

| | | | |
|---|---|---|---|
| JP | 2011-517283 A | 6/2011 | |
| NO | WO2009/021338 A1 | 2/2009 | |
| WO | WO2001/071355 A2 | 9/2001 | |
| WO | WO2006/028867 A2 | 3/2006 | |
| WO | WO2006/135886 A2 | 12/2006 | |
| WO | WO2008/013492 A1 | 1/2008 | |
| WO | WO-2008013492 A1 * | 1/2008 | ........... C12Q 1/6886 |
| WO | WO2008/079269 A2 | 7/2008 | |
| WO | WO2009/105154 A2 | 8/2009 | |
| WO | WO2009/108860 A2 | 9/2009 | |
| WO | WO2009/143603 A1 | 12/2009 | |
| WO | WO2010/006048 A2 | 1/2010 | |
| WO | WO2010/101888 A2 | 9/2010 | |
| WO | WO2013/060739 A1 | 5/2013 | |

OTHER PUBLICATIONS

Prueitt et al. (Prostate 68:1152-1164, 2008) (Year: 2008).*
Blumke et al. (The Journal of Urology, vol. 175, No. 4, Supplement, Sunday May 21, 2006, Abstract #249, p. 83) (Year: 2006).*
Keys et al. Chapter 6 in Sridar V. Chittur (ed.), Microarray Methods for Drug Discovery, Methods in Molecular Biology, vol. 632, DOI 10.1007/978-1-60761-663-4_6, © Humana Press, a part of Springer Science+Business Media, LLC 2010. (Year: 2010).*
NCBI Geo record GSE7055. Obtained from Geo Gene Expression Omnibus database. 2 pages. (Year: 2008).*
Definition of Tumor. NCI dictionary of cancer terms. https://www.cancer.gov/publications/dictionaries/cancer-terms/def/tumor Accessed Jun. 19, 2023. one page. (Year: 2023).*
Agilent-014850 Whole Genome Microarray, 4X44K, as disclosed in NCBI Platform GPL4133 (2006).
Akashi, T. et al: "Tissue factor expression and prognosis in patients with metastatic prostate cancer". Uroloov. (2003) 62(6):1078-1082.
Chandran, U., et al. (2007), "Gene expression profiles of prostate cancer reveal involvement of multiple molecular pathways in the metastatic process", BMC Cancer, 7(64): 21 pages.
Flaig, T., et at. (2007), "Conference Report and Review: Current Status of Biomarkers Potentially Associated With Prostate Cancer Outcomes", The Journal of Uroloov, 177: 1229- 1237.

(Continued)

*Primary Examiner* — Juliet C Switzer
(74) *Attorney, Agent, or Firm* — Cermak & McGowan LLP; Malcolm K. McGowan

(57) ABSTRACT

The present invention relates to a method for classifying a prostate cancer in a subject, the method comprising the steps of a) determining a gene expression level or gene expression pattern of the genes F3 and IGFBP3 in a sample from the subject and b) classifying the tumor by comparing the gene expression level determined in a) with a reference gene expression of the same genes in reference patients known to have a high risk tumor respectively. In addition the invention relates to a method for determining prognosis of a subject diagnosed with prostate cancer, a method for making a treatment decision for a subject diagnosed with prostate cancer and a solid support or a kit for classifying a tumor in a subject diagnosed with prostate cancer.

7 Claims, 29 Drawing Sheets
Specification includes a Sequence Listing.

(56) References Cited

OTHER PUBLICATIONS

Iscove et al. Representation is faithfully preserved in global cDNA amplified exponentially from sub-picogram quantities of mRNA, Nature Biotechnology, (2002), p. 940-943.
Jing, M., et al. (2009), "Prediagnostic plasma levels of insulin-like growth factor (IGF)-1, IGF-binding protein (IGFBP)-3, and C-peptide predict long-term prostate cancer survival in men without apparent prostate cancer at baseline", Proceedings of the American Association for Cancer Research, Epidemioloov 9, 50: 733.
Kurashige, Y., et al. (2008), "Profiling of differentially expressed genes in procine epithelial cells derived from periodontal ligament and gingiva by DNA microarray", Archives of Oral Biology, 53: 437-442.
Lapointe, J., et al. (2004), "Gene expression profiling identifies clinically relevant subtypes of prostate cancer", PNAS, 101(3): 811-816.
Mehta, H et al: "OR6,34 IGFBP-3 is a metastasis suppression gene for prostate cancer". Growth Hormone and IGF Research (2010) 20: S15.
Nakagawa, et al: A Tissue Biomarker Panel Predicting Systemic Progression after PSA Recurrence Post-Definitive Prostate Cancer Therapy II. Plos One. (2008).vol. 3(5): e2318.
NEB catalog (1998/1999), pp. 121, 284.
Papadimitrakopoulou, V., et al. (2006), "The prognostic role of loss of insulin-like growth factorbinding protein-3 expression in head and neck carcinogenesis", Cancer Letters, 239: 136-143.
Pradervand, S., et al. (2008), "Affymetrix Whole-Transcript Human Gene 1.0 ST array is highly concordant with standard 3' expression arrays", BioTechniques, 44(6): 759-762.
Strijbos, M.H. et al: "Circulating endothelial cells, circulating tumour cells, tissue factor, endothelin-1 and overall survival in prostate cancer patients treated with docetaxel". European Journal of Cancer. (2010) 46(11): 2027-2035.
International Search Report and Written Opinion mailed on Oct. 1, 2013 by the International Searching Authority for International Patent Application No. PCT/EP2012/071077, which was filed on Oct. 24, 2012 and published as WO 2013/060739 on May 2, 2013 (Applicant—Chundsell Medicals AB) (11 pages).
International Preliminary Report on Patentability issued on Apr. 29, 2014 by the International Searching Authority for International Patent Application No. PCT/EP2012/071077, which was filed on Oct. 24, 2012 and published as WO 2013/060739 on May 2, 2013 (Applicant—Chundsell Medicals AB) (7 pages).
Preliminary Amendment mailed on Apr. 16, 2014 by the USPTO for U.S. Appl. No. 14/352,107, which was filed on Apr. 16, 2014 and granted as U.S. Pat. No. 9,790,555 on Oct. 17, 2017 (Inventor—Chunde Li, et al.) (10 pages).
Restriction Requirement issued on Aug. 18, 2016 by the USPTO for U.S. Appl. No. 14/352,107, which was filed on Apr. 16, 2014 and granted as U.S. Pat. No. 9,790,555 on Oct. 17, 2017 (Inventor—Chunde Li, et al.) (9 pages).
Response to Restriction Requirement mailed on Oct. 11, 2016 by the USPTO for U.S. Appl. No. 14/352,107, which was filed on Apr. 16, 2014 and granted as U.S. Pat. No. 9,790,555 on Oct. 17, 2017 (Inventor—Chunde Li, et al.) (7 pages).
Non Final Rejection issued on Jan. 20, 2017 by the USPTO for U.S. Appl. No. 14/352,107, which was filed on Apr. 16, 2014 and granted as U.S. Pat. No. 9,790,555 on Oct. 17, 2017 (Inventor—Chunde Li, et al.) (14 pages).
Response to Non Final Rejection mailed on May 23, 2017 by the USPTO for U.S. Appl. No. 14/352,107, which was filed on Apr. 16, 2014 and granted as U.S. Pat. No. 9,790,555 on Oct. 17, 2017 (Inventor—Chunde Li, et al.) (12 pages).
Notice of Allowance issued on Jun. 9, 2017 by the USPTO for U.S. Appl. No. 14/352,107, which was filed on Apr. 16, 2014 and granted as U.S. Pat. No. 9,790,555 on Oct. 17, 2017 (Inventor—Chunde Li, et al.) (9 pages).
Notice of Allowance issued on Jun. 28, 2017 by the USPTO for U.S. Appl. No. 14/352,107, which was filed on Apr. 16, 2014 and granted as U.S. Pat. No. 9,790,555 on Oct. 17, 2017 (Inventor—Chunde Li, et al.) (2 pages).
Amendment/Req. Reconsideration—After NonFinal Reject issued on Aug. 28, 2017 by the USPTO for U.S. Appl. No. 14/352,107, which was filed on Apr. 16, 2014 and granted as U.S. Pat. No. 9,790,555 on Oct. 17, 2017 (Inventor—Chunde Li, et al.) (4 pages).
Issue Notification issued on Sep. 27, 2017 by the USPTO for U.S. Appl. No. 14/352,107, which was filed on Apr. 16, 2014 and granted as U.S. Pat. No. 9,790,555 on Oct. 17, 2017 (Inventor—Chunde Li, et al.) (1 paqe).
VanGuilder et al. Biotechniques 44:619-626 (Year: 2008).
Shariat et al., Journal of Clinical Oncology, vol. 20, No. 3, Feb. 1, 2002: pp. 833-841.
Strijbos et al., European Journal of Cancer 2010;46(1):2027-2035.
Kaushal et al., Appl. Immunohistochem. Mol. Morphol., vol. 16, No. 1, Jan. 2008, pp. 1-6.
Ohta et al., Anticancer Research 2002;22:2991-2996.
Nakagawa et al., "A Tissue Biomarker Panel Predicting Systemic Progression after PSA Recurrence Post-Definitive Prostate Cancer Therapy," PLoS ONE 2008;3(5): e2318. doi: 10.1371/journal.pone. 0002318.
Thangaiah et al., N A J Med. Sci. 2014;7(2):75-80.

* cited by examiner

| Gene variable | Overall survival | | | | Cancer survival | | | |
|---|---|---|---|---|---|---|---|---|
| | PSA(ng/ml) | Tumor WHO Grade Poorly vs. | Clinical Stage* Advanced vs. | Age † | PSA(ng/ml) | Tumor WHO Grade Poorly vs. | Clinical Stage* Advanced vs. | Age † |
| F3 | ● | ●⁻ | ●⁻ | ● | ● | ●⁻ | ●⁻ | ● |
| IGFBP3 | ● | ● | ●⁻ | ●⁻ | ● | ● | ● | ○⁻ |
| CTGF | ● | ● | ● | ● | ● | ● | ● | ●⁻ |
| AMACR | □ | ○ | □ | ○ | ● | ● | ● | ●⁻ |
| WNT5B | ○ | ●⁻ | ○⁻ | ● | ● | ● | ● | □ |
| EZH2 | ● | □ | ●⁻ | ● | ● | ● | ● | □ |
| C-MAF-a | ○ | □ | □ | ○ | □ | □ | ○ | □ |
| VGLL3 | □ | □ | □ | □ | ⊡ | □ | ○ | □ |
| MUC1 | □ | □ | □ | □ | ⊡ | □ | □ | □ |
| C-MAF-b | ○ | ○ | ○ | □ | | | | |

●¹ Clinical variable is dependent on gene variable.

● Gene variable is independent on clinical variable, gene variable shows higher hazards than clinical variable.

○ Gene variable is independent on clinical variable, clinical variable shows higher hazards than gene variable.

○ Gene variable is dependent on clinical variable.

□ The relation between gene variable with clinical variable is unknown.

\* Clinical stage groups were classified using Tumor-Node-Metastasis (TNM) system and PSA value. Advanced clinical stage was defined as TNM stage any of T≥3, N1, M1 or PSA > 100.0 ng/mL. Localized clinical stage was defined as T1-2N0M0 and PSA≤100.0 ng/mL.

† Age was modeled as a continuous variable. The hazard ratio is for each 1.0 year increase in age.

FIG. 4A

Cox proportional hazards analysis of each ESCGP and clinical parameters (Univariate and Multivariate Analysis).

B. F3

| Variable | No. of Samples* | Overall Survival | | | | Cancer Survival | | | |
|---|---|---|---|---|---|---|---|---|---|
| | | Univariate analysis | | Multivariate Analysis | | Univariate analysis | | Multivariate Analysis | |
| | | Hazard Ratio (95% CI) | P value | Hazard Ratio (95% CI) | P value | Hazard Ratio (95% CI) | P value | Hazard Ratio (95% CI) | P value |
| F3 † | 87 | 1.11 (1.05-1.18) | <0.001 | 1.11 (1.04-1.18) | 0.001 | 1.13 (1.05-1.22) | 0.001 | 1.14 (1.06-1.24) | 0.001 |
| PSA>50 vs. PSA≤50 (ng/ml) | 87 | 2.93 (1.76-4.88) | <0.001 | 1.76 (0.97-3.19) | 0.06 | 3.33 (1.73-6.41) | <0.001 | 1.54 (0.71-3.37) | 0.28 |
| Tumor WHO Grade Poorly vs. Moderated / Well | 87 | 1.65 (1.03-2.66) | 0.04 | 1.30 (0.78-2.16) | 0.32 | 1.93 (1.04-3.57) | 0.04 | 1.35 (0.70-2.63) | 0.37 |
| Clinical Stage ‡ Advanced vs. Localized | 87 | 2.13 (1.32-3.45) | 0.002 | 2.02 (1.14-3.59) | 0.02 | 3.87 (1.94-7.70) | <0.001 | 4.19 (1.89-9.28) | <0.001 |
| Age § | 87 | 1.06 (1.03-1.09) | <0.001 | 1.05 (1.01-1.08) | 0.004 | 1.08 (1.02-1.10) | 0.003 | 1.04 (1.00-1.09) | 0.03 |

FIG. 4B

C. IGFBP3

| Variable | No. of Samples* | Overall Survival | | | | Cancer Survival | | | |
|---|---|---|---|---|---|---|---|---|---|
| | | Univariate analysis | | Multivariate Analysis | | Univariate analysis | | Multivariate Analysis | |
| | | Hazard Ratio (95% CI) | P value | Hazard Ratio (95% CI) | P value | Hazard Ratio (95% CI) | P value | Hazard Ratio (95% CI) | P value |
| IGFBP3 † | 148 | 1.11 (1.04-1.18) | 0.002 | 1.09 (1.02-1.17) | 0.01 | 1.16 (1.07-1.26) | <0.001 | 1.16 (1.06-1.26) | 0.001 |
| PSA>50 vs. PSA≤50 (ng/ml) | 148 | 2.14 (1.50-3.07) | <0.001 | 1.65 (1.09-2.48) | 0.006 | 2.48 (1.58-3.91) | <0.001 | 1.97 (1.17-3.31) | 0.01 |
| Tumor WHO Grade Poorly vs. Moderated / Well | 148 | 1.53 (1.08-2.19) | 0.02 | 1.17 (0.80-1.71) | 0.42 | 1.89 (1.08-2.64) | 0.02 | 1.24 (0.77-1.98) | 0.37 |
| Clinical Stage ‡ Advanced vs. Localized | 148 | 1.71 (1.20-2.44) | 0.003 | 1.34 (0.90-2.00) | 0.15 | 2.25 (1.42-3.55) | 0.001 | 1.65 (0.99-2.76) | 0.06 |
| Age § | 148 | 1.04 (1.02-1.06) | <0.001 | 1.03 (1.00-1.05) | 0.02 | 1.03 (1.00-1.05) | 0.051 | 1.01 (0.98-1.03) | 0.71 |

FIG. 4C

D. CTGF

| Variable | No. of Samples* | Overall Survival | | | | | Cancer Survival | | | |
|---|---|---|---|---|---|---|---|---|---|---|
| | | Univariate Analysis Hazard Ratio (95% CI) | P value | Multivariate Analysis Hazard Ratio (95% CI) | P value | | Univariate analysis Hazard Ratio (95% CI) | P value | Multivariate Analysis Hazard Ratio (95% CI) | P |
| CTGF † | 91 | 1.12 (1.02-1.23) | 0.02 | 1.12 (1.01-1.24) | 0.03 | | 1.15 (1.02-1.30) | 0.02 | 1.16 (1.02-1.32) | 0.03 |
| PSA>50 vs. PSA≤50 (ng/ml) | 91 | 2.85 (1.74-4.69) | <0.001 | 2.08 (1.14-3.81) | 0.02 | | 3.28 (1.72-6.26) | <0.001 | 1.80 (0.81-4.04) | 0.15 |
| Tumor WHO Grade | | | | | | | | | | |
| Poorly vs. Moderated / Well | 91 | 1.74 (1.09-2.78) | 0.02 | 1.49 (0.90-2.45) | 0.12 | | 1.99 (1.08-3.66) | 0.03 | 1.48 (0.77-2.85) | 0.25 |
| Clinical Stage ‡ | | | | | | | | | | |
| Advanced vs. Localized | 91 | 2.19 (1.36-3.51) | 0.001 | 1.59 (0.90-2.79) | 0.11 | | 4.03 (2.03-8.01) | <0.001 | 3.23 (1.46-7.13) | 0.004 |
| Age § | 91 | 1.06 (1.03-1.09) | <0.001 | 1.04 (1.01-1.07) | 0.01 | | 1.05 (1.02-1.09) | 0.004 | 1.04 (1.00-1.08) | 0.07 |

FIG. 4D

E. AMACR

| Variable | No. of Samples* | Overall Survival | | | | | Cancer Survival | | | |
|---|---|---|---|---|---|---|---|---|---|---|
| | | Univariate Analysis Hazard Ratio (95% CI) | P value | Multivariate Analysis Hazard Ratio (95% CI) | P value | | Univariate Analysis Hazard Ratio (95% CI) | P value | Multivariate Analysis Hazard Ratio (95% CI) | P value |
| AMACR † | 129 | 1.10 (1.03-1.17) | 0.005 | 1.09 (1.02-1.17) | 0.01 | | 1.09 (1.00-1.18) | 0.04 | 1.09 (1.01-1.19) | 0.04 |
| PSA>50 vs. PSA≤50 (ng/ml) | 129 | 1.85 (1.26-2.70) | 0.002 | 1.58 (1.02-2.43) | 0.04 | | 2.06 (1.29-3.30) | 0.002 | 1.82 (1.06-3.10) | 0.03 |
| Tumor WHO Grade | | | | | | | | | | |
| Poorly vs. Moderated / Well | 129 | 1.40 (0.95-2.06) | 0.09 | 1.11 (0.74-1.66) | 0.61 | | 1.74 (1.06-2.83) | 0.03 | 1.40 (0.84-2.32) | 0.19 |
| Clinical Stage ‡ | | | | | | | | | | |
| Advanced vs. Localized | 129 | 1.76 (1.19-2.58) | 0.004 | 1.40 (0.92-2.13) | 0.12 | | 2.26 (1.38-3.71) | 0.001 | 1.72 (1.01-2.94) | 0.05 |
| Age § | 129 | 1.04 (1.02-1.06) | 0.001 | 1.02 (1.00-1.04) | 0.11 | | 1.02 (1.00-1.05) | 0.11 | 1.00 (0.97-1.03) | 0.89 |

FIG. 4E

F. WNT5B

| Variable | No. of Samples* | Overall Survival | | | | | Cancer Survival | | | |
|---|---|---|---|---|---|---|---|---|---|---|
| | | Univariate Analysis | | Multivariate Analysis | | | Univariate Analysis | | Multivariate Analysis | |
| | | Hazard Ratio (95% CI) | P value | Hazard Ratio (95% CI) | P value | | Hazard Ratio (95% CI) | P value | Hazard Ratio (95% CI) | P value |
| WNT5B † | 81 | 1.13 (1.03-1.24) | 0.01 | 1.07 (0.97-1.17) | 0.18 | | 1.23 (1.09-1.39) | 0.001 | 1.16 (1.03-1.31) | 0.01 |
| PSA>50 vs. PSA≤50 (ng/ml) | 81 | 2.41 (1.45-4.02) | 0.001 | 1.77 (0.98-3.18) | 0.06 | | 2.81 (1.43-5.51) | 0.003 | 1.56 (0.72-3.37) | 0.25 |
| Tumor WHO Grade | | | | | | | | | | |
| Poorly vs. Moderated / Well | 81 | 1.94 (1.19-3.15) | 0.008 | 1.77 (1.05-2.99) | 0.03 | | 2.10 (1.11-3.96) | 0.02 | 1.74 (0.87-3.45) | 0.12 |
| Clinical Stage ‡ | | | | | | | | | | |
| Advanced vs. Localized | 81 | 1.98 (1.21-3.21) | 0.006 | 1.49 (0.86-2.60) | 0.16 | | 3.87 (1.88-7.95) | 0.000 | 3.16 (1.44-6.97) | 0.004 |
| Age § | 81 | 1.05 (1.02-1.08) | 0.001 | 1.03 (1.00-1.06) | 0.04 | | 1.04 (1.01-1.08) | 0.02 | 1.02 (0.98-1.06) | 0.32 |

FIG. 4F

G. EZH2

| Variable | No. of samples* | Overall Survival | | | | | Cancer Survival | | | |
|---|---|---|---|---|---|---|---|---|---|---|
| | | Univariate analysis | | Multivariate Analysis | | | Univariate analysis | | Multivariate Analysis | |
| | | Hazard Ratio (95% CI) | P Value | Hazard Ratio (95% CI) | P Value | | Hazard Ratio (95% CI) | P Value | Hazard Ratio (95% CI) | P Value |
| EZH2 † | 126 | 0.93 (0.83-1.04) | 0.22 | 0.95 (0.85-1.06) | 0.33 | | 0.84 (0.74-0.97) | 0.02 | 0.87 (0.76-0.99) | 0.04 |
| PSA>50 vs. PSA≤50 (ng/ml) | 126 | 1.79 (1.22-2.63) | 0.003 | 1.29 (0.84-1.99) | 0.24 | | 2.07 (1.29-3.32) | 0.003 | 1.56 (0.92-2.66) | 0.10 |
| Tumor WHO Grade | | | | | | | | | | |
| Poorly vs. Moderated / Well | 126 | 1.40 (0.94-2.07) | 0.01 | 1.10 (0.73-1.67) | 0.65 | | 1.70 (1.03-2.79) | 0.04 | 1.38 (0.81-2.30) | 0.25 |
| Clinical Stage ‡ | | | | | | | | | | |
| Advanced vs. Localized | 126 | 1.84 (1.24-2.73) | 0.003 | 1.51 (0.98-2.34) | 0.06 | | 2.33 (1.41-3.86) | 0.001 | 1.76 (1.01-3.06) | 0.05 |
| Age § | 126 | 1.04 (1.02-1.06) | 0.001 | 1.03 (1.01-1.06) | 0.01 | | 1.02 (1.00-1.05) | 0.09 | 1.01 (0.98-1.04) | 0.61 |

FIG. 4G

H. c-MAF-a

| Variable | No. of Samples* | Overall Survival | | | | | Cancer Survival | | | |
|---|---|---|---|---|---|---|---|---|---|---|
| | | Univariate analysis | | Multivariate Analysis | | | Univariate analysis | | Multivariate Analysis | |
| | | Hazard Ratio (95% CI) | P value | Hazard Ratio (95% CI) | P value | | Hazard Ratio (95% CI) | P value | Hazard Ratio (95% CI) | P value |
| c-MAF-a † | 152 | 1.10 (1.03-1.18) | 0.007 | 1.08 (1.00-1.16) | 0.04 | | 1.11 (1.01-1.21) | 0.03 | 1.09 (1.00-1.20) | 0.05 |
| PSA>50 vs. PSA≤50 (ng/ml) | 152 | 2.20 (1.54-3.13) | <0.001 | 1.75 (1.17-2.63) | 0.007 | | 2.45 (1.57-3.83) | <0.001 | 1.99 (1.20-3.33) | 0.008 |
| Tumor WHO Grade | | | | | | | | | | |
| Poorly vs. Moderated / Well | 152 | 1.53 (1.08-2.17) | 0.02 | 1.19 (0.82-1.72) | 0.37 | | 1.70 (1.08-2.63) | 0.02 | 1.28 (0.80-2.04) | 0.30 |
| Clinical Stage ‡ | | | | | | | | | | |
| Advanced vs. Localized | 152 | 1.65 (1.17-2.33) | 0.005 | 1.26 (0.86-1.87) | 0.24 | | 2.14 (1.37-3.35) | 0.001 | 1.58 (0.96-2.60) | 0.07 |
| Age § | 152 | 1.04 (1.02-1.06) | <0.001 | 1.02 (1.00-1.05) | 0.03 | | 1.02 (1.00-1.05) | 0.06 | 1.00 (0.98-1.03) | 0.77 |

FIG. 4H

I. VGLL3

| Variable | No. of Samples* | Overall Survival | | | | | Cancer Survival | | | |
|---|---|---|---|---|---|---|---|---|---|---|
| | | Univariate Analysis | | Multivariate Analysis | | | Univariate Analysis | | Multivariate Analysis | |
| | | Hazard Ratio (95% CI) | P value | Hazard Ratio (95% CI) | P value | | Hazard Ratio (95% CI) | P value | Hazard Ratio (95% CI) | P value |
| VGLL3 † | 135 | 1.07 (1.02-1.13) | 0.009 | 1.05 (0.99-1.11) | 0.01 | | 1.06 (0.99-1.13) | 0.09 | 1.04 (0.97-1.11) | 0.30 |
| PSA>50 vs. PSA≤50 (ng/ml) | 135 | 2.26 (1.53-3.33) | <0.001 | 1.79 (1.16-2.77) | 0.009 | | 2.44 (1.50-3.95) | <0.001 | 1.91 (1.11-3.29) | 0.02 |
| Tumor WHO Grade | | | | | | | | | | |
| Poorly vs. Moderated / Well | 135 | 1.62 (1.11-2.35) | 0.01 | 1.17 (0.77-1.78) | 0.45 | | 1.94 (1.20-3.15) | 0.007 | 1.48 (0.88-2.50) | 0.14 |
| Clinical Stage ‡ | | | | | | | | | | |
| Advanced vs. Localized | 135 | 1.81 (1.25-2.62) | 0.002 | 1.46 (0.96-2.20) | 0.07 | | 2.42 (1.49-3.92) | <0.001 | 1.82 (1.08-3.09) | 0.03 |
| Age § | 135 | 1.04 (1.02-1.07) | <0.001 | 1.03 (1.00-1.05) | 0.02 | | 1.03 (1.00-1.05) | 0.04 | 1.01 (0.98-1.04) | 0.52 |

FIG. 4I

J. MUC1

| Variable | No. of Samples* | Univariate Analysis Hazard Ratio (95% CI) | P value | Overall Survival Multivariate Analysis Hazard (95% CI) | P value | Univariate Analysis Hazard Ratio (95% CI) | P value | Cancer Survival Multivariate Analysis Hazard Ratio (95% CI) | P value |
|---|---|---|---|---|---|---|---|---|---|
| MUC1 † | 125 | 1.08 (1.02-1.16) | 0.01 | 1.06 (0.99-1.14) | 0.08 | 1.08 (1.00-1.17) | 0.06 | 1.05 (0.98-1.14) | 0.27 |
| PSA>50 vs. PSA≤50 (ng/ml) | 125 | 1.77 (1.20-2.60) | 0.004 | 1.16 (0.74-1.81) | 0.51 | 2.03 (1.26-3.27) | 0.004 | 1.43 (0.82-2.49) | 0.20 |
| Tumor WHO Grade | | | | | | | | | |
| Poorly vs. Moderated / Well | 125 | 1.42 (0.96-2.11) | 0.08 | 1.13 (0.74-1.72) | 0.57 | 1.77 (1.07-2.92) | 0.03 | 1.46 (0.86-2.46) | 0.16 |
| Clinical Stage ‡ | | | | | | | | | |
| Advanced vs. Localized | 125 | 1.82 (1.23-2.71) | 0.003 | 1.55 (1.00-2.40) | 0.05 | 2.30 (1.39-3.82) | 0.001 | 1.77 (1.02-3.08) | 0.04 |
| Age § | 125 | 1.04 (1.02-1.06) | 0.001 | 1.03 (1.01-1.06) | 0.01 | 1.02 (1.00-1.05) | 0.09 | 1.01 (0.98-1.04) | 0.54 |

FIG. 4J

K. c-MAF-b

| Variable | No. of Samples* | Univariate Analysis Hazard Ratio (95% CI) | P value | Overall Survival Multivariate Analysis Hazard (95% CI) | P value | Univariate Analysis Hazard Ratio (95% CI) | P value | Cancer Survival Multivariate Analysis Hazard Ratio (95% CI) | P value |
|---|---|---|---|---|---|---|---|---|---|
| c-MAF-b † | 66 | 1.09 (0.92-1.28) | 0.32 | 1.02 (0.86-1.21) | 0.85 | 1.24 (1.00-1.53) | 0.05 | 1.12 (0.91-1.39) | 0.29 |
| PSA>50 vs. PSA≤50 (ng/ml) | 66 | 2.43 (1.40-4.22) | 0.002 | 2.22 (1.20-4.09) | 0.01 | 2.45 (1.21-4.97) | 0.01 | 1.88 (0.83-4.29) | 0.13 |
| Tumor WHO Grade | | | | | | | | | |
| Poorly vs. Moderated / Well | 66 | 2.03 (1.19-3.49) | 0.010 | 1.95 (1.04-3.65) | 0.04 | 2.22 (1.11-4.49) | 0.02 | 1.50 (0.68-3.33) | 0.31 |
| Clinical Stage ‡ | | | | | | | | | |
| Advanced vs. Localized | 66 | 1.58 (0.93-2.67) | 0.09 | 1.06 (0.55-2.02) | 0.87 | 3.01 (1.41-6.42) | 0.004 | 2.16 (0.89-5.24) | 0.09 |
| Age § | 66 | 1.04 (1.01-1.07) | 0.007 | 1.03 (1.00-1.06) | 0.08 | 1.03 (0.99-1.07) | 0.09 | 1.02 (0.98-1.06) | 0.35 |

* Each ESCGP has its own number of samples due to not all of ESCGPs having been profiled across all samples. Univariate and Multivariate analysis have been performed across the same bunch of samples.

† Centered delta Ct value of gene was modeled as continuous variable. It is reversely corresponding to gene's expression level. The hazard ratio is for each increase of 1.0 unit in centered delta Ct value of gene.

‡ Clinical stage groups were classified using Tumor-Node-Metastasis (TNM) system and PSA value. Advanced clinical stage was defined as TNM stage any of T≥3, N1, M1 or PSA > 100.0 ng/ml. Localized clinical stage was defined as T1-2N0M0 and PSA≤100.0 ng/ml.

§ Age was modeled as a continuous variable. The hazard ratio is for each 1.0 year increase in age.

FIG. 4K

Kaplan-Meier survival curves of the three tumor subtypes classified by ESCGP signature 1 in patients primarily treated only by castration therapy.

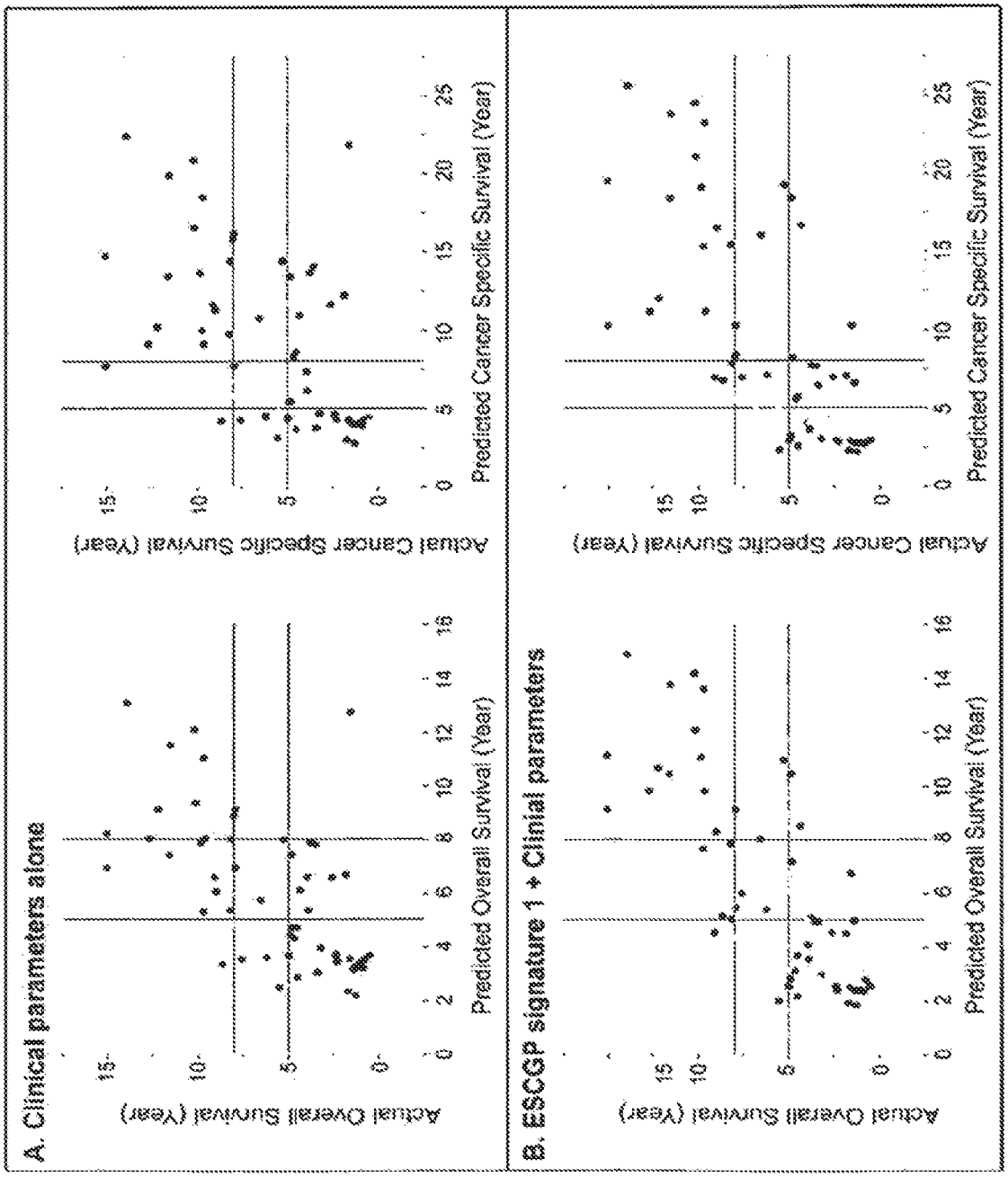

Prediction accuracy of two parametric models

| | Prediction Accuracy (%)* | | | |
|---|---|---|---|---|
| | Overall Survival | | Cancer Survival | |
| | 5 years | 8 years | 5 years | 8 years |
| Clinical parameters alone † | 70.1 | 79.3 | 65.5 | 74.7 |
| ESCGP signature 1 + Clinical parameters ‡ | 78.2 | 78.2 | 71.3 | 77.0 |

* Prediction accuracy was calculated by an equation: prediction accuracy (%) = (No of samples-No of unmatched samples)/No of samples, of the equation, No of unmatched samples presented as points in panel A and B are the points located in squals with actual survival> 5, 8 yrs and predicted survivals 5, 8 yrs, or actual survivals 5,8 yrs and predicted survival> 5, 8 yrs.
† Clinical parameters include Age (continuous variable), PSA (>50 ng/ul vs. ≤50ng/ul), tumor WHO grade (Advanced vs. Localized) and clinical stage (Poorly vs. Moderate/Well).
‡ ESCGP signature 1 is categorical variable included three categories (three tumor subtypes, Group 1, Group 2 and Group 3, classified by combined gene signature of VGLL3, IGFBP3 and F3). 87 patients have the complete clinical data and profiled ESCGP signature 1.

FIG. 12C

D. Contribution of ESCGP signature 1 and clinical parameters in multivariate survival analysis

| | Overall Survival | | Cancer Survival | |
|---|---|---|---|---|
| | Likelihood Ratio (LR)* | LR contribution † | Likelihood Ratio (LR)* | LR contribution † |
| Clinical parameters alone ‡ | 34.24 (P<0.001) | 21.60 (P<0.001) | 32.02 (P<0.001) | 25.90 (P<0.001) |
| ESCGP signature 1 alone § | 29.17 (P<0.001) | 18.53 (P<0.001) | 22.55 (P<0.001) | 16.43 (P<0.001) |
| ESCGP signature 1 + Clinical parameters | 52.77 (P<0.001) | - | 48.45 (P<0.001) | - |

\* Likelihood Ratio (LR) value shows degree of likelihood in Cox regression model. P value shows the significance of model.
† LR contribution derived from LR nest test. LR nest test shows difference of Likelihood ratio value between two cox regression models with assumption that one model was nested in another model, the test is chi-square distributed. LR contribution indicates the contribution of variable in ESCGP signature 1 together with clinical parameters multivariate model. P value indicates the significance of contribution.
‡ Clinical parameters include Age (continuous variable), PSA (>50 ng/ul vs. ≤50ng/ul), tumor WHO grade (Advanced vs. Localized) and clinical stage (Poorly vs. Moderate/Well).
§ ESCGP signature 1 is categorical variable included three categories (three tumor subtypes, Group 1, Group 2 and Group 3, classified by combined gene signature of VGLL3, IGFBP3 and F3). 87 patients have the complete clinical data and profiled ESCGP signature 1.

FIG. 12D

SEQUENCE LISTING

```
<160> NUMBER OF SEQ ID NOS: 68

<210> SEQ ID NO 1
<211> LENGTH: 2620
<212> TYPE: DNA
<213> ORGANISM: Homo sapiens

<400> SEQUENCE: 1
agatgcgagc actgcggctg ggcgctgagg atcagccgct tcctgcctgg attccacagc      60
ttcgcgccgt gtactgtcgc cccatccctg cgcgcccagc ctgccaagca gcgtgccccg     120
gttgcaggcg tcatgcagcg ggcgcgaccc acgctctggg ccgctgcgct gactctgctg     180
gtgctgctcc gcgggccgcc ggtggcgcgg gctggcgcga gctcggcggg cttgggtccc     240
gtggtgcgct gcgagccgtg cgacgcgcgt gcactggccc agtgcgcgcc tccgcccgcc     300
gtgtgcgcgg agctggtgcg cgagccgggc tgcggctgct gcctgacgtg cgcactgagc     360
gagggccagc cgtgcggcat ctacaccgag cgctgtggct ccggccttcg ctgccagccg     420
```

```
tcgcccgacg aggcgcgacc gctgcaggcg ctgctggacg ccgcgggct ctgcgtcaac    480
gctagtgccg tcagccgcct gcgcgcctac ctgctgccag cgccgccagc tccaggaaat    540
gctagtgagt cggaggaaga ccgcagcgcc ggcagtgtgg agagcccgtc cgtctccagc    600
acgcaccggg tgtctgatcc caagttccac cccctccatt caaagataat catcatcaag    660
aaagggcatg ctaaagacag ccagcgctac aaagttgact acgagtctca gagcacagat    720
acccagaact tctcctccga gtccaagcgg agacagaat atggtccctg ccgtagagaa    780
atggaagaca cactgaatca cctgaagttc ctcaatgtgc tgagtccag ggtgtacac    840
attcccaact gtgacaagaa gggattttat aagaaaaagc agtgtcgccc ttccaaaggc    900
aggaagcggg gcttctgctg gtgtgtggat aagtatgggc agcctctccc aggctacacc    960
accaagggga aggaggacgt gcactgctac agcatgcaga gcaagtagac gcctgccgca    1020
aggttaatgt ggagctcaaa tatgccttat tttgcacaaa agactgccaa ggacatgacc    1080
agcagctggc tacagcctcg atttatattt ctgtttgtgg tgaactgatt tttttaaac    1140
caaagtttag aaagaggttt tgaaatgcc tatggtttct ttgaatggta aacttgagca    1200
tcttttcact ttccagtagt cagcaaagag cagtttgaat tttcttgtcg cttcctatca    1260
aaatattcag agactcgagc acagcaccca gacttcatgc gcccgtggaa tgctcaccac    1320
atgttggtcg aagcggccga ccactgactt tgtgacttag gcggctgtgt tgcctatgta    1380
gagaacacgc ttcaccccca ctccccgtac agtgcgcaca ggctttatcg agaataggaa    1440
aacctttaaa ccccggtcat ccggacatcc caacgcatgc tcctggagct cacagccttc    1500
tgtggtgtca tttctgaaac aagggcgtgg atccctcaac caagaagaat gtttatgtct    1560
tcaagtgacc tgtactgctt ggggactatt ggagaaaata aggtggagtc ctacttgttt    1620
aaaaaatatg tatctaagaa tgttctaggg cactctggga acctataaag gcaggtattt    1680
cgggccctcc tcttcaggaa tcttcctgaa gacatggccc agtcgaaggc ccaggatggc    1740
ttttgctgcg gccccgtggg gtaggaggga cagagagaca gggagagtca gcctccacat    1800
tcagaggcat cacaagtaat ggcacaattc ttcggatgac tgcagaaaat agtgttttgt    1860
agttcaacaa ctcaagacga agcttatttc tgaggataag ctcttttaaag gcaaagcttt    1920
attttcatct ctcatctttt gtcctcctta gcacaatgta aaaagaata gtaatatcag    1980
aacaggaagg aggaatggct tgctggggag cccatccagg acactgggag cacatagaga    2040
ttcacccatg tttgttgaac ttagagtcat tctcatgctt ttctttataa ttcacacata    2100
tatgcagaga agatatgttc ttgttaacat tgtatacaac atagccccaa atatagtaag    2160
atctatacta gataatccta gatgaaatgt tagagatgct atatgataca actgtggcca    2220
tgactgagga aaggagctca cgcccagaga ctgggctgct ctcccggagg ccaaacccaa    2280
gaaggtctgg caaagtcagg ctcagggaga ctctgccctg ctgcagacct cggtgtggac    2340
acacgctgca tagagctctc cttgaaaaca gaggggtctc aagacattct gcctacctat    2400
tagctttct ttatttttt aacttttgg ggggaaagt attttgaga agtttgtctt    2460
gcaatgtatt tataaatagt aaataaagtt tttaccatta aaaaaatatc tttcccttg    2520
ttattgacca tctctgggct ttgtatcact aattatttta ttttattata taataattat    2580
tttattataa taaaatcctg aaaggggaaa ataaaaaaaa    2620
```

<210> SEQ ID NO 2
<211> LENGTH: 2393
<212> TYPE: DNA

<213> ORGANISM: Homo sapiens

<400> SEQUENCE: 2

| | | | | | |
|---|---|---|---|---|---|
| ggagtcggga | ggagcggcgg | gggcgggcgc | cggggcggg | cagaggcgcg | ggagagcgcg | 60 |
| ccgccggccc | tttatagcgc | gcggggcacc | ggctccccaa | gactgcgagc | tccccgcacc | 120 |
| ccctcgcact | ccctctggcc | ggcccagggc | gccttcagcc | caacctcccc | agccccacgg | 180 |
| gcgccacgga | acccgctcga | tctcgccgcc | aactggtaga | catggagacc | cctgcctggc | 240 |
| cccgggtccc | gcgccccgag | accgccgtcg | ctcggacgct | cctgctcggc | tgggtcttcg | 300 |
| cccaggtggc | cggcgcttca | ggcactacaa | atactgtggc | agcatataat | ttaacttgga | 360 |
| aatcaactaa | tttcaagaca | attttggagt | gggaacccaa | acccgtcaat | caagtctaca | 420 |
| ctgttcaaat | aagcactaag | tcaggagatt | ggaaaagcaa | atgcttttac | acaacagaca | 480 |
| cagagtgtga | cctcaccgac | gagattgtga | aggatgtgaa | gcagacgtac | ttggcacggg | 540 |
| tcttctccta | cccggcaggg | aatgtggaga | gcaccggttc | tgctggggag | cctctgtatg | 600 |
| agaactcccc | agagttcaca | ccttacctgg | agacaaacct | cggacagcca | acaattcaga | 660 |
| gttttgaaca | ggtgggaaca | aaagtgaatg | tgaccgtaga | agatgaacgg | actttagtca | 720 |
| gaaggaacaa | cactttccta | agcctccggg | atgttttggg | caaggactta | atttatacac | 780 |
| tttattattg | gaaatcttca | agttcaggaa | agaaaacagc | caaaacaaac | actaatgagt | 840 |
| ttttgattga | tgtggataaa | ggagaaaact | actgtttcag | tgttcaagca | gtgattccct | 900 |
| cccgaacagt | taaccggaag | agtacagaca | gcccggtaga | gtgtatgggc | caggagaaag | 960 |
| gggaattcag | agaaatattc | tacatcattg | gagctgtggt | atttgtggtc | atcatccttg | 1020 |
| tcatcatcct | ggctatatct | ctacacaagt | gtagaaaggc | aggagtgggg | cagagctgga | 1080 |
| aggagaactc | cccactgaat | gtttcataaa | ggaagcactg | ttggagctac | tgcaaatgct | 1140 |
| atattgcact | gtgaccgaga | acttttaaga | ggatagaata | catggaaacg | caaatgagta | 1200 |
| tttcggagca | tgaagaccct | ggagttcaaa | aaactcttga | tatgacctgt | tattaccatt | 1260 |
| agcattctgg | ttttgacatc | agcattagtc | actttgaaat | gtaacgaatg | gtactacaac | 1320 |
| caattccaag | ttttaattt | taacaccatg | gcaccttttg | cacataacat | gctttagatt | 1380 |
| atatattccg | cactcaagga | gtaaccaggt | cgtccaagca | aaaacaaatg | ggaaaatgtc | 1440 |
| ttaaaaaatc | ctgggtggac | ttttgaaaag | ctttttttt | tttttttttt | ttttttgagac | 1500 |
| ggagtcttgc | tctgttgccc | aggctggagt | gcagtagcac | gatctcggct | cactgcaccc | 1560 |
| tccgtctctc | gggttcaagc | aattgtctgc | ctcagcctcc | cgagtagctg | ggattacagg | 1620 |
| tgcgcactac | cacgccaagc | taattttgt | atttttagt | agagatgggg | tttcaccatc | 1680 |
| ttggccaggc | tggtcttgaa | ttcctgacct | caggtgatcc | acccaccttg | gcctcccaaa | 1740 |
| gtgctagtat | tatgggcgtg | aaccaccatg | cccagccgaa | aagcttttga | ggggctgact | 1800 |
| tcaatccatg | taggaaagta | aaatggaagg | aaattgggtg | catttctagg | acttttctaa | 1860 |
| catatgtcta | taatatagtg | tttaggttct | tttttttttc | aggaatacat | ttggaaattc | 1920 |
| aaaacaattg | gcaaactttg | tattaatgtg | ttaagtgcag | gagacattgg | tattctgggc | 1980 |
| accttcctaa | tatgctttac | aatctgcact | ttaactgact | taagtggcat | taaacatttg | 2040 |
| agagctaact | atattttat | aagactacta | tacaaactac | agagtttatg | atttaaggta | 2100 |
| cttaaagctt | ctatggttga | cattgtatat | ataattttt | aaaaggttt | tctatatggg | 2160 |
| gattttctat | ttatgtaggt | aatattgttc | tatttgtata | tattgagata | atttatttaa | 2220 |
| tatactttaa | ataaaggtga | ctgggaattg | ttactgttgt | acttattcta | tcttccatt | 2280 |

| | | |
|---|---|---|
| attatttatg tacaatttgg tgtttgtatt agctctacta cagtaaatga ctgtaaaatt | 2340 | |
| gtcagtggct tacaacaacg tatcttttc gcttataata cattttggtg act | 2393 | |

<210> SEQ ID NO 3
<211> LENGTH: 10396
<212> TYPE: DNA
<213> ORGANISM: Homo sapiens

<400> SEQUENCE: 3

| | |
|---|---|
| cgggcctggg ctgtggctgt gactggcgct gccgtgggcg ccgcagccct cgcgggagcc | 60 |
| ggacgcggta atgccccagc ggcgcagcgg gcggctgcgt ccctgagccg ctatataagc | 120 |
| gcggcaggga acatccggag gggctgaaga tgaaggtgcc cgcgcatggg ccccgctga | 180 |
| ttgccagtcc ctcccgaccc cgcgccccgc gcggagcccg aggccgccga ggacccgcct | 240 |
| tcgccgcagt agcagctgga gcagcgacag aggcggcagc tgcggcggcg cggcgcccg | 300 |
| cgcccctcgc gccagcgcgt agagcggcgg cggcagctcg ggggccgcca ctgccccggc | 360 |
| tgccatgagt tgtgcggagg tgatgtatca cccccagcct tatggagcgt cccagtatct | 420 |
| gcccaacccc atggcagcga caacctgccc cacagcctac tatcagccgg cgccccaacc | 480 |
| tggccagcag aagaagttag cggtattcag caagatgcag gactctctgg aagtcacccct | 540 |
| tcccagcaaa caagaggagg aggatgagga ggaggaggag gaggagaaag accagccctg | 600 |
| cgagatggag taccttaact ctcgctgtgt cctttcact tatttccagg gagacattgg | 660 |
| gtcagtagtg gatgaacact tctcaagagc tttgggccaa gccatcaccc tccatccaga | 720 |
| atctgccatt tcaaaagca agatgggct aacccccta tggcgagaca gctcagctct | 780 |
| ctcaagccag cggaatagtt tcccaactc cttttggacc agctcttacc agcccccacc | 840 |
| tgcaccttgt ttggggggag ttcatcctga cttccaggtc actggacccc ctggcacctt | 900 |
| ttctgcagct gatcccagtc cttggccggg acacaacctg catcagactg cccagcccc | 960 |
| tcccctgct gtgtctgagt cctggcctta tcctttgaca tctcaggtga gcccatccta | 1020 |
| cagccatatg catgacgtgt acatgcggca ccaccaccct catgcccaca tgcaccaccg | 1080 |
| ccaccgccac catcatcacc atcaccaccc tcctgctggc tctgcctgg atccatccta | 1140 |
| tgggcctctg ctgatgcctt cagtgcatgc ggccaggatt cctgctcccc agtgtgacat | 1200 |
| cacaaagaca gaaccaacta cagtcacctc tgctacctca gcatgggctg gagccttttca | 1260 |
| tggaacagta gacatagtgc ccagcgtggg attcgataca ggtctacagc atcaagacaa | 1320 |
| gagtaaggaa tcaccgtggt actgaaacac acaatcttag tgagttaagt tgcagcataa | 1380 |
| atccaagggc ccactgggaa aagatactgt cgggttttc cattcagcaa taggacacga | 1440 |
| aaggcataga aggagaagac aaagtgtcac gcagttgact ggttttcggc ctttcttgag | 1500 |
| aaagcaaagt gggtcccaga cattgaagaa aagcattttt atttgtttat ttcctcatct | 1560 |
| gagcctttgc caactgtgca actctctcct ttttgttatct tgcttttatc aatatatagc | 1620 |
| taagttttg tttcattttg atttttttt ttagccaacc accttgtcag gaaaggatga | 1680 |
| accacacatt aaaatgttca ttcttttcagg aatacaagtt tgtagctcta tgtgcatcta | 1740 |
| ttttttgtaga aatacaaaaa gtttggttta gcattgatgg gctattttg agggatgtat | 1800 |
| ttttttaaa attgtaaaaa ttgttgagtt ctgtttaaag aacttgctct cagagaagca | 1860 |
| ctggcaaaaa tgtttaaaat gcttatctct aagatgtcta ttatatgctc tgtctgtgct | 1920 |
| ttctaggtta cctcaaatgt tttgtttttt tccttcttac aaaagtagct ataccgtagt | 1980 |

```
caaaccaatg cagtattgtt tttacattga atctcagtaa agatttaatt ccatgctagc    2040
tcaattagtt ttgaattata tgtatagctt gaaaagtttt tttttaatga ctgtgctaaa    2100
gaaatgatat tttattgctt tgatttctcc caaagaataa cttggaggtt gactaataag    2160
aaagttggca taaactttca atcaaatgaa gagtttgcct agaggagact aattctcttt    2220
ctagcccatc caaatttgat aaatggaacc agaggttata tacaactaca aggaaaaaaa    2280
tgcatttaac catgccacct atgagtgcca gtgacttatt ttacttgttt ttaattattc    2340
attcatggca atttaaaaag tcatatttta agtgggattt gtttttcctg aagggcattt    2400
gaaggaacaa tatctgggaa ggtactagag aaattacaaa gcccgagctc tttcttataa    2460
tgccacctat ccctgtaagc taaacaaaca aacaaacaaa caaacaaaca gttctatata    2520
taatagtttc aacacagaac ttaacaagtc tctttttttg tttgtttaaa tctggcttta    2580
cttgatttaa ttccttttta gaaagaaatt tagggcaaaa taaagtgtat attaggattt    2640
aaatttatgc cacaatttaa aaataaaacc agaggttata tacaatttaa attgggctaa    2700
aaattaaaaa tttgaggatt taacttgata tagctctcag gatctaaata aagtttaaat    2760
tatcattaag acactgctag gagaagatta agattatgaa agtaacagtt attgatactg    2820
ctggacttca aaggcaaagt tcatttcttc cattaactgc ttccagagat gtcatgtaaa    2880
aaagttagtg tattagagaa gttttttagc tttataaaga ggttttttca aatttctccc    2940
atttttctct ccacccacat aaaatagtat gttcagtgaa atgccacttt ctatctttaa    3000
ttgttcgtat catatatgcg aacttttag acatgaacat gacatgttca gctaggcaga    3060
gttctcatag ataattttca aatatttcc ttggctgtaa tttatgtatt catttatatc    3120
ctatccgtct tttgagcttc agatctatat actcttttgt actctcatca ctccgcactt    3180
tgctgtttct tacctagact ctcttttaca caatatgcac attttttacca ttgtgggtc    3240 caaatttaag ataccttcca ctcactaata atatgaactt atatttcctg ggagtagcca    3300
ggttaaattt tctatacttt ggtccataat ttgatttgat atgattgttt catttataat    3360
ttgcccaaat acatggagca caaaatttag tgaatttata atctggatt tgccttgtgt    3420 ccttctgagt tttcaaaggc aagtattcaa cagtccctgt gtgatgactg acagggttat    3480
ttgcctcatc cacatccacc ttcggaatac attaacttcc tttgtaattt atttgaaagt    3540
agtgttaaac tcattcagat cattcagttg gattttccca atgaagagga aaaggaaagt    3600
agttattcct agctccattt cttatttttcc accaaattta attgaagggc attaattaga    3660
tgtcttcacc ctgaatttag actttgctct gtgttctccc ggtaactgtc agacaaaaag    3720
tttattggct ctgaggaact gagaaatgtt gggaacctgg tttctgctgt acacaggaaa    3780
gatttgtaag tgagctctct ctttgaaaac aggacccagg ctgggcacag cagctcatgc    3840
ctgtaatcct agtattatag gaggcagagg ctcgggagga ttgcttgagc ccaggagttc    3900
aagatcagcc taggcaacat agggagaccc tatccctaca aaaaatttct gaaaaattac    3960
ctgggcattg tggggcacac ctgttgtccc agctactctg gaggctgagt ccggaggaac    4020
gtttgagcct gggagtttga gtttgcagct tgcagtgagc tgtgattgca ccactgtact    4080
ccagcttggg caacagagca agatcctgtc tcaaaaggaa aaagaaaaca ggacctaggt    4140 gtttgggta cactgccacc cagggagtgg atcaaaaata tacatagaaa gagaatgagc    4200
atgtctctat aattgtcttc taggaccata ttgctgttag aagtcctaaa agaggatggg    4260
ttgtaattta gcataatatt ctgaattcat tccaagttta aaatcctgtc attctctggc    4320
tcttcttttt tcacatcaaa atgatgctgt tggacttaga ggcttccgaa ctgttttatt    4380
```

```
gagggctact atctgcctcc acaatttat taaaaccact ccacctttag acaaaggtga   4440
cttttgtctg attttacaaa tcagatttta ttcaagcttt ctaaatatct gtgaagtaga   4500
ccctagaaaa ttgtctcgtt tatttaaat agaatctatg cttccaccaa taaaccatcg   4560
ggagctaaga acaacataa tgttgacaaa tcaggaacct aacagattat tttgtctctc   4620
attattaatt tgaaagagcc tctaaacttt tgagaaatca atgtgtcttc ttaagaaagt   4680
taagcaccct ctcttaactt tcccctctat ttgctctcct ttttctttct tcttaagagt   4740
atttatatta ttttgttaag caaaaatggc taagattgct ctaaaatttg caaatgagg    4800
agtggattgc aaataattga gggatttatt tctttaactt tataagactt taaaaaaaaa   4860
acccaaattc taagcactga catgaaagtt gcctttgaga agcttgttat tcattataca   4920
aaaagtattt gcccattcct attctaagat ttgcagaata tgtcaccta tctagctttt    4980
gagtttgcta tctggtttaa tgttgtattt ataatttaaa gtggaaatca gaaactgttt   5040
caagaacctg tattctattc cttactgagt gtcccttctt taaatagtgt ttgctgaatt   5100
aagccgatgg gggcagtggc gttaagtggt ggaaaaagga agtatatat gttagagttt    5160
tgaatgaggg ataaatagaa agcagaatga attaatggaa aagaactcgg ctgttaggcc   5220
attctctaaa ttctagttta gccaaaagtt tatgtgtggt ttgggcttc atttatttat    5280
ctcatgagta aaatggaata atacctaaca ggcaggctct ggaagttgga aatcacatac   5340
acacacacac acacacagac acacacacac acgatcaatc atgtagctca tattagatgt   5400
tcaataaata acagctacta cagatgccta tcagttgagt aagtagttca ttaaattgag   5460
ctcccaaagg tctcttctct tcacatccat atccgtttct gcagcaatca aatagataca   5520
tgattgtttt tctgtaagaa attactgcaa agagaatctt tttctcctac taactgttcc   5580
ttctacctgg tataggagat aaatgtacgt ttcttaatta gctgactttt tagtatgtca   5640
tttctgaagg aaaaataaat taaccttaaa gtggcatgta ggtccaattc agtttcccta   5700
catgttccaa aattttattt aaattactgt gtccaaaatt atgaggacag tgtcattcat   5760
tcaccatagt ttatatttt agttatatat caaacttcct tggcacctag gataagaaca   5820
tttcttttga agttatccaa ttttttttta ttttacttg acttgaagga aagttggaaa   5880
atatggtgga aaaatcttc cgcattaaaa gggggaaaaa cacaaccatt tacgatctca   5940
gtcagcagat ttactctact caaggaaaaa agaaacaat cttattggaa gcagatgttg    6000
acactgtgtc agttattgaa gacggaagga gttcacttga gccattgcag ttacaaaggg   6060
gtattgatgg cagtttggat tcctgattga tcacctttgc agccaaggga aagacagcag   6120
aaactgtatg ggatcagaaa tgaaatcagc ctgccagttt aatggagagg ctcctagaaa   6180
ctcattttt ttctttcctg taagataaaa gacatcttc agaataagaa aggcttgttt     6240
gagagagaaa ttacagttta ttctctgaaa atatttaaag gccaaagtgc cctttaaatc   6300
tattattaaa gcattgaaac tgttattaaa atcattatag aaaaattagg taaaaatttt   6360
agcctaactt tcaacatcca ttcaaaaacg aatgttgaaa acaaacatat aacctataaa   6420
aaagtgaatg gctctggcaa gtgggggcat gggtggagtc cataaggaaa cctcagtctc   6480
aataacttca aaatgttact tttcatggta acttggtcat ggagattggt cacagcacag   6540
acatttagaa ttttttagca ggttttttt ttcttttgaa tcttgtagtg ctctctggga    6600
attgcaccat gtacactttt acaacctaca gaaatcgtca ttattgttaa agtatctcaa   6660
cttttctatt tcttttattg tctattgtgc ttttttgttt aaaaatactt ttatagtttt   6720
```

```
aaagtattgg tcaaagtagt attctcttga agttctagtc aatttaattt gatccaataa   6780
gtttttctga atctccttt taagttccaa gaaattctat tataaataag tgtactttta    6840
ccaattccat tgtataagca aacagacacc ttttagaaaa ggataagtaa tcatcaattt   6900
gtttttttaa aaaaaaaaac aatttctaga ctactaaatt tggcataaga ataattcttt   6960
taaaatgcaa catactttaa ttagtttttt tggtatatgc ataagatgtg aactttccta   7020
ttgatatcac tttatattaa tagagatgta catttctttc tatgccgtgg ctagagcaaa   7080
agttaataat gattatttac acaattgatt taatttctta ggatatgtat aatattggat   7140
attatatctg atttaaaaat actattccat acatttttt tttcaggaga taaaacatag    7200
ggaaaggttt tcatgtgaat tctttgtatc actttgaagt acatatattt aaagggaaga   7260
tggatacaat tgttttat tatataaatc taggtaaggt gaaatgcttt tgtcaacaaa     7320
aatacagtgt agtgaatttt atatttgtca cttgattagg taaactgaaa actaacaata   7380
gaaatattat tttactgcat tgaaatacca tgaactttca gacttgttag ttctacaaga   7440
agttgtgcta ccttaatttt gtgttccag aaataaaaat taaccttagt tatgctgtca    7500
ttttaacta ataaaaaaag tataattcat aaaacttttg ctttataag ataattataa     7560
aattatatat tttttctgt ttttgtgggg ttgggaaaac atttcttat ttctattcac     7620
tcttcaaatg caggtctcat aatatgtgtc aatgatataa gatgatggaa gactttgtaa   7680
taaaacata tgtcattatc ttcaatttgt tcaataaata atttaatgtg aattgaatgt    7740
ttgtatttta acatagcatt tggatttggt ctgcatttct tgagaattta aagctctttt   7800
tgtttcctcc ttattcaatt aagcatctta taaatatttt ggaaattaca acatcttagg   7860
tgttattaat taagaagtta atttctaggg ccaagaagtc tatatgttac agcaaggaat   7920
agattataaa atacatgttt ataatggaaa agaaaatgaa atggggtata ttaattacat   7980
aacagcaaga gtcttgagaa ttttataata caatgcttct aaggatattg gttgaccaag   8040
gtgtattta ttgttttac atttgttgac agggactctg ccataagtag tatgaaaaaa     8100
caaacaaaaa cttttctacg attcattaac attgaaaaga gaattccaag accttgtatt   8160
ctgaagaaag ctagagtttc tctaagtggg ccttcaattt tcttattaca cgtatcttta   8220
atgtgaaagt actaaagtct gaaaatcagc atttaaataa tagactttcc agcattacag   8280
atgaaataat ttggcgcagg cttttttaact gtctaccata tttagaatgt ggtgtcaaaa   8340
tgagattttt agaactgctg taaaatatta ctacattact acaacgataa cggcctaaaa   8400
caacacaaat ttattatctt acagctctgt cagtcagaca ttcagcaaag atcttagtct   8460
tggtgggcta cagaatgtag gaggcatttc ctggatgctt ccaagagaga atcttgctgt   8520
tccctgcttc tagagtcctt tgcttagttt ccttccatct tcaaatccag caacctggtc   8580
aagaccttct cacatgacat cactgacttc ctcttcttcc tctcccttac atatttaagg   8640
actcatgtga ttacaatagc tgcatctgtg taatccagaa taatctcttc atctcaaggt   8700
ttttgttctg ttttgttttt ttgttttgtt ttgttttgtt tgttttgat ggagtcttgc    8760
tctgtcgtca ggctggagtg cagtggcgcg atctcggctc actccaacct ccacctcccg   8820
ggttcaaagg attcccctgc ctcagcctct cgagtagctg ggactacaga tgcgtgctac   8880
cacacaaggc taatattttg tattttagta gagacgggat ttcaccatgt tggccaggat   8940
ggtctccgtc tcctgacctc gtgatctgcc tgccttggcc tcccaaagtg ttgggattac   9000
aggcataagc cattgcgcca tgctcaaggt tcttaattac atctttaaag gcccttttc    9060
catgtacagt aacatattca atggttctgg ggattaggac ttggagccat tattctacct   9120
```

```
acaacaatta gtattggact tccatcattt tctatcactc ttgtaatcga gaaggactat    9180
ttcactggga gtagcaagtc ataatgtttg cgttggcatt tgtgtggggg tttatcttca    9240
ttcattaaat aattgcatgt aaagaaaatt cctgtcacta tttcaaatgt tcatgtagt     9300 tattatagtg cttcagaatc caagggtta tgtgttactt atgtaagatg agcagtctag    9360
ggggtggaga acaggtcatc tagtgcagat tcttcctagc tgaagtgtgt tttctctggg    9420
gacaaccaag taggatttaa ttgttttgct tccttttttg ggaacttaga cccatccttgc   9480 gatgtcctaa gtctccaagc atcttatttg acctgcttat acacatttga ctaaatagct    9540
aaatatgacc acattgacgt ggtaaagctt taacactttt gtccagattg aatcactcca    9600
tctgctatca gttaagcagt ggaaaactgt tatggaaaag caaacatgtt ttgatagatt    9660
taatgtgtaa agaaggtatc catactctgg aatgctgctg atcaataaat gagctgcaag    9720
actttgttcg aaacaacact caagcacaac tgttttactt tccataccaa gtttggctgt    9780
gactgaatga agaacatcag cattgatctt tgctttgcac ttgtacaaga gactatttgc    9840
agagagccaa atatagcaac agaggattta atatcttgcc aaaaaataca aaatctgttc    9900
ccctttaagc atgacactct atcctttctt gtggatcttg ctaaaaggaa aatatagctt    9960
taaactcccc tattccttct gttgaaagct taagaatctt tttcaaatga gctatgtatg   10020
gttttgtggt attttatgtt tccaaaagaa aatggctaca tgaaaatct gtccagtgtt    10080 atcattttc ttacaaaaaa tacttctagt tatggttgta ttaattaatt tgattgtgat    10140
aatgattaca caatgtttac ctatatcaaa tcatcatatc gtataccttta aatatatata  10200 acttttatgt gtcaattata actcagtaag tctgggaaaa tatcgttaag tcaaagatta   10260
gagtcaacag aaataaagaa aaatcatact ttgataactt caggactaat caaggatcaa   10320
tgggtgacat gatatcatgc tatgtgccat tttgtgttaa acaaattaca ccaacaataa   10380
aaaaaattgg cttcaa                                                   10396

<210> SEQ ID NO 4
<211> LENGTH: 2656
<212> TYPE: DNA
<213> ORGANISM: Homo sapiens

<400> SEQUENCE: 4
gaggctttaa aatctttttt catcttctag ctgtagctcg ggctgcttgt cggcttggcc      60
tccccctccc ccctttgctc tctgcctcgt cttcccccag gacttcgcta ttttgctttt    120
ttaaaaaaag gcaagaaaga actaaactcc cccctccctc tcctccagtc gggctgcacc    180
tctgccttgc actttgcaca gaggtagaga gcgcgcgagg gagagagagg aaagaaaaaa    240
aataataaag agagccaagc agaagaggag gcgagaagca tgaagtgtta actccccgt    300 gccaaggccc gcgccgcccg gacagacgcc cgccgcgcct ccagccccga gcggacgccg    360
cgcgcgccct gcctgcagcc cgggccggcg aggcgagccc ttccttatgc aaagcgcgca    420
gcggagcggc gagcggggga cgccgcgcac cgggccgggc tcctccagct tcgccgccgc    480
agccaccacc gccgccaccg cagctcgcgg aggatcttcc cgagcctgaa gccgccggct    540
cggcgcgcaa ggaggcgagc gagcaaggag gggccggggc gagcgaggga gcacattggc    600
gtgagcaggg gggagggagg gcgggcgcgg ggggcgcggg cagggcgggg gggtgtgtgt    660
gtgagcgcgc tcgagggttt cgggccagcc accgccgcgc aagctagaag cgccccagcc    720
cggcaagctg gctcacccgc tggccacccca gcacagcccg ctggcccctc tcctgcagcc    780
```

| | |
|---|---|
| catctggcgg agcggcggcg gcggcggcgg cggcggcagg agaatggcat cagaactggc | 840 |
| aatgagcaac tccgacctgc ccaccagtcc cctggccatg gaatatgtta atgacttcga | 900 |
| tctgatgaag tttgaagtga aaaggaacc ggtggagacc gaccgcatca tcagccagtg | 960 |
| cggccgtctc atcgccgggg gctcgctgtc ctccaccccc atgagcacgc cgtgcagctc | 1020 |
| ggtgccccct tcccccagct tctcggcgcc cagcccgggc tcgggcagcg agcagaaggc | 1080 |
| gcacctggaa gactactact ggatgaccgg ctacccgcag cagctgaacc ccgaggcgct | 1140 |
| gggcttcagc cccgaggacg cggtcgaggc gctcatcagc aacagccacc agctccaggg | 1200 |
| cggcttcgat ggctacgcgc gcggggcgca gcagctggcc gcggcggccg gggcggtgc | 1260 |
| cggcgcctcc ttgggcggca gcggcgagga gatgggcccc gccgccgccg tggtgtccgc | 1320 |
| cgtgatcgcc gcggccgccg cgcagagcgg cgcgggcccg cactaccacc accaccacca | 1380 |
| ccacgccgcc ggccaccacc accacccgac ggccggcgcg cccggcgccg cgggcagcgc | 1440 |
| ggccgcctcg gccggtggcg ctgggggcgc gggcggcggt ggcccggcca gcgctggggg | 1500 |
| cggcggcggc ggcggcggcg cggaggcgg cggggcgcg cgggggcgg ggggcgccct | 1560 |
| gcacccgcac cacgccgccg gcggcctgca cttcgacgac cgcttctccg acgagcagct | 1620 |
| ggtgaccatg tctgtgcgcg agctgaaccg gcagctgcgc ggggtcagca aggaggaggt | 1680 |
| gatccggctg aagcagaaga ggcggacct gaaaaaccgc ggctatgccc agtcctgccg | 1740 |
| cttcaagagg gtgcagcaga gacacgtcct ggagtcggag aagaaccagc tgctgcagca | 1800 |
| agtcgaccac ctcaagcagg agatctccag gctggtgcgc gagagggacg cgtacaagga | 1860 |
| gaaatacgag aagttggtga gcagcggctt ccgagaaaac ggctcgagca gcgacaaccc | 1920 |
| gtcctctccc gagtttttca taactgagcc cactcgcaag ttggagccat cagtgggata | 1980 |
| cgccacattt tggaagcccc agcatcgtgt acttaccagt gtgttcacaa aatgaaattt | 2040 |
| gtgtgagagc tgtacattaa aaaaaatcat cattattatt attatttgca gtcatggaga | 2100 |
| accacctacc cctgacttct gtttagtctc cttttaaat aaaaattact gtgttagaga | 2160 |
| agaaggctat taaatgtagt agttaactat gcctcttgtc tgggggtttc atagagaccg | 2220 |
| gtaggaaagc gcactcctgc ttttcgattt atggtgtgtg caagtaaaca ggtgcattgc | 2280 |
| tttcaacctg ccatactagt tttaaaaatt cactgaaatt acaagatac atatatatgc | 2340 |
| atatatataa tggaaagttt cccggaatgc aacaattagc attttaaaat catatatagg | 2400 |
| catgcacatt ctaaatagta cttttcatg cttcattgtt tctctggcag ataatttac | 2460 |
| taagaagaaa aatagatatt cgactcccct tccctaaaca aatccacggg cagaggctcc | 2520 |
| agcggagccg agcccctgg ttttctcgta ggccctagac ggtgttgcat ttatcagtga | 2580 |
| tgtcaaacgt gctcatttgt cagacatagc tgtaaatgaa acaatgtgt ggcaaaatac | 2640 |
| aaagttaaaa aaaaaa | 2656 |

<210> SEQ ID NO 5
<211> LENGTH: 6887
<212> TYPE: DNA
<213> ORGANISM: Homo sapiens

<400> SEQUENCE: 5

| | |
|---|---|
| gaggctttaa aatcttttttt catcttctag ctgtagctcg ggctgcttgt cggcttggcc | 60 |
| tcccccctccc ccctttgctc tctgcctcgt cttcccccag gacttcgcta ttttgctttt | 120 |
| ttaaaaaaag gcaagaaaga actaaactcc cccctccctc tcctccagtc gggctgcacc | 180 |
| tctgccttgc actttgcaca gaggtagaga gcgcgcgagg gagagagagg aaagaaaaaa | 240 |

```
aataataaag agagccaagc agaagaggag gcgagaagca tgaagtgtta actccccgt    300 gccaaggccc gcgccgcccg gacagacgcc cgccgcgcct ccagcccga gcggacgccg    360 cgcgcgccct gcctgcagcc cgggccggcg aggcgagccc ttccttatgc aaagcgcgca   420
gcggagcggc gagcggggga cgccgcgcac cgggccgggc tcctccagct tcgccgccgc   480
agccaccacc gccgccaccg cagctcgcgg aggatcttcc cgagcctgaa gccgccggct   540
cggcgcgcaa ggaggcgagc gagcaaggag gggccggggc gagcgaggga gcacattggc   600
gtgagcaggg gggagggagg gcgggcgcgg ggggcgcggg cagggcgggg gggtgtgtgt   660
gtgagcgcgc tcggaggttt cgggccagcc accgccgcgc aagctagaag cgccccagcc   720
cggcaagctg gctcacccgc tggccaccca gcacagcccg ctggcccctc tcctgcagcc   780
catctggcgg agcggcggcg gcggcggcgg cggcggcagg agaatggcat cagaactggc   840
aatgagcaac tccgacctgc ccaccagtcc cctggccatg gaatatgtta atgacttcga   900
tctgatgaag tttgaagtga aaaggaacc ggtggagacc gaccgcatca tcagccagtg   960
cggccgtctc atcgccgggg gctcgctgtc ctccaccccc atgagcacgc cgtgcagctc   1020 ggtgcccct tccccagct tctcggcgcc cagcccgggc tcgggcagcg agcagaaggc    1080
gcacctggaa gactactact ggatgaccgg ctaccgcag cagctgaacc ccgaggcgct    1140
gggcttcagc cccgaggacg cggtcgaggc gctcatcagc aacagccacc agctccaggg   1200
cggcttcgat ggctacgcgc gcggggcgca gcagctggcc gcggcggccg gggccggtgc   1260
cggcgcctcc ttgggcggca gcggcgagga gatgggcccc gccgccgccg tggtgtccgc   1320
cgtgatcgcc gcggccgccg cgcagagcgg cgcgggcccg cactaccacc accaccacca   1380
ccacgccgcc ggccaccacc accacccgac ggccggcgcg cccggcgccg cgggcagcgc   1440
ggccgcctcg gccggtggcg ctgggggcgc gggcggcggt ggcccggcca gcgctggggg   1500
cggcggcggc ggcggcggcg gcggaggcgg cggggggcgcg gcggggcgg ggggcgccct   1560 gcacccgcac cacgccgccg gcggcctgca cttcgacgac cgcttctccg acgagcagct   1620
ggtgaccatg tctgtgcgcg agctgaaccg gcagctgcgc ggggtcagca aggaggaggt   1680
gatccggctg aagcagaaga ggcggaccct gaaaaaccgc ggctatgccc agtcctgccg   1740
cttcaagagg gtgcagcaga gacacgtcct ggagtcggag aagaaccagc tgctgcagca   1800
agtcgaccac ctcaagcagg agatctccag gctggtgcgc gagagggacg cgtacaagga   1860
gaaatacgag aagttggtga gcagcggctt ccgagaaaac ggctcgagca gcgacaaccc   1920
gtcctctccc gagttttca tgtgagtctg acacgcgatt ccagctagcc accctgataa   1980
gtgctccgcg ggggtccggc tcgggtgtgg gcttgctagt tctagagcca tgctcgccac   2040
cacctcacca ccccaccccc caccgagttt ggccccttg gccccctaca cacacacaaa   2100
cccgcacgca cacaccacac acacacacac acacacacac acaccccaca ccctgctcga   2160
gtttgtggtg gtggtggctg ttttaaactg ggagggaat gggtgtctgg ctcatggatt   2220
gccaatctga aattctccat aacttgctag cttgttttt ttttttttt acacccccc    2280 gccccacccc cggacttgca caatgttcaa tgatctcagc agagttcttc atgtgaaacg   2340
ttgatcacct ttgaagcctg catcattcac atattttttc ttcttcttcc ccttcagttc   2400
atgaactggt gttcattttc tgtgtgtgtg tgtgttttat tttgtttgga tttttttttt   2460
taattttact tttagagctt gctgtgttgc ccacctttt tccaacctcc ccctcactc    2520 cttctcaacc catctcttcc gagatgaaag aaaaaaaaaa gcaaagtttt tttttcttct   2580
```

```
cctgagttct tcatgtgaga ttgagcttgc aaaggaaaaa aaaatgtgaa atgttataga    2640
cttgcagcgt gccgagttcc atcgggtttt tttttttagca ttgttatgct aaaatagaga   2700
aaaaaatcct catgaacctt ccacaatcaa gcctgcatca accttctggg tgtgacttgt    2760
gagttttggc cttgtgatgc caaatctgag agtttagtct gccattaaaa aaactcattc    2820
tcatctcatg cattattatg cttgctactt tgtcttagca acaatgaact ataactgttt    2880
caaagacttt atggaaaaga gacattatat taataaaaaa aaaagcctg catgctggac     2940 atgtatggta taattatttt ttccttttt tttccttttg cttggaaat ggacgttcga      3000 agacttatag catggcattc atacttttgt tttattgcct catgactttt ttgagtttag    3060
aacaaaacag tgcaaccgta gagccttctt cccatgaaat tttgcatctg ctccaaaact    3120
gctttgagtt actcagaact tcaacctccc aatgcactga aggcattcct tgtcaaagat    3180
accagaatgg gttacacatt taacctggca acattgaag aactcttaat gttttctttt     3240
taataagaat gacgcccac tttggggact aaaattgtgc tattgccgag aagcagtcta    3300
aaatttattt tttaaaaga gaactgccc cattatttt ggtttgtttt attttttattt     3360 tatattttt ggcttttggt cattgtcaaa tgtggaatgc tctgggtttc tagtatataa    3420
tttaattcta gttttataa tctgttagcc cagttaaaat gtatgctaca gataaaggaa    3480
tgttatagat aaatttgaaa gagttaggtc tgtttagctg tagattttt aaacgattga    3540 tgcactaaat tgtttactat tgtgatgtta aggggggtag agtttgcaag gggactgttt   3600
aaaaaaagta gcttatacag catgtgcttg caacttaaat ataagttggg tatgtgtagt   3660
ctttgctata ccactgactg tattgaaaac caaagtatta agaggggaaa cgcccctgtt   3720
tatatctgta ggggtatttt acattcaaaa atgtatgttt ttttttcttt tcaaaattaa   3780
agtatttggg actgaattgc actaagatat aacctgcaag catataatac aaaaaaaaat   3840
tgcaaaactg tttagaacgc taataaaatt tatgcagtta taaaaatggc attactgcac   3900
agttttaaga tgatgcagat tttttttacag ttgtattgtg gtgcagaact ggattttctg  3960
taacttaaaa aaaaatccac agttttaaag gcaataatca gtaaatgtta ttttcaggga   4020
ctgacatcct gtctttaaaa agaaatgaaa agtaaatctt accacaataa atataaaaaa   4080
atcttgtcag ttacttttct tttacatatt ttgctgtgca aaattgtttt atatcttgag   4140
ttactaacta accacgcgtg ttgttcctat gtgcttttct ttcatttca attctggtta    4200 tatcaagaaa agaataatct acaataataa acggcatttt tttttgattc tgtactcagt   4260
ttcttagtgt acagtttaac tgggcccaac aacctcgtta aaagtgtaaa atgcatcctt   4320
ttctccagtg gaaggattcc tggaggaata gggagacagt aattcagggt gaaattatag   4380 gctgttttt gaagtgagga ggctggcccc atatactgat tagcaatatt taatatagat    4440
gtaaattatg acctcatttt tttctcccca aagttttcag ttttcaaatg agttgagcca   4500
taattgccct tggtaggaaa aacaaaacaa aacagtggaa ctaggcttcc tgagcatggc   4560
cctacacttc tgatcaggag caaagccatc catagacaga ggagccggac aaatatggcg   4620
catcagaggt ggcttgcgca catatgcatt gaacggtaaa gagaaacagc gcttgccttt   4680
tcactaaagt tgactatttt tccttcttct cttacacacc gagatttct tgttagcaag    4740 gcctgacaag atttaacata aacatgacaa atcatagttg tttgttttgt tttgcttttc   4800
tctttaacac tgaagatcat ttgtcttaaa taggaaaaag aaaatccact ccttacttcc   4860
atatttccaa gtacatatct ggtttaaact atgttatcaa atcatattc accgtgaata    4920 ttcagtggag aacttctcta cctggatgag ctagtaatga tttcagatca tgctatcccc   4980
```

```
agaaataaaa gcaaaaaata atacctgtgt ggaatatagg ctgtgctttg atttactggt     5040
atttacccca aaataggctg tgtatggggg ctgacttaaa gatcccttgg aaagactcaa     5100
aactaccttc actagtagga ctcctaagcg ctgacctatt tttaaatgac acaaattcat     5160
gaaactaatg ttacaaattc atgcagtttg cactcttagt catcttcccc tagcacacca     5220
atagaatgtt agacaaagcc agcactgttt tgaaaataca gccaaacacg atgacttttg     5280
ttttgttttc tgccgttctt aaagaaaaaa aagataatat tgcaactctg actgaaagac     5340
ttatttttaa gaaaacaggt tgtgtttggt gctgctaagt tctggccagt ttatcatctg     5400
gccttcctgc ctattttta caaaacacga agacagtgtg taacctcgac attttgacct     5460
tcctttatgt gctagtttag acaggctcct gaatccacac ttaattttgc ttaacaaaag     5520
tcttaatagt aaacctcccc tcatgagctt gaagtcaagt gttcttgact tcagatattt     5580
ctttcctttt tttttttttt tcctcatcac aactaagaga tacacaaact ctgaagaagc     5640
agaaatggag agaatgcttt taacaaaaaa gcatctgatg aaagatttta ggcaaacatt     5700
ctcaaaataa gagtgatatt ctggatgtag ttattgcagt tatctcatga caaatgaggc     5760
ctggattgga aggaaaatat agttgtgtag aattaagcat tttgatagga atctacaagg     5820
tagttgaata taataagcag gtttgggccc ccaaacttta gaaaatcaaa tgcaaaggtg     5880
ctggcaaaaa tgaggtttga gtggctggct gtaagagaag gttaactcct agtaaaaggc     5940
atttttagaa ataacaatta ctgaaaactt tgaagtatag tgggagtagc aaacaaatac     6000 atgtттттттт tttcttacaa agaactccta aatcctgagt aagtgccatt cattacaata     6060
agtctctaaa tttaaaaaaa aaaaaatcat atgaggaaat ctagctttcc cctttacgct     6120
gcgtttgatc tttgtctaaa tagtgttaaa attccттттca ttccaattac agaactgagc     6180
ccactcgcaa gttggagcca tcagtgggat acgccacatt ttggaagccc cagcatcgtg     6240
tacttaccag tgtgttcaca aaatgaaatt tgtgtgagag ctgtacatta aaaaaaatca     6300
tcattattat tattatttgc agtcatggag aaccacctac ccctgacttc tgtttagtct     6360 ccttттттaaa taaaaattac tgtgttagag aagaaggcta ttaaatgtag tagttaacta     6420
tgcctcttgt ctgggggttt catagagacc ggtaggaaag cgcactcctg cttttcgatt     6480
tatggtgtgt gcaagtaaac aggtgcattg ctttcaacct gccatactag ttttaaaaat     6540
tcactgaaat tacaaagata catatatatg catatatata atggaaagtt tcccggaatg     6600
caacaattag cattttaaaa tcatatatag gcatgcacat tctaaatagt actttttcat     6660
gcttcattgt ttctctggca gataatttta ctaagaagaa aaatagatat tcgactcccc     6720

ttccctaaac aaatccacgg gcagaggctc cagcggagcc gagccccctg gttttctcgt     6780
aggccctaga cggtgttgca tttatcagtg atgtcaaacg tgctcatttg tcagacatag     6840
ctgtaaatga aacaatgtg tggcaaaata caaagttaaa aaaaaa                    6887
```

<210> SEQ ID NO 6
<211> LENGTH: 2251
<212> TYPE: DNA
<213> ORGANISM: Homo sapiens

<400> SEQUENCE: 6

```
gaccattagc aggcacccag gcctgtcttt ggctcggaaa cggtggcccc caatgtagcc       60
tagtttgaac ctaggaactg caggaccaga gagattccac tggagcctga tggacgggtg      120
acagagggaa ccctactctg gaaactgtca gtcccagggc actggggagg gctgaggccg      180
```

```
accatgccca gcctgctgct gctgttcacg gctgctctgc tgtccagctg ggctcagctt    240
ctgacagacg ccaactcctg gtggtcatta gctttgaacc cggtgcagag acccgagatg    300
tttatcatcg gtgcccagcc cgtgtgcagt cagcttcccg gctctcccc tggccagagg     360
aagctgtgcc aattgtacca ggagcacatg gcctacatag ggagggagc caagactggc     420
atcaaggaat gccagcacca gttccggcag cggcggtgga attgcagcac agcggacaac    480
gcatctgtct ttgggagagt catgcagata ggcagccgag agaccgcctt cacccacgcg    540
gtgagcgccg cgggcgtggt caacgccatc agccgggcct gccgcgaggg cgagctctcc    600
acctgcggct gcagccggac ggcgcggccc aaggacctgc cccgggactg gctgtggggc    660
ggctgtgggg acaacgtgga gtacggctac cgcttcgcca aggagtttgt ggatgcccgg    720
gagcgagaga gaactttgc caaaggatca gaggagcagg gccgggtgct catgaacctg     780
caaaacaacg aggccggtcg cagggctgtg tataagatgg cagacgtagc ctgcaaatgc    840
cacggcgtct cggggtcctg cagcctcaag acctgctggc tgcagctggc cgagttccgc    900
aaggtcgggg accggctgaa ggagaagtac gacagcgcgg ccgccatgcg cgtcacccgc    960
aagggccggc tggagctggt caacagccgc ttcacccagc ccaccccgga ggacctggtc   1020
tatgtggacc ccagccccga ctactgcctg cgcaacgaga gcacgggctc cctgggcacg   1080
cagggccgcc tctgcaacaa gacctcggag ggcatggatg gctgtgagct catgtgctgc   1140
gggcgtggct acaaccagtt caagagcgtg caggtggagc gctgccactg caagttccac   1200
tggtgctgct tcgtcaggtg taagaagtgc acggagatcg tggaccagta catctgtaaa   1260
tagccccgag ggcctgctcc cggccccct gcactctgcc tcacaaaggt ctatattata    1320
taaatctata taaatctatt ttatatttgt ataagtaaat gggtgggtgc tatacaatgg   1380
aaagatgaaa atgaaaggaa agagcttatt taagagacgc tggagatctc tgaggagtgg   1440
actttgctgg ttctctcctc ttggtgggtg ggagacaggg cttttctct ccctctggcg    1500
aggactctca ggatgtaggg acttggaaat atttactgtc tgtccaccac ggcctggagg   1560
agggaggttg tggttggatg gaggagatga tcttgtctgg aagtctagag tctttgttgg   1620
ttagaggact gcctgtgatc ctggccacta ggccaagagg ccctatgaag gtggcgggaa   1680
ctcagcttca acctcgatgt cttcagggtc ttgtccagaa tgtagatggg ttccgtaaga   1740
ggcctggtgc tctcttactc tttcatccac gtgcacttgt gcggcatctg cagtttacag   1800
gaacggctcc ttccctaaaa tgagaagtcc aaggtcatct ctggcccagt gaccacagag   1860
agatctgcac ctcccggact tcaggcctgc ctttccagcg agaattcttc atcctccacg   1920
gttcactagc tcctacctga agaggaaagg gggccatttg acctgacatg tcaggaaagc   1980
cctaaactga atgtttgcgc ctgggctgca gaagccaggg tgcatgacca ggctgcgtgg   2040
acgttatact gtcttcccc accccgggg aggggaagct tgagctgctg ctgtcactcc     2100
tccaccgagg gaggcctcac aaaccacagg acgctgcaac gggtcaggct ggcgggcccg   2160
gcgtgctcat catctctgcc ccaggtgtac ggtttctctc tgacattaaa tgcccttcat   2220
ggaaaaaaaa aaaaaaaaaa aaaaaaaaa a                                   2251
```

<210> SEQ ID NO 7
<211> LENGTH: 2358
<212> TYPE: DNA
<213> ORGANISM: Homo sapiens

<400> SEQUENCE: 7

```
aaactcacac aacaactctt ccccgctgag aggagacagc cagtgcgact ccaccctcca    60
```

```
gctcgacggc agccgccccg gccgacagcc ccgagacgac agcccggcgc gtcccggtcc    120
ccacctccga ccaccgccag cgctccaggc cccgccgctc cccgctcgcc gccaccgcgc    180
cctccgctcc gcccgcagtg ccaaccatga ccgccgccag tatgggcccc gtccgcgtcg    240
ccttcgtggt cctcctcgcc ctctgcagcc ggccggccgt cggccagaac tgcagcgggc    300
cgtgccggtg cccggacgag ccggcgccgc gctgcccggc gggcgtgagc ctcgtgctgg    360
acggctgcgg ctgctgccgc gtctgcgcca agcagctggg cgagctgtgc accgagcgcg    420 accccctgcga cccgcacaag ggcctcttct gtgacttcgg ctccccggcc aaccgcaaga    480
tcggcgtgtg caccgccaaa gatggtgctc cctgcatctt cggtggtacg gtgtaccgca    540
gcggagagtc cttccagagc agctgcaagt accagtgcac gtgcctggac ggggcggtgg    600
gctgcatgcc cctgtgcagc atggacgttc gtctgcccag ccctgactgc cccttcccga    660
ggagggtcaa gctgcccggg aaatgctgcg aggagtgggt gtgtgacgag cccaaggacc    720
aaaccgtggt tgggcctgcc ctcgcggctt accgactgga agacacgttt ggcccagacc    780
caactatgat tagagccaac tgcctggtcc agaccacaga gtggagcgcc tgttccaaga    840
cctgtgggat gggcatctcc acccgggtta ccaatgacaa cgcctcctgc aggctagaga    900
agcagagccg cctgtgcatg gtcaggcctt gcgaagctga cctggaagag aacattaaga    960
agggcaaaaa gtgcatccgt actcccaaaa tctccaagcc tatcaagttt gagctttctg   1020
gctgcaccag catgaagaca taccgagcta aattctgtgg agtatgtacc gacggccgat   1080
gctgcacccc ccacagaacc accacccctgc cggtggagtt caagtgccct gacggcgagg   1140
tcatgaagaa gaacatgatg ttcatcaaga cctgtgcctg ccattacaac tgtcccggag   1200
acaatgacat ctttgaatcg ctgtactaca ggaagatgta cggagacatg gcatgaagcc   1260
agagagtgag agacattaac tcattagact ggaacttgaa ctgattcaca tctcattttt   1320
ccgtaaaaat gatttcagta gcacaagtta tttaaatctg tttttctaac tgggggaaaa   1380
gattcccacc caattcaaaa cattgtgcca tgtcaaacaa atagtctatc aaccccagac   1440
actggtttga agaatgttaa gacttgacag tggaactaca ttagtacaca gcaccagaat   1500
gtatattaag gtgtggcttt aggagcagtg ggagggtacc agcagaaagg ttagtatcat   1560
cagatagcat cttatacgag taatatgcct gctatttgaa gtgtaattga gaaggaaaat   1620
tttagcgtgc tcactgacct gcctgtagcc ccagtgacag ctaggatgtg cattctccag   1680
ccatcaagag actgagtcaa gttgttcctt aagtcagaac agcagactca gctctgacat   1740
tctgattcga atgacactgt tcaggaatcg gaatcctgtc gattagactg gacagcttgt   1800
ggcaagtgaa tttgcctgta caagccagat ttttttaaaa tttatattgt aaatattgtg   1860
tgtgtgtgtg tgtgtgtata tatatatata tgtacagtta tctaagttaa tttaaagttg   1920
tttgtgcctt tttatttttg tttttaatgc tttgatattt caatgttagc ctcaatttct   1980
gaacaccata ggtagaatgt aaagcttgtc tgatcgttca aagcatgaaa tggatactta   2040
tatgaaaatt ctgctcagat agaatgacag tccgtcaaaa cagattgttt gcaaagggga   2100
ggcatcagtg tccttggcag gctgattttct aggtaggaaa tgtggtagcc tcacttttaa   2160
tgaacaaatg gcctttatta aaaactgagt gactctatat agctgatcag ttttttcacc   2220
tggaagcatt tgtttctact ttgatatgac tgttttttcgg acagtttatt tgttgagagt   2280
gtgaccaaaa gttacatgtt tgcacctttc tagttgaaaa taaagtgtat attttttcta   2340
taaaaaaaaa aaaaaaaa                                                  2358
```

<210> SEQ ID NO 8
<211> LENGTH: 2695
<212> TYPE: DNA
<213> ORGANISM: Homo sapiens

<400> SEQUENCE: 8

| | | | | | |
|---|---|---|---|---|---|
| caaataaaag | cgatggcgat | tgggctgccg | cgtttggcgc | tcggtccggt | cgcgtccgac | 60 |
| acccggtggg | actcagaagg | cagtggagcc | ccggcggcgg | cggcggcggc | gcgcgggggc | 120 |
| gacgcgcggg | aacaacgcga | gtcggcgcgc | gggacgaaga | ataatcatgg | ccagactgg | 180 |
| gaagaaatct | gagaagggac | cagtttgttg | gcggaagcgt | gtaaaatcag | agtacatgcg | 240 |
| actgagacag | ctcaagaggt | tcagacgagc | tgatgaagta | aagagtatgt | ttagttccaa | 300 |
| tcgtcagaaa | attttggaaa | gaacggaaat | cttaaaccaa | gaatggaaac | agcgaaggat | 360 |
| acagcctgtg | cacatcctga | cttctgtgag | ctcattgcgc | gggactaggg | agtgttcggt | 420 |
| gaccagtgac | ttggattttc | caacacaagt | catcccatta | aagactctga | atgcagttgc | 480 |
| ttcagtaccc | ataatgtatt | cttggtctcc | cctacacag | aattttatgg | tggaagatga | 540 |
| aactgtttta | cataacattc | cttatatggg | agatgaagtt | ttagatcagg | atggtacttt | 600 |
| cattgaagaa | ctaataaaaa | attatgatgg | gaaagtacac | ggggatagag | aatgtgggtt | 660 |
| tataaatgat | gaatttttg | tggagttggt | gaatgccctt | ggtcaatata | atgatgatga | 720 |
| cgatgatgat | gatggagacg | atcctgaaga | aagagaagaa | aagcagaaag | atctggagga | 780 |
| tcaccgagat | gataaagaaa | gccgcccacc | tcggaaattt | ccttctgata | aaattttga | 840 |
| agccatttcc | tcaatgtttc | cagataaggg | cacagcagaa | gaactaaagg | aaaaatataa | 900 |
| agaactcacc | gaacagcagc | tcccaggcgc | acttcctcct | gaatgtaccc | ccaacataga | 960 |
| tggaccaaat | gctaaatctg | ttcagagaga | gcaaagctta | cactcctttc | atacgctttt | 1020 |
| ctgtaggcga | tgttttaaat | atgactgctt | cctacatcgt | aagtgcaatt | attcttttca | 1080 |
| tgcaacaccc | aacacttata | agcggaagaa | cacagaaaca | gctctagaca | caaaccttg | 1140 |
| tggaccacag | tgttaccagc | atttggaggg | agcaaaggag | tttgctgctg | ctctcaccgc | 1200 |
| tgagcggata | aagaccccac | caaaacgtcc | aggaggccgc | agaagaggac | ggcttcccaa | 1260 |
| taacagtagc | aggcccagca | ccccaccat | taatgtgctg | gaatcaaagg | atacagacag | 1320 |
| tgatagggaa | gcagggactg | aaacgggggg | agagaacaat | gataaagaag | aagaagagaa | 1380 |
| gaaagatgaa | acttcgagct | cctctgaagc | aaattctcgg | tgtcaaacac | caataaagat | 1440 |
| gaagccaaat | attgaacctc | ctgagaatgt | ggagtggagt | ggtgctgaag | cctcaatgtt | 1500 |
| tagagtcctc | attggcactt | actatgacaa | tttctgtgcc | attgctaggt | taattgggac | 1560 |
| caaaacatgt | agacaggtgt | atgagtttag | agtcaaagaa | tctagcatca | tagctccagc | 1620 |
| tcccgctgag | gatgtggata | tcctccaag | gaaaagaag | aggaaacacc | ggttgtgggc | 1680 |
| tgcacactgc | agaaagatac | agctgaaaaa | ggacggctcc | tctaaccatg | tttacaacta | 1740 |
| tcaaccctgt | gatcatccac | ggcagccttg | tgacagttcg | tgcccttgtg | tgatagcaca | 1800 |
| aaatttttgt | gaaaagtttt | gtcaatgtag | ttcagagtgt | caaaaccgct | ttccgggatg | 1860 |
| ccgctgcaaa | gcacagtgca | acaccaagca | gtgcccgtgc | tacctggctg | tccgagagtg | 1920 |
| tgaccctgac | ctctgtctta | cttgtggagc | cgctgaccat | tgggacagta | aaaatgtgtc | 1980 |
| ctgcaagaac | tgcagtattc | agcggggctc | caaaaagcat | ctattgctgg | caccatctga | 2040 |
| cgtggcaggc | tggggggattt | ttatcaaaga | tcctgtgcag | aaaaatgaat | tcatctcaga | 2100 |
| atactgtgga | gagattattt | ctcaagatga | agctgacaga | agagggaaag | tgtatgataa | 2160 |

```
atacatgtgc agctttctgt tcaacttgaa caatgatttt gtggtggatg caacccgcaa    2220
gggtaacaaa attcgttttg caaatcattc ggtaaatcca aactgctatg caaaagttat    2280
gatggttaac ggtgatcaca ggataggtat ttttgccaag agagccatcc agactggcga    2340
agagctgttt tttgattaca gatacagcca ggctgatgcc ctgaagtatg tcggcatcga    2400
aagagaaatg gaaatccctt gacatctgct acctcctccc ccctcctctg aaacagctgc    2460
cttagcttca ggaacctcga gtactgtggg caatttagaa aaagaacatg cagttgaaa    2520 ttctgaattt gcaaagtact gtaagaataa tttatagtaa tgagtttaaa aatcaacttt    2580
ttattgcctt ctcaccagct gcaaagtgtt ttgtaccagt gaattttgtgc aataatgcag    2640 tatggtacat ttttcaactt tgaataaaga atacttgaac ttgtcaaaaa aaaaa          2695
```

<210> SEQ ID NO 9
<211> LENGTH: 3352
<212> TYPE: DNA
<213> ORGANISM: Homo sapiens

<400> SEQUENCE: 9

```
ggggcgtggc gccggggatt gggagggctt cttgcaggct gctgggctgg ggctaagggc      60
tgctcagttt ccttcagcgg ggcactggga agcgccatgg cactgcaggg catctcggtc     120
gtggagctgt ccggcctggc cccgggcccg ttctgtgcta tggtcctggc tgacttcggg     180
gcgcgtgtgg tacgcgtgga ccggcccggc tcccgctacg acgtgagccg cttgggccgg     240
ggcaagcgct cgctagtgct ggacctgaag cagccgcggg gagccgccgt gctgcggcgt     300
ctgtgcaagc ggtcggatgt gctgctggag cccttccgcc gcggtgtcat ggagaaactc     360
cagctgggcc cagagattct gcagcgggaa aatccaaggc ttatttatgc caggctgagt     420
ggatttggcc agtcaggaag cttctgccgg ttagctggcc acgatatcaa ctatttggct     480
ttgtcaggtg ttctctcaaa aattggcaga agtggtgaga atccgtatgc cccgctgaat     540
ctcctggctg actttgctgg tggtggcctt atgtgtgcac tgggcattat aatggctctt     600
tttgaccgca cacgcactgg caagggtcag gtcattgatg caaatatggt ggaaggaaca     660
gcatatttaa gttctttttct gtggaaaact cagaaattga gtctgtggga agcacctcga     720
ggacagaaca tgttggatgg tggagcacct ttctatacga cttacaggac agcagatggg     780
gaattcatgg ctgttggagc aatagaaccc cagttctacg agctgctgat caaaggactt     840
ggactaaagt ctgatgaact tcccaatcag atgagcatgg atgattggcc agaaatgaag     900
aagaagtttg cagatgtatt tgcagagaag acgaaggcag agtggtgtca aatctttgac     960
ggcacagatg cctgtgtgac tccggttctg acttttgagg aggttgttca tcatgatcac    1020
aacaaggaac ggggctcgtt tatccaccagt gaggagcagg acgtgagccc ccgccctgca    1080
cctctgctgt taaacacccc agccatccct tctttcaaaa gggatccttt cataggagaa    1140
cacactgagg agatacttga agaatttgga ttcagccgcg aagagattta tcagcttaac    1200
tcagataaaa tcattgaaag taataaggta aaagctagtc tctaacttcc aggcccacgg    1260
ctcaagtgaa tttgaatact gcatttacag tgtagagtaa cacataacat tgtatgcatg    1320
gaaacatgga ggaacagtat tacagtgtcc taccactcta atcaagaaaa gaattacaga    1380
ctctgattct acagtgatga ttgaattcta aaaatggtta tcattagggc ttttgattta    1440
taaaactttg ggtacttata ctaaattatg gtagttattc tgccttccag tttgcttgat    1500
atatttgttg atattaagat tcttgactta tattttgaat gggttctagt gaaaaggaa     1560
```

```
tgatatattc ttgaagacat cgatatacat ttatttacac tcttgattct acaatgtaga   1620
aaatgaggaa atgccacaaa ttgtatggtg ataaaagtca cgtgaaacag agtgattggt   1680
tgcatccagg cctttgtct tggtgttcat gatctccctc taagcacatt ccaaacttta   1740
```

-continued

```
tataaacaag ggggttttct gggcctctcc aatattaagt tcaggccagg atctgtggtg     420
gtacaattga ctctggcctt ccgagaaggt accatcaatg tccacgacgt ggagacacag     480
ttcaatcagt ataaaacgga agcagcctct cgatataacc tgacgatctc agacgtcagc     540
gtgagtgatg tgccatttcc tttctctgcc cagtctgggg ctggggtgcc aggctggggc     600
atcgcgctgc tggtgctggt ctgtgttctg gttgcgctgg ccattgtcta tctcattgcc     660
ttggctgtct gtcagtgccg ccgaaagaac tacgggcagc tggacatctt ccagccccgg     720
gatacctacc atcctatgag cgagtacccc acctaccaca cccatgggcg ctatgtgccc     780
cctagcagta ccgatcgtag cccctatgag aaggtttctg caggtaatgg tggcagcagc     840
ctctcttaca caaacccagc agtggcagcc acttctgcca acttgtaggg gcacgtcgcc     900
cgctgagctg agtggccagc cagtgccatt ccactccact caggttcttc agggccagag     960
cccctgcacc ctgtttgggc tggtgagctg ggagttcagg tgggctgctc acagcctcct    1020
tcagaggccc caccaatttc tcggacactt ctcagtgtgt ggaagctcat gtgggcccct    1080
gagggctcat gcctgggaag tgttgtggtg ggggctccca ggaggactgg cccagagagc    1140
cctgagatag cggggatcct gaactggact gaataaaacg tggtctccca ctgcgccaaa    1200
aaaaaaaaa                                                            1209
```

<210> SEQ ID NO 11
<211> LENGTH: 291
<212> TYPE: PRT
<213> ORGANISM: Homo sapiens

<400> SEQUENCE: 11

```
Met Gln Arg Ala Arg Pro Thr Leu Trp Ala Ala Leu Thr Leu Leu
1               5                   10                  15

Val Leu Leu Arg Gly Pro Pro Val Ala Arg Ala Gly Ala Ser Ser Ala
                20                  25                  30

Gly Leu Gly Pro Val Val Arg Cys Glu Pro Cys Asp Ala Arg Ala Leu
            35                  40                  45

Ala Gln Cys Ala Pro Pro Ala Val Cys Ala Glu Leu Val Arg Glu
    50                  55                  60

Pro Gly Cys Gly Cys Cys Leu Thr Cys Ala Leu Ser Glu Gly Gln Pro
65                  70                  75                  80

Cys Gly Ile Tyr Thr Glu Arg Cys Gly Ser Gly Leu Arg Cys Gln Pro
                85                  90                  95

Ser Pro Asp Glu Ala Arg Pro Leu Gln Ala Leu Leu Asp Gly Arg Gly
            100                 105                 110

Leu Cys Val Asn Ala Ser Ala Val Ser Arg Leu Arg Ala Tyr Leu Leu
        115                 120                 125

Pro Ala Pro Pro Ala Pro Gly Asn Ala Ser Glu Ser Glu Glu Asp Arg
    130                 135                 140

Ser Ala Gly Ser Val Glu Ser Pro Ser Val Ser Ser Thr His Arg Val
145                 150                 155                 160

Ser Asp Pro Lys Phe His Pro Leu His Ser Lys Ile Ile Ile Lys
                165                 170                 175

Lys Gly His Ala Lys Asp Ser Gln Arg Tyr Lys Val Asp Tyr Glu Ser
            180                 185                 190

Gln Ser Thr Asp Thr Gln Asn Phe Ser Ser Glu Ser Lys Arg Glu Thr
        195                 200                 205

Glu Tyr Gly Pro Cys Arg Arg Glu Met Glu Asp Thr Leu Asn His Leu
```

```
                210                 215                 220
Lys Phe Leu Asn Val Leu Ser Pro Arg Gly Val His Ile Pro Asn Cys
225                 230                 235                 240

Asp Lys Lys Gly Phe Tyr Lys Lys Gln Cys Arg Pro Ser Lys Gly
                245                 250                 255

Arg Lys Arg Gly Phe Cys Trp Cys Val Asp Lys Tyr Gly Gln Pro Leu
                260                 265                 270

Pro Gly Tyr Thr Thr Lys Gly Lys Glu Asp Val His Cys Tyr Ser Met
            275                 280                 285

Gln Ser Lys
        290

<210> SEQ ID NO 12
<211> LENGTH: 295
<212> TYPE: PRT
<213> ORGANISM: Homo sapiens

<400> SEQUENCE: 12

Met Glu Thr Pro Ala Trp Pro Arg Val Pro Arg Pro Glu Thr Ala Val
1               5                   10                  15

Ala Arg Thr Leu Leu Leu Gly Trp Val Phe Ala Gln Val Ala Gly Ala
                20                  25                  30

Ser Gly Thr Thr Asn Thr Val Ala Ala Tyr Asn Leu Thr Trp Lys Ser
            35                  40                  45

Thr Asn Phe Lys Thr Ile Leu Glu Trp Glu Pro Lys Pro Val Asn Gln
50                  55                  60

Val Tyr Thr Val Gln Ile Ser Thr Lys Ser Gly Asp Trp Lys Ser Lys
65                  70                  75                  80

Cys Phe Tyr Thr Thr Asp Thr Glu Cys Asp Leu Thr Asp Glu Ile Val
                85                  90                  95

Lys Asp Val Lys Gln Thr Tyr Leu Ala Arg Val Phe Ser Tyr Pro Ala
                100                 105                 110

Gly Asn Val Glu Ser Thr Gly Ser Ala Gly Glu Pro Leu Tyr Glu Asn
            115                 120                 125

Ser Pro Glu Phe Thr Pro Tyr Leu Glu Thr Asn Leu Gly Gln Pro Thr
130                 135                 140

Ile Gln Ser Phe Glu Gln Val Gly Thr Lys Val Asn Val Thr Val Glu
145                 150                 155                 160

Asp Glu Arg Thr Leu Val Arg Arg Asn Asn Thr Phe Leu Ser Leu Arg
                165                 170                 175

Asp Val Phe Gly Lys Asp Leu Ile Tyr Thr Leu Tyr Tyr Trp Lys Ser
                180                 185                 190

Ser Ser Ser Gly Lys Lys Thr Ala Lys Thr Asn Thr Asn Glu Phe Leu
            195                 200                 205

Ile Asp Val Asp Lys Gly Glu Asn Tyr Cys Phe Ser Val Gln Ala Val
210                 215                 220

Ile Pro Ser Arg Thr Val Asn Arg Lys Ser Thr Asp Ser Pro Val Glu
225                 230                 235                 240

Cys Met Gly Gln Glu Lys Gly Glu Phe Arg Glu Ile Phe Tyr Ile Ile
                245                 250                 255

Gly Ala Val Val Phe Val Val Ile Ile Leu Val Ile Ile Leu Ala Ile
                260                 265                 270

Ser Leu His Lys Cys Arg Lys Ala Gly Val Gly Gln Ser Trp Lys Glu
            275                 280                 285
```

```
Asn Ser Pro Leu Asn Val Ser
    290             295

<210> SEQ ID NO 13
<211> LENGTH: 326
<212> TYPE: PRT
<213> ORGANISM: Homo sapiens

<400> SEQUENCE: 13

Met Ser Cys Ala Glu Val Met Tyr His Pro Gln Pro Tyr Gly Ala Ser
1               5                   10                  15

Gln Tyr Leu Pro Asn Pro Met Ala Ala Thr Thr Cys Pro Thr Ala Tyr
            20                  25                  30

Tyr Gln Pro Ala Pro Gln Pro Gly Gln Gln Lys Lys Leu Ala Val Phe
        35                  40                  45

Ser Lys Met Gln Asp Ser Leu Glu Val Thr Leu Pro Ser Lys Gln Glu
50                  55                  60

Glu Glu Asp Glu Glu Glu Glu Glu Lys Asp Gln Pro Ala Glu
65                  70                  75                  80

Met Glu Tyr Leu Asn Ser Arg Cys Val Leu Phe Thr Tyr Phe Gln Gly
                85                  90                  95

Asp Ile Gly Ser Val Val Asp Glu His Phe Ser Arg Ala Leu Gly Gln
            100                 105                 110

Ala Ile Thr Leu His Pro Glu Ser Ala Ile Ser Lys Ser Lys Met Gly
        115                 120                 125

Leu Thr Pro Leu Trp Arg Asp Ser Ser Ala Leu Ser Ser Gln Arg Asn
130                 135                 140

Ser Phe Pro Thr Ser Phe Trp Thr Ser Tyr Gln Pro Pro Ala
145                 150                 155                 160

Pro Cys Leu Gly Gly Val His Pro Asp Phe Gln Val Thr Gly Pro Pro
                165                 170                 175

Gly Thr Phe Ser Ala Ala Asp Pro Ser Pro Trp Pro Gly His Asn Leu
            180                 185                 190

His Gln Thr Gly Pro Ala Pro Pro Ala Val Ser Glu Ser Trp Pro
        195                 200                 205

Tyr Pro Leu Thr Ser Gln Val Ser Pro Ser Tyr Ser His Met His Asp
    210                 215                 220

Val Tyr Met Arg His His His Pro His Ala His Met His His Arg His
225                 230                 235                 240

Arg His His His His His His Pro Pro Ala Gly Ser Ala Leu Asp
                245                 250                 255

Pro Ser Tyr Gly Pro Leu Leu Met Pro Ser Val His Ala Ala Arg Ile
            260                 265                 270

Pro Ala Pro Gln Cys Asp Ile Thr Lys Thr Glu Pro Thr Thr Val Thr
        275                 280                 285

Ser Ala Thr Ser Ala Trp Ala Gly Ala Phe His Gly Thr Val Asp Ile
290                 295                 300

Val Pro Ser Val Gly Phe Asp Thr Gly Leu Gln His Gln Asp Lys Ser
305                 310                 315                 320

Lys Glu Ser Pro Trp Tyr
                325

<210> SEQ ID NO 14
<211> LENGTH: 403
<212> TYPE: PRT
<213> ORGANISM: Homo sapiens
```

<400> SEQUENCE: 14

```
Met Ala Ser Glu Leu Ala Met Ser Asn Ser Asp Leu Pro Thr Ser Pro
 1               5                  10                  15
Leu Ala Met Glu Tyr Val Asn Asp Phe Asp Leu Met Lys Phe Glu Val
             20                  25                  30
Lys Lys Glu Pro Val Glu Thr Asp Arg Ile Ile Ser Gln Cys Gly Arg
         35                  40                  45
Leu Ile Ala Gly Gly Ser Ser Ser Thr Pro Met Ser Thr Pro Cys
     50                  55                  60
Ser Ser Val Pro Pro Ser Pro Ser Phe Ser Ala Pro Ser Pro Gly Ser
 65                  70                  75                  80
Gly Ser Glu Gln Lys Ala His Leu Glu Asp Tyr Tyr Trp Met Thr Gly
                 85                  90                  95
Tyr Pro Gln Gln Leu Asn Pro Glu Ala Leu Gly Phe Ser Pro Glu Asp
            100                 105                 110
Ala Val Glu Ala Leu Ile Ser Asn Ser His Gln Leu Gln Gly Gly Phe
        115                 120                 125
Asp Gly Tyr Ala Arg Gly Ala Gln Gln Leu Ala Ala Ala Gly Ala
    130                 135                 140
Gly Ala Gly Ala Ser Leu Gly Gly Ser Gly Glu Glu Met Gly Pro Ala
145                 150                 155                 160
Ala Ala Val Val Ser Ala Val Ile Ala Ala Ala Ala Gln Ser Gly
                165                 170                 175
Ala Gly Pro His Tyr His His His His His Ala Ala Gly His His
            180                 185                 190
His His Pro Thr Ala Gly Ala Pro Gly Ala Gly Ser Ala Ala Ala
        195                 200                 205
Ser Ala Gly Gly Ala Gly Gly Ala Gly Gly Gly Pro Ala Ser Ala
    210                 215                 220
Gly Gly Gly Gly Gly Gly Gly Gly Gly Gly Gly Gly Ala Ala
225                 230                 235                 240
Gly Ala Gly Gly Ala Leu His Pro His His Ala Ala Gly Gly Leu His
                245                 250                 255
Phe Asp Asp Arg Phe Ser Asp Glu Gln Leu Val Thr Met Ser Val Arg
            260                 265                 270
Glu Leu Asn Arg Gln Leu Arg Gly Val Ser Lys Glu Glu Val Ile Arg
        275                 280                 285
Leu Lys Gln Lys Arg Arg Thr Leu Lys Asn Arg Gly Tyr Ala Gln Ser
    290                 295                 300
Cys Arg Phe Lys Arg Val Gln Gln Arg His Val Leu Glu Ser Glu Lys
305                 310                 315                 320
Asn Gln Leu Leu Gln Gln Val Asp His Leu Lys Gln Glu Ile Ser Arg
                325                 330                 335
Leu Val Arg Glu Arg Asp Ala Tyr Lys Glu Lys Tyr Glu Lys Leu Val
            340                 345                 350
Ser Ser Gly Phe Arg Glu Asn Gly Ser Ser Asp Asn Pro Ser Ser
        355                 360                 365
Pro Glu Phe Phe Ile Thr Glu Pro Thr Arg Lys Leu Glu Pro Ser Val
    370                 375                 380
Gly Tyr Ala Thr Phe Trp Lys Pro Gln His Arg Val Leu Thr Ser Val
385                 390                 395                 400
Phe Thr Lys
```

<210> SEQ ID NO 15
<211> LENGTH: 373
<212> TYPE: PRT
<213> ORGANISM: Homo sapiens

<400> SEQUENCE: 15

Met Ala Ser Glu Leu Ala Met Ser Asn Ser Asp Leu Pro Thr Ser Pro
1               5                   10                  15

Leu Ala Met Glu Tyr Val Asn Asp Phe Asp Leu Met Lys Phe Glu Val
            20                  25                  30

Lys Lys Glu Pro Val Glu Thr Asp Arg Ile Ile Ser Gln Cys Gly Arg
        35                  40                  45

Leu Ile Ala Gly Gly Ser Leu Ser Ser Thr Pro Met Ser Thr Pro Cys
50                  55                  60

Ser Ser Val Pro Pro Ser Pro Ser Phe Ser Ala Pro Ser Pro Gly Ser
65                  70                  75                  80

Gly Ser Glu Gln Lys Ala His Leu Glu Asp Tyr Tyr Trp Met Thr Gly
            85                  90                  95

Tyr Pro Gln Gln Leu Asn Pro Glu Ala Leu Gly Phe Ser Pro Glu Asp
            100                 105                 110

Ala Val Glu Ala Leu Ile Ser Asn Ser His Gln Leu Gln Gly Gly Phe
        115                 120                 125

Asp Gly Tyr Ala Arg Gly Ala Gln Gln Leu Ala Ala Ala Gly Ala
130                 135                 140

Gly Ala Gly Ala Ser Leu Gly Gly Ser Gly Glu Glu Met Gly Pro Ala
145                 150                 155                 160

Ala Ala Val Val Ser Ala Val Ile Ala Ala Ala Ala Gln Ser Gly
                165                 170                 175

Ala Gly Pro His Tyr His His His His His Ala Ala Gly His His
            180                 185                 190

His His Pro Thr Ala Gly Ala Pro Gly Ala Ala Gly Ser Ala Ala Ala
        195                 200                 205

Ser Ala Gly Gly Ala Gly Ala Gly Gly Gly Pro Ala Ser Ala
210                 215                 220

Gly Gly Gly Gly Gly Gly Gly Gly Gly Gly Gly Gly Ala Ala
225                 230                 235                 240

Gly Ala Gly Gly Ala Leu His Pro His His Ala Ala Gly Gly Leu His
                245                 250                 255

Phe Asp Asp Arg Phe Ser Asp Glu Gln Leu Val Thr Met Ser Val Arg
            260                 265                 270

Glu Leu Asn Arg Gln Leu Arg Gly Val Ser Lys Glu Glu Val Ile Arg
        275                 280                 285

Leu Lys Gln Lys Arg Arg Thr Leu Lys Asn Arg Gly Tyr Ala Gln Ser
290                 295                 300

Cys Arg Phe Lys Arg Val Gln Gln Arg His Val Leu Glu Ser Glu Lys
305                 310                 315                 320

Asn Gln Leu Leu Gln Gln Val Asp His Leu Lys Gln Glu Ile Ser Arg
            325                 330                 335

Leu Val Arg Glu Arg Asp Ala Tyr Lys Glu Lys Tyr Glu Lys Leu Val
            340                 345                 350

Ser Ser Gly Phe Arg Glu Asn Gly Ser Ser Ser Asp Asn Pro Ser Ser
        355                 360                 365

Pro Glu Phe Phe Met

370

<210> SEQ ID NO 16
<211> LENGTH: 359
<212> TYPE: PRT
<213> ORGANISM: Homo sapiens

<400> SEQUENCE: 16

Met Pro Ser Leu Leu Leu Phe Thr Ala Ala Leu Ser Ser Trp
1               5                   10                  15

Ala Gln Leu Leu Thr Asp Ala Asn Ser Trp Trp Ser Leu Ala Leu Asn
                20                  25                  30

Pro Val Gln Arg Pro Glu Met Phe Ile Ile Gly Ala Gln Pro Val Cys
            35                  40                  45

Ser Gln Leu Pro Gly Leu Ser Pro Gly Gln Arg Lys Leu Cys Gln Leu
        50                  55                  60

Tyr Gln Glu His Met Ala Tyr Ile Gly Glu Gly Ala Lys Thr Gly Ile
65                  70                  75                  80

Lys Glu Cys Gln His Gln Phe Arg Gln Arg Trp Asn Cys Ser Thr
                85                  90                  95

Ala Asp Asn Ala Ser Val Phe Gly Arg Val Met Gln Ile Gly Ser Arg
            100                 105                 110

Glu Thr Ala Phe Thr His Ala Val Ser Ala Ala Gly Val Val Asn Ala
        115                 120                 125

Ile Ser Arg Ala Cys Arg Glu Gly Glu Leu Ser Thr Cys Gly Cys Ser
        130                 135                 140

Arg Thr Ala Arg Pro Lys Asp Leu Pro Arg Asp Trp Leu Trp Gly Gly
145                 150                 155                 160

Cys Gly Asp Asn Val Glu Tyr Gly Tyr Arg Phe Ala Lys Glu Phe Val
                165                 170                 175

Asp Ala Arg Glu Arg Glu Lys Asn Phe Ala Lys Gly Ser Glu Glu Gln
            180                 185                 190

Gly Arg Val Leu Met Asn Leu Gln Asn Asn Glu Ala Gly Arg Arg Ala
        195                 200                 205

Val Tyr Lys Met Ala Asp Val Ala Cys Lys Cys His Gly Val Ser Gly
        210                 215                 220

Ser Cys Ser Leu Lys Thr Cys Trp Leu Gln Leu Ala Glu Phe Arg Lys
225                 230                 235                 240

Val Gly Asp Arg Leu Lys Glu Lys Tyr Asp Ser Ala Ala Met Arg
            245                 250                 255

Val Thr Arg Lys Gly Arg Leu Glu Leu Val Asn Ser Arg Phe Thr Gln
                260                 265                 270

Pro Thr Pro Glu Asp Leu Val Tyr Val Asp Pro Ser Pro Asp Tyr Cys
            275                 280                 285

Leu Arg Asn Glu Ser Thr Gly Ser Leu Gly Thr Gln Gly Arg Leu Cys
        290                 295                 300

Asn Lys Thr Ser Glu Gly Met Asp Gly Cys Glu Leu Met Cys Cys Gly
305                 310                 315                 320

Arg Gly Tyr Asn Gln Phe Lys Ser Val Gln Val Glu Arg Cys His Cys
            325                 330                 335

Lys Phe His Trp Cys Cys Phe Val Arg Cys Lys Lys Cys Thr Glu Ile
                340                 345                 350

Val Asp Gln Tyr Ile Cys Lys
            355

<210> SEQ ID NO 17
<211> LENGTH: 349
<212> TYPE: PRT
<213> ORGANISM: Homo sapiens

<400> SEQUENCE: 17

```
Met Thr Ala Ala Ser Met Gly Pro Val Arg Val Ala Phe Val Val Leu
1               5                   10                  15

Leu Ala Leu Cys Ser Arg Pro Ala Val Gly Gln Asn Cys Ser Gly Pro
            20                  25                  30

Cys Arg Cys Pro Asp Glu Pro Ala Pro Arg Cys Pro Ala Gly Val Ser
        35                  40                  45

Leu Val Leu Asp Gly Cys Gly Cys Cys Arg Val Cys Ala Lys Gln Leu
50                  55                  60

Gly Glu Leu Cys Thr Glu Arg Asp Pro Cys Asp Pro His Lys Gly Leu
65                  70                  75                  80

Phe Cys Asp Phe Gly Ser Pro Ala Asn Arg Lys Ile Gly Val Cys Thr
                85                  90                  95

Ala Lys Asp Gly Ala Pro Cys Ile Phe Gly Gly Thr Val Tyr Arg Ser
            100                 105                 110

Gly Glu Ser Phe Gln Ser Ser Cys Lys Tyr Gln Cys Thr Cys Leu Asp
        115                 120                 125

Gly Ala Val Gly Cys Met Pro Leu Cys Ser Met Asp Val Arg Leu Pro
130                 135                 140

Ser Pro Asp Cys Pro Phe Pro Arg Arg Val Lys Leu Pro Gly Lys Cys
145                 150                 155                 160

Cys Glu Glu Trp Val Cys Asp Glu Pro Lys Asp Gln Thr Val Val Gly
                165                 170                 175

Pro Ala Leu Ala Ala Tyr Arg Leu Glu Asp Thr Phe Gly Pro Asp Pro
            180                 185                 190

Thr Met Ile Arg Ala Asn Cys Leu Val Gln Thr Thr Glu Trp Ser Ala
        195                 200                 205

Cys Ser Lys Thr Cys Gly Met Gly Ile Ser Thr Arg Val Thr Asn Asp
210                 215                 220

Asn Ala Ser Cys Arg Leu Glu Lys Gln Ser Arg Leu Cys Met Val Arg
225                 230                 235                 240

Pro Cys Glu Ala Asp Leu Glu Glu Asn Ile Lys Lys Gly Lys Lys Cys
                245                 250                 255

Ile Arg Thr Pro Lys Ile Ser Lys Pro Ile Lys Phe Glu Leu Ser Gly
            260                 265                 270

Cys Thr Ser Met Lys Thr Tyr Arg Ala Lys Phe Cys Gly Val Cys Thr
        275                 280                 285

Asp Gly Arg Cys Cys Thr Pro His Arg Thr Thr Thr Leu Pro Val Glu
290                 295                 300

Phe Lys Cys Pro Asp Gly Glu Val Met Lys Lys Asn Met Met Phe Ile
305                 310                 315                 320

Lys Thr Cys Ala Cys His Tyr Asn Cys Pro Gly Asp Asn Asp Ile Phe
                325                 330                 335

Glu Ser Leu Tyr Tyr Arg Lys Met Tyr Gly Asp Met Ala
            340                 345
```

<210> SEQ ID NO 18
<211> LENGTH: 751
<212> TYPE: PRT
<213> ORGANISM: Homo sapiens

<400> SEQUENCE: 18

```
Met Gly Gln Thr Gly Lys Lys Ser Glu Lys Gly Pro Val Cys Trp Arg
1               5                   10                  15

Lys Arg Val Lys Ser Glu Tyr Met Arg Leu Arg Gln Leu Lys Arg Phe
            20                  25                  30

Arg Arg Ala Asp Glu Val Lys Ser Met Phe Ser Ser Asn Arg Gln Lys
        35                  40                  45

Ile Leu Glu Arg Thr Glu Ile Leu Asn Gln Glu Trp Lys Gln Arg Arg
50                  55                  60

Ile Gln Pro Val His Ile Leu Thr Ser Val Ser Ser Leu Arg Gly Thr
65                  70                  75                  80

Arg Glu Cys Ser Val Thr Ser Asp Leu Asp Phe Pro Thr Gln Val Ile
                85                  90                  95

Pro Leu Lys Thr Leu Asn Ala Val Ala Ser Val Pro Ile Met Tyr Ser
            100                 105                 110

Trp Ser Pro Leu Gln Gln Asn Phe Met Val Glu Asp Glu Thr Val Leu
        115                 120                 125

His Asn Ile Pro Tyr Met Gly Asp Glu Val Leu Asp Gln Asp Gly Thr
130                 135                 140

Phe Ile Glu Glu Leu Ile Lys Asn Tyr Asp Gly Lys Val His Gly Asp
145                 150                 155                 160

Arg Glu Cys Gly Phe Ile Asn Asp Glu Ile Phe Val Glu Leu Val Asn
                165                 170                 175

Ala Leu Gly Gln Tyr Asn Asp Asp Asp Asp Asp Gly Asp Asp
            180                 185                 190

Pro Glu Glu Arg Glu Glu Lys Gln Lys Asp Leu Glu Asp His Arg Asp
        195                 200                 205

Asp Lys Glu Ser Arg Pro Pro Arg Lys Phe Pro Ser Asp Lys Ile Phe
210                 215                 220

Glu Ala Ile Ser Ser Met Phe Pro Asp Lys Gly Thr Ala Glu Glu Leu
225                 230                 235                 240

Lys Glu Lys Tyr Lys Glu Leu Thr Glu Gln Gln Leu Pro Gly Ala Leu
                245                 250                 255

Pro Pro Glu Cys Thr Pro Asn Ile Asp Gly Pro Asn Ala Lys Ser Val
            260                 265                 270

Gln Arg Glu Gln Ser Leu His Ser Phe His Thr Leu Phe Cys Arg Arg
        275                 280                 285

Cys Phe Lys Tyr Asp Cys Phe Leu His Arg Lys Cys Asn Tyr Ser Phe
290                 295                 300

His Ala Thr Pro Asn Thr Tyr Lys Arg Lys Asn Thr Glu Thr Ala Leu
305                 310                 315                 320

Asp Asn Lys Pro Cys Gly Pro Gln Cys Tyr Gln His Leu Glu Gly Ala
                325                 330                 335

Lys Glu Phe Ala Ala Ala Leu Thr Ala Glu Arg Ile Lys Thr Pro Pro
            340                 345                 350

Lys Arg Pro Gly Gly Arg Arg Gly Arg Leu Pro Asn Asn Ser Ser
        355                 360                 365

Arg Pro Ser Thr Pro Thr Ile Asn Val Leu Glu Ser Lys Asp Thr Asp
370                 375                 380

Ser Asp Arg Glu Ala Gly Thr Glu Thr Gly Gly Glu Asn Asn Asp Lys
385                 390                 395                 400

Glu Glu Glu Glu Lys Lys Asp Glu Thr Ser Ser Ser Ser Glu Ala Asn
```

```
            405                 410                 415
Ser Arg Cys Gln Thr Pro Ile Lys Met Lys Pro Asn Ile Glu Pro Pro
        420                 425                 430

Glu Asn Val Glu Trp Ser Gly Ala Glu Ala Ser Met Phe Arg Val Leu
            435                 440                 445

Ile Gly Thr Tyr Tyr Asp Asn Phe Cys Ala Ile Ala Arg Leu Ile Gly
        450                 455                 460

Thr Lys Thr Cys Arg Gln Val Tyr Glu Phe Arg Val Lys Glu Ser Ser
465                 470                 475                 480

Ile Ile Ala Pro Ala Pro Ala Glu Asp Val Asp Thr Pro Pro Arg Lys
            485                 490                 495

Lys Lys Arg Lys His Arg Leu Trp Ala Ala His Cys Arg Lys Ile Gln
            500                 505                 510

Leu Lys Lys Asp Gly Ser Ser Asn His Val Tyr Asn Tyr Gln Pro Cys
        515                 520                 525

Asp His Pro Arg Gln Pro Cys Asp Ser Ser Cys Pro Cys Val Ile Ala
    530                 535                 540

Gln Asn Phe Cys Glu Lys Phe Cys Gln Cys Ser Ser Glu Cys Gln Asn
545                 550                 555                 560

Arg Phe Pro Gly Cys Arg Cys Lys Ala Gln Cys Asn Thr Lys Gln Cys
            565                 570                 575

Pro Cys Tyr Leu Ala Val Arg Glu Cys Asp Pro Asp Leu Cys Leu Thr
        580                 585                 590

Cys Gly Ala Ala Asp His Trp Asp Ser Lys Asn Val Ser Cys Lys Asn
            595                 600                 605

Cys Ser Ile Gln Arg Gly Ser Lys Lys His Leu Leu Leu Ala Pro Ser
        610                 615                 620

Asp Val Ala Gly Trp Gly Ile Phe Ile Lys Asp Pro Val Gln Lys Asn
625                 630                 635                 640

Glu Phe Ile Ser Glu Tyr Cys Gly Glu Ile Ile Ser Gln Asp Glu Ala
            645                 650                 655

Asp Arg Arg Gly Lys Val Tyr Asp Lys Tyr Met Cys Ser Phe Leu Phe
        660                 665                 670

Asn Leu Asn Asn Asp Phe Val Val Asp Ala Thr Arg Lys Gly Asn Lys
    675                 680                 685

Ile Arg Phe Ala Asn His Ser Val Asn Pro Asn Cys Tyr Ala Lys Val
        690                 695                 700

Met Met Val Asn Gly Asp His Arg Ile Gly Ile Phe Ala Lys Arg Ala
705                 710                 715                 720

Ile Gln Thr Gly Glu Glu Leu Phe Phe Asp Tyr Arg Tyr Ser Gln Ala
            725                 730                 735

Asp Ala Leu Lys Tyr Val Gly Ile Glu Arg Glu Met Glu Ile Pro
        740                 745                 750

<210> SEQ ID NO 19
<211> LENGTH: 382
<212> TYPE: PRT
<213> ORGANISM: Homo sapiens

<400> SEQUENCE: 19

Met Ala Leu Gln Gly Ile Ser Val Val Glu Leu Ser Gly Leu Ala Pro
1               5                   10                  15

Gly Pro Phe Cys Ala Met Val Leu Ala Asp Phe Gly Ala Arg Val Val
            20                  25                  30
```

Arg Val Asp Arg Pro Gly Ser Arg Tyr Asp Val Ser Arg Leu Gly Arg
                35                  40                  45

Gly Lys Arg Ser Leu Val Leu Asp Leu Lys Gln Pro Arg Gly Ala Ala
 50                  55                  60

Val Leu Arg Arg Leu Cys Lys Arg Ser Asp Val Leu Leu Glu Pro Phe
 65                  70                  75                  80

Arg Arg Gly Val Met Glu Lys Leu Gln Leu Gly Pro Glu Ile Leu Gln
                 85                  90                  95

Arg Glu Asn Pro Arg Leu Ile Tyr Ala Arg Leu Ser Gly Phe Gly Gln
                100                 105                 110

Ser Gly Ser Phe Cys Arg Leu Ala Gly His Asp Ile Asn Tyr Leu Ala
                115                 120                 125

Leu Ser Gly Val Leu Ser Lys Ile Gly Arg Ser Gly Glu Asn Pro Tyr
130                 135                 140

Ala Pro Leu Asn Leu Leu Ala Asp Phe Ala Gly Gly Leu Met Cys
145                 150                 155                 160

Ala Leu Gly Ile Ile Met Ala Leu Phe Asp Arg Thr Arg Thr Gly Lys
                165                 170                 175

Gly Gln Val Ile Asp Ala Asn Met Val Glu Gly Thr Ala Tyr Leu Ser
                180                 185                 190

Ser Phe Leu Trp Lys Thr Gln Lys Leu Ser Leu Trp Glu Ala Pro Arg
                195                 200                 205

Gly Gln Asn Met Leu Asp Gly Ala Pro Phe Tyr Thr Thr Tyr Arg
                210                 215                 220

Thr Ala Asp Gly Glu Phe Met Ala Val Gly Ala Ile Glu Pro Gln Phe
225                 230                 235                 240

Tyr Glu Leu Leu Ile Lys Gly Leu Gly Leu Lys Ser Asp Glu Leu Pro
                245                 250                 255

Asn Gln Met Ser Met Asp Asp Trp Pro Glu Met Lys Lys Lys Phe Ala
                260                 265                 270

Asp Val Phe Ala Glu Lys Thr Lys Ala Glu Trp Cys Gln Ile Phe Asp
                275                 280                 285

Gly Thr Asp Ala Cys Val Thr Pro Val Leu Thr Phe Glu Glu Val Val
290                 295                 300

His His Asp His Asn Lys Glu Arg Gly Ser Phe Ile Thr Ser Glu Glu
305                 310                 315                 320

Gln Asp Val Ser Pro Arg Pro Ala Pro Leu Leu Asn Thr Pro Ala
                325                 330                 335

Ile Pro Ser Phe Lys Arg Asp Pro Phe Ile Gly Glu His Thr Glu Glu
                340                 345                 350

Ile Leu Glu Glu Phe Gly Phe Ser Arg Glu Glu Ile Tyr Gln Leu Asn
                355                 360                 365

Ser Asp Lys Ile Ile Glu Ser Asn Lys Val Lys Ala Ser Leu
                370                 375                 380

<210> SEQ ID NO 20
<211> LENGTH: 273
<212> TYPE: PRT
<213> ORGANISM: Homo sapiens

<400> SEQUENCE: 20

Met Thr Pro Gly Thr Gln Ser Pro Phe Phe Leu Leu Leu Leu Leu Thr
 1               5                   10                  15

Val Leu Thr Val Val Thr Gly Ser Gly His Ala Ser Ser Thr Pro Gly
                 20                  25                  30

Gly Glu Lys Glu Thr Ser Ala Thr Gln Arg Ser Ser Val Pro Ser Ser
             35                  40                  45

Thr Glu Lys Asn Ala Leu Ser Thr Gly Val Ser Phe Phe Leu Ser
 50                  55                  60

Phe His Ile Ser Asn Leu Gln Phe Asn Ser Ser Leu Glu Asp Pro Ser
 65                  70                  75                  80

Thr Asp Tyr Tyr Gln Glu Leu Gln Arg Asp Ile Ser Glu Met Phe Leu
                 85                  90                  95

Gln Ile Tyr Lys Gln Gly Gly Phe Leu Gly Leu Ser Asn Ile Lys Phe
                100                 105                 110

Arg Pro Gly Ser Val Val Gln Leu Thr Leu Ala Phe Arg Glu Gly
             115                 120                 125

Thr Ile Asn Val His Asp Val Glu Thr Gln Phe Asn Gln Tyr Lys Thr
             130                 135                 140

Glu Ala Ala Ser Arg Tyr Asn Leu Thr Ile Ser Asp Val Ser Val Ser
145                 150                 155                 160

Asp Val Pro Phe Pro Phe Ser Ala Gln Ser Gly Ala Gly Val Pro Gly
                165                 170                 175

Trp Gly Ile Ala Leu Leu Val Leu Val Cys Val Leu Val Ala Leu Ala
             180                 185                 190

Ile Val Tyr Leu Ile Ala Leu Ala Val Cys Gln Cys Arg Arg Lys Asn
             195                 200                 205

Tyr Gly Gln Leu Asp Ile Phe Pro Ala Arg Asp Thr Tyr His Pro Met
             210                 215                 220

Ser Glu Tyr Pro Thr Tyr His Thr His Gly Arg Tyr Val Pro Pro Ser
225                 230                 235                 240

Ser Thr Asp Arg Ser Pro Tyr Glu Lys Val Ser Ala Gly Asn Gly Gly
                245                 250                 255

Ser Ser Leu Ser Tyr Thr Asn Pro Ala Val Ala Ala Thr Ser Ala Asn
             260                 265                 270

Leu

<210> SEQ ID NO 21
<211> LENGTH: 21
<212> TYPE: DNA
<213> ORGANISM: Artificial Sequence
<220> FEATURE:
<223> OTHER INFORMATION: Probe for qPCR

<400> SEQUENCE: 21
ctgctggagc ccttccgccg c                                              21

<210> SEQ ID NO 22
<211> LENGTH: 19
<212> TYPE: DNA
<213> ORGANISM: Artificial Sequence
<220> FEATURE:
<223> OTHER INFORMATION: Primer for qPCR

<400> SEQUENCE: 22
ctgtgcaagc ggtcggatg                                                 19

<210> SEQ ID NO 23
<211> LENGTH: 23
<212> TYPE: DNA
<213> ORGANISM: Artificial Sequence
<220> FEATURE:
<223> OTHER INFORMATION: Primer for qPCR

```
<400> SEQUENCE: 23
cactcagcct ggcataaata agc                                           23

<210> SEQ ID NO 24
<211> LENGTH: 26
<212> TYPE: DNA
<213> ORGANISM: Artificial Sequence
<220> FEATURE:
<223> OTHER INFORMATION: Probe for qPCR

<400> SEQUENCE: 24
tgtgtgacga gcccaaggac caaacc                                        26

<210> SEQ ID NO 25
<211> LENGTH: 20
<212> TYPE: DNA
<213> ORGANISM: Artificial Sequence
<220> FEATURE:
<223> OTHER INFORMATION: Primer for qPCR

<400> SEQUENCE: 25
ggaaatgctg cgaggagtgg                                               20

<210> SEQ ID NO 26
<211> LENGTH: 21
<212> TYPE: DNA
<213> ORGANISM: Artificial Sequence
<220> FEATURE:
<223> OTHER INFORMATION: Primer for qPCR

<400> SEQUENCE: 26
cgtgtcttcc agtcggtaag c                                             21

<210> SEQ ID NO 27
<211> LENGTH: 26
<212> TYPE: DNA
<213> ORGANISM: Artificial Sequence
<220> FEATURE:
<223> OTHER INFORMATION: Probe for qPCR

<400> SEQUENCE: 27
acacgcttcc gccaacaaac tggtcc                                        26

<210> SEQ ID NO 28
<211> LENGTH: 22
<212> TYPE: DNA
<213> ORGANISM: Artificial Sequence
<220> FEATURE:
<223> OTHER INFORMATION: Primer for qPCR

<400> SEQUENCE: 28
gcgggacgaa gaataatcat gg                                            22

<210> SEQ ID NO 29
<211> LENGTH: 22
<212> TYPE: DNA
<213> ORGANISM: Artificial Sequence
<220> FEATURE:
<223> OTHER INFORMATION: Primer for qPCR

<400> SEQUENCE: 29
tgtctcagtc gcatgtactc tg                                            22

<210> SEQ ID NO 30
```

```
<211> LENGTH: 29
<212> TYPE: DNA
<213> ORGANISM: Artificial Sequence
<220> FEATURE:
<223> OTHER INFORMATION: Probe for qPCR

<400> SEQUENCE: 30
acaacagaca cagagtgtga cctcaccga                                    29

<210> SEQ ID NO 31
<211> LENGTH: 25
<212> TYPE: DNA
<213> ORGANISM: Artificial Sequence
<220> FEATURE:
<223> OTHER INFORMATION: Primer for qPCR

<400> SEQUENCE: 31
agtcaggaga ttggaaaagc aaatg                                        25

<210> SEQ ID NO 32
<211> LENGTH: 19
<212> TYPE: DNA
<213> ORGANISM: Artificial Sequence
<220> FEATURE:
<223> OTHER INFORMATION: Primer for qPCR

<400> SEQUENCE: 32
ccgtgccaag tacgtctgc                                               19

<210> SEQ ID NO 33
<211> LENGTH: 28
<212> TYPE: DNA
<213> ORGANISM: Artificial Sequence
<220> FEATURE:
<223> OTHER INFORMATION: Probe for qPCR

<400> SEQUENCE: 33
acccagaact tctcctccga gtccaagc                                     28

<210> SEQ ID NO 34
<211> LENGTH: 22
<212> TYPE: DNA
<213> ORGANISM: Artificial Sequence
<220> FEATURE:
<223> OTHER INFORMATION: Primer for qPCR

<400> SEQUENCE: 34
gactacgagt ctcagagcac ag                                           22

<210> SEQ ID NO 35
<211> LENGTH: 22
<212> TYPE: DNA
<213> ORGANISM: Artificial Sequence
<220> FEATURE:
<223> OTHER INFORMATION: Primer for qPCR

<400> SEQUENCE: 35
ctctacggca gggaccatat tc                                           22

<210> SEQ ID NO 36
<211> LENGTH: 31
<212> TYPE: DNA
<213> ORGANISM: Artificial Sequence
<220> FEATURE:
<223> OTHER INFORMATION: Probe for qPCR

<400> SEQUENCE: 36
```
acagataccc agaacttctc ctccgagtcc a                    31

<210> SEQ ID NO 37
<211> LENGTH: 26
<212> TYPE: DNA
<213> ORGANISM: Artificial Sequence
<220> FEATURE:
<223> OTHER INFORMATION: Primer for qPCR

<400> SEQUENCE: 37
tacaaagttg actacgagtc tcagag                          26

<210> SEQ ID NO 38
<211> LENGTH: 24
<212> TYPE: DNA
<213> ORGANISM: Artificial Sequence
<220> FEATURE:
<223> OTHER INFORMATION: primer for qPCR

<400> SEQUENCE: 38
agtgtgtctt ccatttctct acgg                            24

<210> SEQ ID NO 39
<211> LENGTH: 30
<212> TYPE: DNA
<213> ORGANISM: Artificial Sequence
<220> FEATURE:
<223> OTHER INFORMATION: Probe for qPCR

<400> SEQUENCE: 39
ttttcataac tgagcccact cgcaagttgg                      30

<210> SEQ ID NO 40
<211> LENGTH: 19
<212> TYPE: DNA
<213> ORGANISM: Artificial Sequence
<220> FEATURE:
<223> OTHER INFORMATION: Primer for qPCR

<400> SEQUENCE: 40
agcgacaacc cgtcctctc                                  19

<210> SEQ ID NO 41
<211> LENGTH: 19
<212> TYPE: DNA
<213> ORGANISM: Artificial Sequence
<220> FEATURE:
<223> OTHER INFORMATION: Primer for qPCR

<400> SEQUENCE: 41
ggcgtatccc actgatggc                                  19

<210> SEQ ID NO 42
<211> LENGTH: 28
<212> TYPE: DNA
<213> ORGANISM: Artificial Sequence
<220> FEATURE:
<223> OTHER INFORMATION: Probe for qPCR

<400> SEQUENCE: 42
caatccatga gccagacacc cattccct                        28

<210> SEQ ID NO 43
<211> LENGTH: 20
<212> TYPE: DNA

<213> ORGANISM: Artificial Sequence
<220> FEATURE:
<223> OTHER INFORMATION: Primer for qPCR

<400> SEQUENCE: 43
tcgagtttgt ggtggtggtg                           20

<210> SEQ ID NO 44
<211> LENGTH: 28
<212> TYPE: DNA
<213> ORGANISM: Artificial Sequence
<220> FEATURE:
<223> OTHER INFORMATION: Primer for qPCR

<400> SEQUENCE: 44
ctagcaagtt atggagaatt tcagattg                  28

<210> SEQ ID NO 45
<211> LENGTH: 30
<212> TYPE: DNA
<213> ORGANISM: Artificial Sequence
<220> FEATURE:
<223> OTHER INFORMATION: Probe for qPCR

<400> SEQUENCE: 45
ttttcataac tgagcccact cgcaagttgg                30

<210> SEQ ID NO 46
<211> LENGTH: 19
<212> TYPE: DNA
<213> ORGANISM: Artificial Sequence
<220> FEATURE:
<223> OTHER INFORMATION: Primer for qPCR

<400> SEQUENCE: 46
agcgacaacc cgtcctctc                            19

<210> SEQ ID NO 47
<211> LENGTH: 19
<212> TYPE: DNA
<213> ORGANISM: Artificial Sequence
<220> FEATURE:
<223> OTHER INFORMATION: Primer for qPCR

<400> SEQUENCE: 47
ggcgtatccc actgatggc                            19

<210> SEQ ID NO 48
<211> LENGTH: 30
<212> TYPE: DNA
<213> ORGANISM: Artificial Sequence
<220> FEATURE:
<223> OTHER INFORMATION: Probe for qPCR

<400> SEQUENCE: 48
ttttcataac tgagcccact cgcaagttgg                30

<210> SEQ ID NO 49
<211> LENGTH: 19
<212> TYPE: DNA
<213> ORGANISM: Artificial Sequence
<220> FEATURE:
<223> OTHER INFORMATION: Primer for qPCR

<400> SEQUENCE: 49
agcgacaacc cgtcctctc                            19

<210> SEQ ID NO 50
<211> LENGTH: 19
<212> TYPE: DNA
<213> ORGANISM: Artificial Sequence
<220> FEATURE:
<223> OTHER INFORMATION: Primer for qPCR

<400> SEQUENCE: 50
ggcgtatccc actgatggc                                               19

<210> SEQ ID NO 51
<211> LENGTH: 25
<212> TYPE: DNA
<213> ORGANISM: Artificial Sequence
<220> FEATURE:
<223> OTHER INFORMATION: Probe for qPCR

<400> SEQUENCE: 51
cccctcccca cccatttcac cacca                                        25

<210> SEQ ID NO 52
<211> LENGTH: 21
<212> TYPE: DNA
<213> ORGANISM: Artificial Sequence
<220> FEATURE:
<223> OTHER INFORMATION: Primer for qPCR

<400> SEQUENCE: 52
cgcctgcctg aatctgttct g                                            21

<210> SEQ ID NO 53
<211> LENGTH: 22
<212> TYPE: DNA
<213> ORGANISM: Artificial Sequence
<220> FEATURE:
<223> OTHER INFORMATION: Primer for qPCR

<400> SEQUENCE: 53
ctgtaagcac tgtgaggagc ag                                           22

<210> SEQ ID NO 54
<211> LENGTH: 26
<212> TYPE: DNA
<213> ORGANISM: Artificial Sequence
<220> FEATURE:
<223> OTHER INFORMATION: Probe for qPCR

<400> SEQUENCE: 54
agacagctca gctctctcaa gccagc                                       26

<210> SEQ ID NO 55
<211> LENGTH: 21
<212> TYPE: DNA
<213> ORGANISM: Artificial Sequence
<220> FEATURE:
<223> OTHER INFORMATION: Primer for qPCR

<400> SEQUENCE: 55
aaagcaagat ggggctaacc c                                            21

<210> SEQ ID NO 56
<211> LENGTH: 26
<212> TYPE: DNA
<213> ORGANISM: Artificial Sequence
<220> FEATURE:

<223> OTHER INFORMATION: Primer for qPCR

<400> SEQUENCE: 56
tccaaaagga agttgggaaa ctattc                                          26

<210> SEQ ID NO 57
<211> LENGTH: 28
<212> TYPE: DNA
<213> ORGANISM: Artificial Sequence
<220> FEATURE:
<223> OTHER INFORMATION: Probe for qPCR

<400> SEQUENCE: 57
tgctgtagac ctgtatcgaa tcccacgc                                        28

<210> SEQ ID NO 58
<211> LENGTH: 23
<212> TYPE: DNA
<213> ORGANISM: Artificial Sequence
<220> FEATURE:
<223> OTHER INFORMATION: Primer for qPCR

<400> SEQUENCE: 58
tggagccttt catggaacag tag                                             23

<210> SEQ ID NO 59
<211> LENGTH: 24
<212> TYPE: DNA
<213> ORGANISM: Artificial Sequence
<220> FEATURE:
<223> OTHER INFORMATION: Primer for qPCR

<400> SEQUENCE: 59
taccacggtg attccttact cttg                                            24

<210> SEQ ID NO 60
<211> LENGTH: 29
<212> TYPE: DNA
<213> ORGANISM: Artificial Sequence
<220> FEATURE:
<223> OTHER INFORMATION: Probe for qPCR

<400> SEQUENCE: 60
ctgaataccg ctaacttctt ctgctggcc                                       29

<210> SEQ ID NO 61
<211> LENGTH: 20
<212> TYPE: DNA
<213> ORGANISM: Artificial Sequence
<220> FEATURE:
<223> OTHER INFORMATION: Primer for qPCR

<400> SEQUENCE: 61
ccccacagcc tactatcagc                                                 20

<210> SEQ ID NO 62
<211> LENGTH: 22
<212> TYPE: DNA
<213> ORGANISM: Artificial Sequence
<220> FEATURE:
<223> OTHER INFORMATION: Primer for qPCR

<400> SEQUENCE: 62
gacttccaga gagtcctgca tc                                              22

```
<210> SEQ ID NO 63
<211> LENGTH: 26
<212> TYPE: DNA
<213> ORGANISM: Artificial Sequence
<220> FEATURE:
<223> OTHER INFORMATION: Probe for qPCR

<400> SEQUENCE: 63
agacagctca gctctctcaa gccagc                                              26

<210> SEQ ID NO 64
<211> LENGTH: 21
<212> TYPE: DNA
<213> ORGANISM: Artificial Sequence
<220> FEATURE:
<223> OTHER INFORMATION: Primer for qPCR

<400> SEQUENCE: 64
aaagcaagat ggggctaacc c                                                   21

<210> SEQ ID NO 65
<211> LENGTH: 23
<212> TYPE: DNA
<213> ORGANISM: Artificial Sequence
<220> FEATURE:
<223> OTHER INFORMATION: Primer for qPCR

<400> SEQUENCE: 65
ggtccaaaag gaagttggga aac                                                 23

<210> SEQ ID NO 66
<211> LENGTH: 20
<212> TYPE: DNA
<213> ORGANISM: Artificial Sequence
<220> FEATURE:
<223> OTHER INFORMATION: Probe for qPCR

<400> SEQUENCE: 66
agccctgcga ccggcctcgt                                                     20

<210> SEQ ID NO 67
<211> LENGTH: 22
<212> TYPE: DNA
<213> ORGANISM: Artificial Sequence
<220> FEATURE:
<223> OTHER INFORMATION: Primer for qPCR

<400> SEQUENCE: 67
ggtgctcatg aacctgcaaa ac                                                  22

<210> SEQ ID NO 68
<211> LENGTH: 23
<212> TYPE: DNA
<213> ORGANISM: Artificial Sequence
<220> FEATURE:
<223> OTHER INFORMATION: Primer for qPCR

<400> SEQUENCE: 68
aggctacgtc tgccatctta tac                                                 23
```

MARKER GENES FOR PROSTATE CANCER CLASSIFICATION

CROSS-REFERENCE TO RELATED PATENT APPLICATIONS

This application is a continuation application of U.S. patent application Ser. No. 15/725,678, filed Oct. 5, 2017, which is a continuation application of U.S. patent application Ser. No. 14/352,107, filed Apr. 16, 2014 (U.S. Pat. No. 9,790,555), which is a national phase application of International Application No. PCT/EP2012/071077 filed on Oct. 24, 2012, which claims priority to Swedish Application No. 1150982-5 filed on Oct. 24, 2011. The contents of these earlier filed applications are hereby incorporated by reference in their entirety.

FIELD OF THE INVENTION

The present invention relates to the field of classification, prognostics and treatment of cancer, in particular of prostate cancer.

SEQUENCE LISTING

The Sequence Listing submitted herewith as a text file named "37441_0017U2_Sequence_Listing," created on Sep. 21, 2017, and having a size of 94,208 bytes is hereby incorporated by reference pursuant to 37 C.F.R. § 1.52(e)(5).

BACKGROUND OF THE INVENTION

Accurate prognosis and prediction of overall and cancer specific survival at the time of prostate cancer diagnosis are of utmost importance for the improvement of current status of personalized treatment choice between radical prostatectomy, radiation therapy, castration therapy and watchful waiting (Shariat et al, Cancer 2008, 113:3075-3099; Touijer et al, Cancer 2009, 115:3107-3111; Freedland, Cancer 2011, 117:1123-1153). Radical prostatectomy and curative radiation therapy for men with localized prostate cancer can reduce mortality and prolong lives for patients with aggressive cancer. On the other hand for patients with less aggressive cancer, that potentially need no radical or curative treatments at all, such therapies may cause unnecessary complications and side effects. For patients with less aggressive cancer watchful-waiting or active surveillance can be a suitable option. However, current prognostic and predictive methods based on common clinical parameters—including age at diagnosis, serum PSA level, Gleason score of biopsies and clinical stage—cannot accurately distinguish between less aggressive and aggressive cancers at localized stage. Nor can they identify what kind of cancer can still be effectively controlled by castration therapy when the disease becomes dangerous.

For patients whose cancers are already advanced at diagnosis or have relapsed after curative treatments chemical or surgical castration can palliate symptoms and slow down disease progression. Unfortunately, the effect and side effects of castration therapy show strong variation among patients. Some can live longer than five years with minimal side effects whereas others can die of castration resistant metastasis within three years or die of cardiovascular and other side effects of the castration treatment. Currently there are no methods that can predict what kind of patients would be benefit most from castration therapy.

A majority of prostate cancers progress so slowly that they can never reach the life-threatening stage, mainly due to old age and other competing diseases. However, a small proportion of prostate cancers progress very rapidly and kill patients in less than five years. At diagnosis, by conventional clinical parameters including age, tumor grade, Gleason score, clinical stage and comorbidity the prediction of cancer specific and overall survival can reach an accuracy up to 60-70%. Even patients with the same clinical prognostic parameters can show strong difference in survival as well as in response to treatment. Hence prostate cancer is a pathological (morphorlogical) diagnosis that may include several different biological subgroups or subtypes.

There is a need for a method that can distinguish these biological subgroups or subtypes of prostate cancer patients. There is also a need for a method that can classify these subtypes into aggressive or high risk tumors and less aggressive or low risk tumors, as well as a method that can predict survival of the patients with the respective subtype tumor. Furthermore, there is a need for a method that can be used for making a treatment decision for patients that have a tumor of the respective subtype, possibly also taking into account clinical parameters.

PRIOR ART

Patent document WO2008/013492 A1 discloses an approach for identifying embryonic stem cell related genes, denoted ES tumor predictor genes (ESTP genes), that may be important for cancer stem cell function. 641 ESTP genes were identified and found useful for classification of prostate cancer tumors.

Patent document WO09021338 A1 discloses a method for prognosis of a cancer, e.g. prostate cancer, in a subject by detecting a signature of splicing events. F3 is mentioned as one of many genes that may be used.

Patent document WO0171355 discloses the simultaneous analysis of PSA, IGF-I and IGFBP-3 in blood plasma to predict the risk for a man of getting prostate cancer.

US2003054419 A1 discloses a method for determining the risk of progression of a prostate cancer patient after therapy, wherein the levels of TGF-β1, IGFBP-2, or IGFBP-3 in plasma are measured.

Patent documents WO10006048 A and US2009298082 A disclose methods for predicting survivability of prostate cancer diagnosed patient and whether a subject with PSA recurrence will later develop systemic disease respectively. In both disclosures IGFBP3 is mentioned as one of many genes that may be used, together with other molecular markers.

Documents WO09105154 and WO06028867A disclose a method for determining a prognosis for an individual having cancer and a method of diagnosis for multiple myeloma. c-MAF is mentioned as one of many genes that may be used.

WO10101888A discloses a method for interfering with the activity of CTGF, wherein the activity of CTGF is associated with prostate cancer metastasis.

OBJECT OF THE INVENTION

It is an object of the present invention to provide molecular markers useful for classification, for prediction of prognosis and for guiding treatment decisions of prostate cancer in a subject.

It is another object of the present invention to provide new methods for classifying prostate cancer in a subject, as well as for using the classification for predicting prognosis of the subject and for making a treatment decision for the subject.

It is a further object of the present invention to provide a method of treating a subject having prostate cancer, based on the subject's tumor subtype.

It is still another object of the present invention to provide tools for classifying prostate cancers or tumors in a subject.

DISCLOSURE OF THE INVENTION

Identification of Genes and Gene Signatures that are Significantly Correlated to Survival in Prostate Cancer Subjects To support the biological subtype concept, previous studies using whole genome cDNA microarrays have classified breast cancer as well as prostate cancer into molecular subtypes with distinct clinical and pathological characteristics. The present disclosure further extends the concept and the importance. Instead of only using statistical analyses, the selection of candidate gene markers in the present study was driven by a cancer stem cell (CSC)/embryonic stem cell (ESC) hypothesis, aiming at effectively identifying just a few most important ESC/CSC gene markers. This approach was proven to be effective since the most significant predictive gene markers identified in the present study were from the list of identified embryonic stem cell gene predictors (ESCGPs).

The inventors hypothesized that prostate cancer's biological aggressiveness and responsiveness to castration therapy are mainly determined by major gene expression patterns in prostate cancer stem cells (CSCs) (Visvader, Nature 2011, 469:314-22; Ratajczak et al, Differentiation 2011, 81:153-161; Lang et al, J Pathol 2009, 217:299-306). It was also hypothesized that genes that have important functions in embryonic stem cells (ESCs) can also have importance in prostate CSCs. Thus, direct measurement of the expression patterns of ESC related genes in prostate cancer cells would reflect the biological aggressiveness of the cancer and enable prediction of the effect of castration therapy as well as prediction of patient survival.

Based on this hypothesis the inventors have previously identified genes, i.e. embryonic stem cell gene predictors (ESCGPs) that have a consistently high or consistently low levels of expression in ESC lines (WO 2008/013492 A1). Briefly, the ESCGPs were identified by analyzing previously published datasets of whole genome cDNA microarray data derived from 5 human ESC lines and 115 human normal tissues from different organs by use of a simple one-class SAM, whereby the genes were ranked in order according to their degree of consistency in expression levels in the ESCs. This was based on the concept that genes with either consistently high or consistently low expression levels in all ESC lines may have significant functions in maintaining ESC status and their expression changes in different patterns can lead to differentiation toward different directions. These ESC genes may also have functions in maintaining different status of CSCs and thus different expression patterns of ESC genes in CSCs may classify tumors into different subtypes with different biological aggressiveness and sensibility to different types of treatments. Starting from this list of ESCGPs the present study identified some important prognostic and predictive gene markers for prostate cancer.

From the list of 641 ESCGPs identified in WO 2008/013492 A1 a subset of 33 ESCGPs were selected in the present study, as candidates that may enable classification of prostate cancers using fewer ESCGPs. The candidates were selected according to three criteria as described in Example 2A (see also FIG. 1), i.e. according to their ranking position in the ESCGP list and according to their ranking positions gene lists from a previous study (Lapointe et al, Proc Natl Acad Sci USA 2004, 101:811-816) that identified genes that could potentially be used for classification of prostate cancer subtypes and genes that could distinguishing between prostate cancer and normal tissues.

Furthermore 5 genes that were not from the ESCGP list were selected according to a fourth criterion; they were reported and known to be important in prostate cancer. The reported genes were used as controls to evaluate the importance of the ECSGP genes in relation to non-ESCGP genes in the classification of prostate cancer. Furthermore they could potentially be included in a molecular marker signature for use in prostate cancer classification.

Expression of the 33 selected ESCGPs and 5 reported genes in three different prostate cancer cell lines was investigated by RT-PCR (see Example 2B). Of the 33 genes 24 genes (19 ESCGPs and 5 reported genes) were identified that had different expression patterns in the less aggressive cell line LNCap compared to in the aggressive cell lines DU145 and PC3 (see FIG. 2). These 24 genes were considered being more likely to be useful for tumor classification to distinguish between less aggressive and more aggressive cancers. Thus, the 24 genes (25 gene markers) were selected for the optimization of multiplex qPCR and evaluation of capability to classify prostate cancer in fine needle aspiration (FNA) samples from 189 prostate cancer patients with known clinical outcome (see Example 3A). Genes whose expression profile was correlated with survival were first identified by analysis in a training set, i.e. a subset of the full cohort of 189 patients. The ability of the identified significant genes to classify tumors was then confirmed by analysis in the complete patient cohort.

All patients in the present cohort had clinically significant prostate cancer and the majority (80%) of the patients were not treated by radical prostatectomy or full dose radiation therapy but only by castration therapy when the disease became advanced. Therefore, the survival data was not influenced by the cure effect of radical treatments, which when used at an early stage in some patients with biologically aggressive cancer could eliminate the cancer and thus the life threat. In the present cohort the time of follow up was 7-20 years and the majority (94.5%) of the patients were deceased, enabling a complete analysis of true overall survival time with minimal censored data. These characteristics ensured the discovery of new biomarkers for survival prediction and were unique as compared with most previous studies where PSA recurrence or progression free survival has been used as surrogate for overall and cancer specific survival.

In the present study both overall survival and cancer specific survival was used to evaluate the clinical value of prognostic biomarkers. Cancer specific survival is mainly determined by biological aggressiveness of cancer cells. However, the accuracy and importance of correlation between prognostic as well as predictive parameters (such as clinical parameters and/or expression of biomarkers) and cancer specific survival can be influenced by how cancer specific survival is defined, how the data is collected and how much data is censored due to other competing causes of mortality. On the other hand, overall survival is the survival data without any censoring by causes of death and including all causes of death. Therefore overall survival reflects not only biological aggressiveness of cancer cells but also many other factors such as competing disease or co-morbidities, complications as well as side effects of treatments, age and life expectancy. For prostate cancer patients overall survival may have more importance than cancer specific survival since most patients are diagnosed at old age and usually have other competing diseases such as cardiovascular diseases, diabetes mellitus or other malignant diseases (Daskivich et al, Cancer 2011, April 8. doi: 10.1002/cncr.26104. [Epub ahead of print]).

Ten molecular marker genes showed significant correlation with overall and/or cancer specific survival when analyzed by univariate analysis (see Table 1), and may be used for classification of prostate tumors, for prognosis prediction and also for making treatment decisions for patients depending on the classification of the patient's tumor. These were F3 (coagulation factor III), WNT5B (wingless-type MMTV integration site family, member 5B), VGLL3 (vestigial like 3 (*Drosophila*)), CTGF (connective tissue growth factor), IGFBP3 (insulin-like growth factor binding protein 3), c-MAF-a (long form of v-maf musculoaponeurotic fibrosarcoma oncogene homolog (avian)), c-MAF-b (short form of v-maf musculoaponeurotic fibrosarcoma oncogene homolog (avian)), AMACR (alpha-methylacyl-CoA racemase), MUC1 (mucin 1, cell surface associated) and EZH2 (enhancer of zeste homolog 2 (*Drosophila*)). Of these ten genes five (F3, WNT5B, CTGF, VGLL3 and IGFBP3) were ESCGPs identified from the list of genes with consistently high or low expression in embryonic stem cells. Two of the genes (c-MAF-a and c-MAF-b) were previously reported genes known to have important functions in myeloma.

Three of the significant genes (EZH2, AMACR and MUC1) are genes that have previously been reported in relation to prostate cancer. Several previous studies have identified biomarkers like AMACR, EZH2, MUC1 as well as AZGP1 and a stemness signature that are correlated to recurrence free survival after radical prostatectomy (Varambally et al, Nature 2002, 419:624-9; Rubin et al, JAMA 2002, 287:1662-70; Oon et al, Nat Rev Urol 2011, 8:131-8; Lapointe et al, Cancer Res 2007, 67:8504-10; Rubin et al, Cancer Epidemiol Biomarkers Prev

TABLE 1

Univariate Cox proportional hazards analysis of 25 ESCGPs and clinical parameters.

| | | Overall Survival | | Cancer Survival | |
|---|---|---|---|---|---|
| Variable | No. of Samples* | Hazard Ratio (95% CI) | P Value | Hazard Ratio (95% CI) | P Value |
| PSA > 50 vs. PSA ≤ 50 (ng/ml) | 161 | 2.34 (1.65-3.31) | <0.001 | 2.61 (1.68-4.05) | <0.001 |
| Tumor WHO Grade Poorly vs. Moderate/Well | 181 | 1.59 (1.16-2.18) | 0.004 | 1.94 (1.28-2.94) | 0.002 |
| Clinical Stage † Advanced vs. Localized | 175 | 1.70 (1.23-2.35) | 0.001 | 2.20 (1.44-3.38) | <0.001 |
| Age ‡ | 185 | 1.04 (1.02-1.06) | <0.001 | 1.03 (1.00-1.05) | 0.04 |
| PSA § | 161 | 1.00 (1.00-1.00) | 0.005 | 1.00 (1.00-1.00) | 0.004 |
| F3 ‖ | 92 | 1.11 (1.04-1.17) | 0.001 | 1.14 (1.06-1.22) | <0.001 |
| WNT5B ‖ | 89 | 1.14 (1.04-1.25) | 0.004 | 1.26 (1.11-1.42) | <0.001 |
| VGLL3 ‖ | 152 | 1.08 (1.03-1.13) | 0.002 | 1.07 (1.01-1.14) | 0.02 |
| c-MAF-a ‖ | 174 | 1.09 (1.03-1.17) | 0.007 | 1.09 (1.01-1.19) | 0.03 |
| CTGF ‖ | 100 | 1.13 (1.03-1.23) | 0.008 | 1.15 (1.02-1.29) | 0.02 |
| IGFBP3 ‖ | 169 | 1.04 (0.98-1.10) | 0.16 | 1.09 (1.01-1.17) | 0.02 |
| c-MAF-b ‖ | 69 | 1.13 (0.96-1.33) | 0.13 | 1.28 (1.04-1.57) | 0.02 |
| EZH2 ‖ | 144 | 0.94 (0.84-1.05) | 0.26 | 0.85 (0.74-0.98) | 0.02 |
| AMACR ‖ | 148 | 1.08 (1.02-1.16) | 0.01 | 1.08 (1.00-1.17) | 0.06 |
| MUC1 ‖ | 143 | 1.07 (1.00-1.13) | 0.04 | 1.06 (0.98-1.14) | 0.13 |
| WNT11 ‖ | 177 | 1.02 (0.97-1.08) | 0.38 | 1.02 (0.96-1.09) | 0.55 |
| BASP1 ‖ | 177 | 1.99 (0.93-1.06) | 0.87 | 0.97 (0.89-1.05) | 0.45 |
| AZGP1 ‖ | 148 | 0.99 (0.94-1.05) | 0.81 | 1.02 (0.96-1.08) | 0.55 |
| COL12A1 ‖ | 176 | 1.02 (0.98-1.07) | 0.34 | 0.97 (0.91-1.03) | 0.36 |
| EGR1 ‖ | 175 | 1.03 (0.95-1.11) | 0.47 | 1.07 (0.97-1.18) | 0.17 |
| LRRN1 ‖ | 182 | 1.02 (0.98-1.07) | 0.26 | 1.03 (0.98-1.09) | 0.29 |
| ERBB3 ‖ | 89 | 1.04 (0.98-1.10) | 0.23 | 1.04 (0.96-1.13) | 0.29 |
| CYR61 ‖ | 79 | 1.12 (0.99-1.27) | 0.07 | 1.08 (0.91-1.28) | 0.36 |
| FBP1 ‖ | 79 | 1.11 (1.00-1.23) | 0.06 | 1.08 (0.93-1.25) | 0.32 |
| PTN ‖ | 27 | 0.99 (0.79-1.24) | 0.93 | 1.02 (0.73-1.42) | 0.91 |
| LRP4 ‖ | 27 | 1.06 (0.90-1.24) | 0.47 | 1.11 (0.88-1.39) | 0.37 |
| THBS1 ‖ | 27 | 1.03 (0.91-1.17) | 0.66 | 1.02 (0.83-1.25) | 0.88 |
| GREM1 ‖ | 35 | 1.04 (0.94-1.16) | 0.40 | 1.12 (0.95-1.33) | 0.17 |
| METTL7A ‖ | 35 | 1.08 (0.91-1.28) | 0.37 | 0.95 (0.72-1.25) | 0.69 |
| CDH1 ‖ | 35 | 1.12 (0.96-1.30) | 0.14 | 0.94 (0.72-1.24) | 0.67 |

*Each ESCGP has its own number of samples due to not all of ESCGPs having been profiled across all samples.
† Clinical stage groups were classified using Tumor-Node-Metastasis (TNM) system and PSA value. Advanced clinical stage was defined as TNM stage any of T ≥3, N1, M1 or PSA >100.0 ng/ml. Localized clinical stage was defined as T1-2N0M0 and PSA ≤100.0 ng/ml.
‡ Age was modeled as a continuous variable. The hazard ratio is for each 1.0 year increase in age.
§ PSA value was modeled as a continuous variable. The hazard ratio is for each 1.0 ng/ml PSA increase in serum.
‖ Centered delta Ct value of gene was modeled as continuous variable. It is reversely corresponding to gene's expression level. The hazard ratio is for each increase of 1.0 unit in centered delta Ct value of gene.

2005, 14:1424-32; Strawbridge et al, Biomark Insights 2008, 3:303-15; Glinsky et al, J Clin Oncol 2008, 2846-53; Glinsky et al, J Clin Invest 2005, 115:1503-21). The present results show that the expression level of MUC1, AMACR and EZH2 in prostate cancer FNA samples is indeed correlated to either cancer specific or overall survival. However, of the previously reported gene markers only the correlation by c-MAF-a was as strong as the correlation by the ESCGPs F3, IGFBP3 and VGLL3 identified in the present study.

The expression levels (reversely correlated to the delta Ct value) of all these significant genes but EZH2 showed positive correlation with survival times (Table 1, Hazard ratio>1). Only the expression level of EZH2 in the FNA samples was reversely correlated with patient survival. This negative correlation of EZH2 was in agreement with its documented role as an oncogene. The present results of EZH2, AMACR, IGFBP3 and c-MAF-a genes are in line with relevant results of previous studies (Varambally et al, Nature 2002, 419:624-9; Rubin et al, Cancer Epidemiol Biomarkers Prev 2005, 14:1424-32; Mehta et al, Cancer Res 2011, 71:5154-63; Li et al, Genes Chromosomes Cancer 1999, 24:175-82). IGFBP3 has well proven function in suppressing the metastatic process of prostate cancer (Mehta et al, Cancer Res 2011, 71:5154-63).

The positive correlation with survival by MUC1 and F3 was unexpected. F3 and MUC1 have documented functions in promoting cancer development (Strawbridge et al, Biomark Insights 2008, 3:303-15; Kasthuri et al, J Clin Oncol 2009, 27:4834-8). The positive correlation with survival may indicate that prostate cancer cells with high expression level of F3 and MUC1 are strongly androgen dependent and sensitive to castration treatment (Strawbridge et al, Biomark Insights 2008, 3:303-15; Kasthuri et al, J Clin Oncol 2009, 27:4834-8; Mitchell et al, Neoplasia 2002, 4:9-18; Brodin et al, Semin Thromb Hemost 2001, 37:87-94). There are some prognostic and predictive markers with similar dual aspects in other cancers, such as HER-2/neu/ERBB2 amplification in breast cancer, where breast cancer with HER-2/neu/ERBB2 amplification has aggressive biological as well as clinical features but shows response to Tratsuzumab (Herceptin) treatment with resulting prolonged survival.

The function of VGLL3 in prostate cancer is still unknown.

Multivariate analysis was further made in order to identify genes that show correlation to survival independent of all clinical parameters (see Example 3A). Four genes (F3, IGFBP3, CTGF and AMACR) showed correlation to both overall and cancer specific survival independent of all clinical parameters (FIG. 4A-K). All the 4 genes but AMACR were from the list of ESCGPs. Two genes (WNT5B and EZH2) showed correlation to cancer specific survival independent of clinical parameters and one gene (VGLL3) showed correlation to overall survival independent of clinical parameters.

In order to study possible additive or synergic effects of multiple genes in the prediction of survival, different combinations of the ten significant genes in a series of unsupervised hierarchical clustering analyses were tested (see Example 3B and FIGS. 6-7). Importantly, two signatures were identified that could in a similar manner classify tumors into three subgroups or subtypes with significant difference in overall and cancer specific survival. The first ESCGP signature (Signature 1) includes the genes VGLL3, IGFBP3 and F3. The second ESCGP signature (Signature 2) includes the genes c-MAF-a, IGFBP3 and F3.

The classification had strong correlation to and could be used for the prediction of a patient's overall and cancer specific survival (see FIGS. 6-7 and Tables 2-3). This prognostic and predictive expression signature was independent of age, PSA level, tumor grade and clinical stage.

TABLE 2

Cox proportional hazards analysis of ESCGP signature 1 and clinical parameters (Univariate and Multivariate analysis).

| | | Overall Survival | | | | Cancer Survival | | | |
| --- | --- | --- | --- | --- | --- | --- | --- | --- | --- |
| | | Univariate Analysis | | Multivariate Analysis | | Univariate Analysis | | Multivariate Analysis | |
| Variable | No. of Samples* | Hazard Ratio (95% CI) | P Value | Hazard Ratio (95% CI) | P Value | Hazard Ratio (95% CI) | P Value | Hazard Ratio (95% CI) | P Value |
| ESCGP signature 1 † | | | | | | | | | |
| Group 1 vs. Group 3 | 87 | 5.86 (2.91-11.78) | <0001 | 4.77 (2.27-10.01) | <0.001 | 7.67 (3.04-19.36) | <0.001 | 7.12 (2.56-19.85) | <0.001 |
| Group 2 vs. Group 3 | 87 | 3.45 (1.79-6.66) | <0001 | 2.51 (1.21-5.21) | 0.01 | 3.99 (1.65-9.64) | 0.002 | 2.96 (1.11-7.87) | 0.03 |
| PSA >50 vs PSA ≤50 (ng/ml) | 87 | 2.93 (1.76-4.86) | <0.001 | 2.09 (1.10-3.94) | 0.02 | 3.33 (1.73-6.41) | <0.001 | 1.76 (0.77-4.03) | 0.18 |
| Tumor WHO Grade | | | | | | | | | |
| Poorly vs. Moderated/Well | 87 | 1.65 (1.03-2.66) | 0.04 | 1.17 (0.69-2.00) | 0.56 | 1.93 (1.04-3.57) | 0.04 | 1.20 (0.61-2.39) | 0.60 |
| Clinical Stage ‡ | | | | | | | | | |
| Advanced vs. Localized | 87 | 2.13 (1.32-3.45) | 0.002 | 1.68 (0.91-3.08) | 0.10 | 3.87 (1.94-7.70) | <0.001 | 3.62 (1.55-8.45) | 0.003 |
| Age § | 87 | 1.06 (1.03-1.09) | <0001 | 1.03 (1.00-1.06) | 0.05 | 1.06 (1.02-1.10) | 0.003 | 1.03 (0.99-1.08) | 0.11 |

*Number of samples for clustering analysis was 95. 87 samples had all clinical information including age at diagnosis, PSA value, tumor WHO grade and clinical stage. Univariate and Multivariate analysis was run across these 87 samples.
† ESCGP signature 1 included expression signature of VGLL3, IGFBP3 and F3. It classified samples into three tumor subtypes: Group 1, Group 2 and Group 3 by Cluster analysis (FIG. 6, panel A).
‡ Clinical stage groups were classified using Tumor-Node-Metastasis (TNM) system and PSA value. Advanced clinical stage was defined as TNM stage any of T ≥3, N1, M1 or PSA >100.0 ng/ml. Localized clinical stage was defined as T1-2N0M0 and PSA ≤100.0 ng/ml.
§ Age was modeled as a continuous variable. The hazard ratio is for each 1.0 year increase in age.

TABLE 3

Cox proportional hazards analysis of ESCGP signature 1 and clinical parameters (Univariate and Multivariate analysis).

| Variable | No. of Samples* | Overall Survival | | | | Cancer Survival | | | |
|---|---|---|---|---|---|---|---|---|---|
| | | Univariate Analysis | | Multivariate Analysis | | Univariate Analysis | | Multivariate Analysis | |
| | | Hazard Ratio (95% CI) | P Value | Hazard Ratio (95% CI) | P Value | Hazard Ratio (95% CI) | P Value | Hazard Ratio (95% CI) | P Value |
| ESCGPs signature 2 † | | | | | | | | | |
| Group 1 vs. Group 3 | 87 | 3.16 (1.71-5.81) | <0.001 | 2.46 (1.28-4.74) | 0.007 | 4.11 (1.84-9.19) | 0.001 | 3.71 (1.50-9.14] | 0.004 |
| Group 2 vs. Group 3 | 87 | 2.02 (1.09-377) | 0.03 | 1.38 (0.67-2.83) | 0.38 | 2.19 (0.95-5.05) | 0.07 | 1.72 (0.64-4.64) | 0.29 |
| PSA >50 vs PSA ≤50 (ng/ml) | 87 | 2.93 (1.76-4.86) | <0.001 | 1.89 (1.04-3.41) | 0.04 | 3.33 (1.73-6.41) | <0.001 | 1.71 (0.79-3.71) | 0.18 |
| Tumor WHO Grade | | | | | | | | | |
| Poorly vs. Moderated/Well | 87 | 1.65 (1.03-2.66) | 0.04 | 1.38 (0.83-2.28) | 0.21 | 1.93 (1.04-3.57) | 0.04 | 1.42 (0.74-2.73) | 0.29 |
| Clinical Stage ‡ | | | | | | | | | |
| Advanced vs. Localized | 87 | 2.13 (1.32-3.45) | 0.002 | 1.79 (1.02-3.14) | 0.04 | 3.87 (1.94-7.70) | <0.001 | 3.64 (1.67-7.91) | 0.001 |
| Age § | 87 | 1.06 (1.03-1.09) | <0.001 | 1.04 (1.01-1.08) | 0.02 | 1.06 (1.02-1.10) | 0.003 | 1.04 (0.99-1.08) | 0.09 |

*Number of samples for cluster analysis was 95. 87 samples had all clinical information including age at diagnosis, PSA value, tumor grade and clinical stage. Univariate and Multivariate analysis was run across these 87 samples.
† ESCGP signature 2 included expression signature of c-MAF-a, IGFBP3 and F3. It classified samples into three tumor subtypes: Group 1, Group 2 and Group 3 by cluster analysis (FIG. 7).
‡ Clinical stage groups were classified using Tumor-Node-Metastasis (TNM) system and PSA value. Advanced clinical stage was defined as TNM stage any of T ≥3, N1, M1 or PSA >100.0 ng/ml. Localized clinical stage was defined as T1-2N0M0 and PSA ≤100.0 ng/ml.
§ Age was modeled as a continuous variable. The hazard ratio is for each 1.0 year increase in age.

In addition the ability of the combination of genes IGFBP3 and F3 only (ESCGP signature 3) to classify tumor samples and predict survival was tested (see Example 3D). The tumor samples were first classified into three groups by use of unsupervised hierarchical clustering (FIG. 13). As determined by Cox proportional hazards analysis the classification had strong correlation to and could be used for the prediction of a patient's overall and cancer specific survival (see Tables 4-5).

TABLE 4

Cox proportional hazards analysis of ESCGP signature 3 and F3 (Univariate and Multivariate analysis).

| Variables | No. of Samples* | Overall Survival | | | | Cancer Survival | | | |
|---|---|---|---|---|---|---|---|---|---|
| | | Univariate Analysis | | Multivariate Analysis | | Univariate Analysis | | Multivariate Analysis | |
| | | Hazard Ratio (95% CI) | P Value | Hazard Ratio (95% CI) | P Value | Hazard Ratio (95% CI) | P Value | Hazard Ratio (95% CI) | P Value |
| ESCGPs signature 3 † | | | | | | | | | |
| Group 1 vs. Group 3 | 92 | 3.09 (1.75-5.48) | <0.001 | 2.24 0.97-5.21) | 0.060 | 4.33 (2.00-9.39) | <0.001 | 2.93 (0.98-8.75) | 0.054 |
| Group 2 vs. Group 3 | 92 | 213 (1.09-4.16) | 0.026 | 2.09 (1.07-4.08) | 0.031 | 2.30 (0.90-5.86) | 0.081 | 2.25 (0.88-5.73) | 0.090 |
| F3 ‡ | 92 | 1.11 (1.04-1.17) | 0.001 | 1.05 (0.96-1.15) | 0.305 | 1.14 (1.06-1 22) | <0.001 | 1.06 (0.94-1.20) | 0.317 |

*92 out of the 95 clustered samples had both gene expression and survival data. Univariate and Multivariate analyses included these 92 samples.
† ESCGP signature 3 included the expression signature of IGFBP3 and F3, and classified samples into three tumor subtypes (Group 1. Group 2 and Group 3) by Cluster analysis (FIG. 13). It was modeled as a non-continuous variable with three categories according to the tumor subtype.
‡ The centered delta Ct value for gene expression was modeled as a continuous variable. It is inversely corresponding to gene's expression level. The hazard ratio is for each increase of 1.0 unit in centered delta Ct value.

TABLE 5

Cox proportional hazards analysis of ESCGP signature 3 and IGFBP3 [Univariate and Multivariate analysis].

| | | Overall Survival | | | | Cancer Survival | | | |
|---|---|---|---|---|---|---|---|---|---|
| | | Univariate Analysis | | Multivariate Analysis | | Univariate Analysis | | Multivariate Analysis | |
| Variables | No. of Samples* | Hazard Ratio (95% CI) | P Value | Hazard Ratio (95% CI) | P Value | Hazard Ratio (95% CI) | P Value | Hazard Ratio (95% CI) | P Value |
| | | | | ESCGP signature 3 ‡ | | | | | |
| Group 1 vs. Group 3 | 90 | 2.86 (1.62-5.07) | <0.001 | 2.53 (1.23-5.21) | 0.012 | 4.00 (1.84-8.66) | <0.001 | 3.15 (1.20-8.26) | 0.019 |
| Group 2 vs. Group 3 | 90 | 1.97 (1.01-3.83) | 0.047 | 1.69 (0.71-4.00) | 0.236 | 2.12 (0.83-5.39) | 0.116 | 1.58 (0.49-5.06) | 0.442 |
| IGFBP3 ‡ | 90 | 1.11 (1.03-1.20) | 0.007 | 1.03 (0.92-1.15) | 0.582 | 1.15 (1.04-1.27) | 0.007 | 1.06 (0.92-1.21) | 0.409 |

*90 out of the 95 clustered samples had both gene expression and survival data. Univariate and Multivariate analyses included these 90 samples.
† ESCGP signature 3 included the expression signature of IGFBP3 and F3, and classified samples into three tumor subtypes (Group 1, Group 2 and Group 3) by Cluster analysis (FIG. 13). It was modeled as a non-continuous variable with three categories according to the tumor subtype.
‡ The centered delta Ct value for gene expression was modeled as a continuous variable It is inversely corresponding to gene's expression level. The hazard ratio is for each increase of 1.0 unit in centered delta Ct value.

Most important marker genes found in this study showed correlation to both overall and cancer specific survivals. This was partly due to the possibility that prostate cancer or side effects of the treatments contributed also to deaths directly caused by other diseases. This could also partly be due to the fact that the ESCGP signature could be shared by both cancer stem cells and certain type of normal stem cells in the body. Thus, the ESCGP signature may have importance in the development of both cancer and other diseases. For instance, IGFBP3 has been identified with important suppressive functions in both cancer and diabetes (Yeap et al, Eur J Endocrinol 2011, 164:715-23; Mehta et al, Cancer Res 2011, 71:5451-63).

Embodiments of the Present Invention

In a first aspect, the present invention provides a method of classifying prostate cancer in a subject, comprising:
a) determining a gene expression level, of the genes F3 and IGFBP3 in a sample from the subject, in other words determining the gene expression pattern of said genes;
b) classifying the tumor by comparing the gene expression level, i.e. gene expression pattern, determined in a) with a reference gene expression of the same genes in reference patients known to have a high risk or low risk tumor respectively; and
c) concluding that if the gene expression level/gene expression pattern determined in a) matches the reference gene expression of the reference patients with a high risk tumor, the tumor in the subject is a high risk tumor, and that if the gene expression level determined in a) matches the reference gene expression of the reference patients with a low risk tumor, the tumor in the subject is a low risk tumor.

In a preferred embodiment the expression level of the genes F3 and IGFBP3 and either of VGLL3 and c-MAF are determined in step a) and thus used for classification of the tumor. Preferably the expression level of F3, IGFBP3 and VGLL3 is determined.

These gene signatures have been shown particularly useful for the classification of prostate cancer tumors (FIGS. 6-7) and the resulting classification has been shown to be significantly correlated to survival in prostate cancer patients (FIGS. 6 and 9-12, Tables 2 and 3).

In one embodiment step a) thus further comprises determining a gene expression level of one or more of the genes VGLL3 and c-MAF, preferably VGLL3.

In a further embodiment step a) also comprises determining a gene expression level for one or more of the genes WNT5B and CTGF, EZH2, AMACR and MUC1.

In a second aspect, the present invention provides a method of classifying prostate cancer in a subject, comprising the steps of:
a) determining a gene expression level of at least one gene selected from F3, IGFBP3, VGLL3, c-MAF, WNT5B and/or CTGF in a sample from the subject;
b) classifying the tumor by comparing the gene expression level determined in a) with a reference gene expression of the same gene(s) in reference patients known to have a high risk or low risk tumor respectively; and
c) concluding that if the gene expression level determined in a) matches the reference gene expression of the reference patients with a high risk tumor, the tumor in the subject is a high risk tumor, and that if the gene expression level determined in a) matches the reference gene expression of the reference patients with a low risk tumor, the tumor in the subject is a low risk tumor.

This second aspect of the invention is based on the herein recognized fact that expression of any of F3, IGFBP3, VGLL3, c-MAF, WNT5B and CTGF in samples from subjects having prostate cancer may serve as an indicator of disease status in said subject. The inventors have found that there is a positive correlation between the gene expression levels of any of said genes and survival. More particularly, the inventors of the present invention have found a correlation between a high level of expression of any of F3, IGFBP3, VGLL3, c-MAF, WNT5B and CTGF and longer survival, thus low risk tumors. On the other hand a low level of expression of either of said genes is correlated with shorter survival and thus high risk tumors.

In one embodiment of this second aspect the expression level of at least two, such as two, three or four of the genes F3, IGFBP3, VGLL3, c-MAF, WNT5B and CTGF is determined in step a) of the method according to the present invention and thus used for classification of the tumor.

In a further embodiment the expression level of all of the genes F3, IGFBP3, VGLL3, c-MAF, WNT5B and CTGF is determined in step a) of the method according to the present invention and thus used for classification of the tumor.

In still another embodiment the expression level is also, that is in addition to any of the combinations above, determined for at least one of the genes EZH2, AMACR and MUC1 and thus used in the classification.

Whether the expression level of one of said genes in a patient with prostate cancer is high or low can be determined by comparing the gene expression level in a sample from the patient with a reference gene expression value of the same gene(s) in a reference patient, or group of reference patients, known to have a high risk or low risk tumor respectively. If the expression level of the selected gene(s) in the patient sample is as high as or higher than the expression level of the same gene in a reference patient known to have a low risk tumor the tumor of the subject may be classified as being low risk. If the expression level of the selected gene(s) in the patient sample is as low as or lower than the expression level of the same gene in a reference patient known to have a high risk tumor the tumor of the subject may be classified as being high risk. When a group of reference patients is used for the comparison, the medium or median expression level of the selected gene(s) in the group may be used as the reference gene expression value.

By matching the gene expression level of the selected gene with the reference gene expression of a reference patient is meant, when the gene expression level is determined for one gene, that when the expression level of the selected gene is as high as or higher than the reference gene expression in a reference patient known to have a low risk tumor the gene expression level matches that reference gene expression. Likewise, when the expression level of the selected gene is as low as or lower than the reference gene expression in a reference patient known to have a high risk tumor the gene expression level matches that reference gene expression.

By matching the gene expression level of the selected gene with the reference gene expression of a reference patient is meant, when the gene expression level is determined for two or more genes, that the overall gene expression pattern of the two or more selected genes must match with the overall reference gene expression pattern of the two or more selected genes in a reference patient. Thus the expression of both or all of the selected genes, as evaluated one by one, need not completely match the reference gene expression of the selected genes one by one. Rather a very high level of gene expression for one of the genes may compensate for a lower level of the other gene(s) and the expression pattern would still be considered matching. By gene expression pattern is meant the gene expression level for the genes in a selection of two or more genes.

Matching of gene expression profiles obtained from the subject and the reference patient respectively may for instance be made using hierarchical clustering using the gene expression data from both the subject and the reference samples, by way of methods that are known in the art (see e.g. Eisen et al, Proc Natl Acad Sci USA 1998, 95:14863-8). Clustering methods are suitable for evaluating trends in large data sets. Unsupervised clustering like hierarchical clustering is advantageously used to detect groups or classes in data sets that would not easily be recognized by just browsing the data. If the patient whose tumor is to be classified is clustered or grouped together with reference patients that are known have a low risk tumor then the tumor of the patient is also classified as a low risk tumor. If the patient whose tumor is to be classified is clustered or grouped together with reference patients that are known have a high risk tumor then the tumor of the patient is also classified as a high risk tumor.

By a high risk tumor is meant that the tumor subtype, as determined by use of a group of patients with known tumor subtype and known survival, is associated with shorter overall and/or cancer specific survival time than a low risk tumor. The subtype may for instance be defined as a tumor subtype with certain clinical parameters or with certain expression of certain genes. When determining whether there is a significant difference in survival time between patients with known subtypes and known survival times one may use calculation of hazard ratios which is well known in the art (Cox D R, J Royal Statist Soc B 1972, 34:187-220). A hazard in a group is the rate at which events, such as death, happens. The hazard in one group is assumed to be a constant proportion of the hazard in the other group. This proportion is the hazard ratio. Thus, if the hazard ratio is, with significance, higher or lower than one there is a higher risk for one group over the other.

The classification of the tumor may also include more classes than high risk and low risk such as one or more intermediate risk group(s).

The sample from the subject may be a tumor sample, such as a tumor sample obtained by fine needle aspiration (FNA), needle biopsy or by surgery. Alternatively the sample may be a blood sample, plasma, serum, cerebral fluid, urine, semen, exudate or a stool sample obtained from the subject. In particular, the gene expression level for IGFBP3 and F3 may advantageously be determined by analysis of a blood sample.

In one embodiment the gene expression level of the selected genes is determined by quantifying the amount of RNA or mRNA expressed from the genes. The amount of RNA or mRNA may for instance be determined by use of a method selected from microarray technology, Northern blotting and quantitative PCR (qPCR), such as real time quantitative PCR (qrt-PCR), optionally multiplex PCR, or any other method for measurement of gene expression known in the art.

For instance, the inventors have in the present study developed a simple multiplex quantitative PCR (qPCR) method to measure expression levels of several selected marker genes in prostate fine needle aspiration (FNA) samples. The developed method may also be used to measure expression levels in any tumor or blood sample taken from the patient.

One important technical advantage of this approach is that although the marker genes of the present invention are identified through a stem cell approach and are believed to be important for cancer stem cell function one does not need to directly isolate the CSCs from the tumor samples. The simple and robust multiplex qPCR method established in the present study can be directly applied to analyze fresh samples from routine needle biopsy or aspiration cytology for the prediction of survival and effect of castration therapy at the time of diagnosis. All samples analyzed in the present study were fresh-frozen cytological cell spreads that would ensure isolation of pure cancer cell RNAs of high quality for qPCR analysis. However, the RNA isolation was not successful in some cases due to too few cells on the glass slides of FNA cytology spreads. The problem can be easily solved in the future clinical application by directly using fresh FNA cell suspensions or microdissected tumor samples from the needle biopsies for RNA isolation.

Since the marker genes of the present invention (F3, IGFBP3, VGLL3, c-MAF, WNT5B and CTGF) encode proteins it is also possible to use immunochemistry or other protein analytical methods to measure their protein expression as an estimate or function of their gene expression. Thus in one embodiment of the present invention the gene expression level may be indirectly determined by measuring the amount of protein encoded by said genes. The amount of protein may for instance be determined by use of methods such as immunohistochemistry, Western blotting, enzyme immunoassays such as ELISA, RIA and mass spectrometry, as well as other methods for protein detection known in the art.

The skilled person will recognize that the usefulness of the present invention is not limited to the quantification of gene expression of any particular variant of the marker genes of the present invention. As non-limiting examples, the marker genes may have coding sequences and amino acid sequences as specified in Table 6. In some embodiments they have cDNA sequences or amino acid sequences that are at least 85% identical or similar to the listed sequences, such as at least 90%, 91%, 92%, 93%, 94%, 95%, 96%, 97%, 98% or at least 99% identical or similar to the sequences listed in Table 6.

TABLE 6

| Gene | Full name | Gene/coding sequence SEQ ID NO: | Protein sequence SEQ ID NO: |
| --- | --- | --- | --- |
| IGFBP3 | insulin-like growth factor binding protein 3 | 1 | 11 |
| F3 | coagulation factor III | 2 | 12 |
| VGLL3 | vestigial like 3 (*Drosophila*) | 3 | 13 |
| c-MAF-a | long form of v-maf musculoaponeurotic fibrosarcoma oncogene homolog (avian) | 4 | 14 |
| c-MAF-b | short form of v-maf musculoaponeurotic fibrosarcoma oncogene homolog (avian) | 5 | 15 |
| WNT5B | wingless-type MMTV integration site family, member 5B | 6 | 16 |
| CTGF | connective tissue growth factor | 7 | 17 |
| EZH2 | enhancer of zeste homolog 2 (*Drosophila*) | 8 | 18 |
| AMACR | alpha-methylacyl-CoA racemase | 9 | 19 |
| MUC1 | mucin 1, cell surface associated | 10 | 20 |

The term "% identity", as used throughout the specification, is calculated as follows. The query sequence is aligned to the target sequence using the CLUSTAL W algorithm (Thompson, J. D., Higgins, D. G. and Gibson, T. J., Nucleic Acids Research, 22: 4673-4680 (1994)). A comparison is made over the window corresponding to the shortest of the aligned sequences. The shortest of the aligned sequences may in some instances be the target sequence. In other instances, the query sequence may constitute the shortest of the aligned sequences. The amino acid residues at each position are compared, and the percentage of positions in the query sequence that have identical correspondences in the target sequence is reported as % identity.

The term "% similarity", as used throughout the specification, is calculated in the following way. Sequence alignment and comparison are basically performed as described in relation to the % identity calculation. "Similarity" should however be interpreted as follows. Two amino acid residues are considered similar if they belong to the same group of amino acid residues. Non-limiting examples of groups of amino acid residues are the hydrophobic group, comprising the amino acid residues Ala, Val, Phe, Pro, Leu, Ile, Trp, Met and Cys; the basic group, comprising the amino acid residues Lys, Arg and His; the acidic group, comprising the amino acid residues Glu and Asp; the hydrophilic group, comprising the uncharged amino acid residues Gln, Asn, Ser, Thr and Tyr; and the natural group, comprising the amino acid residue Gly. Thus, the amino acid residues at each position are compared, and the percentage of positions in the query sequence that have similar correspondences in the target sequence is reported as % similarity.

The method for classifying a tumor in a subject having prostate cancer according to the present invention may have many benefits. For example, as in one embodiment of the invention, it may be used to predict survival for said subject. For a subject with a tumor that is classified to be a low risk tumor it is indicated that the subject has a good prognosis, while for a subject with a tumor that is classified to be a high risk tumor it is indicated that the subject has a poor prognosis.

A poor prognosis for a subject may mean that the subject has a decreased likelihood of survival or decrease in time of survival compared to a subject that has been predicted to have a good prognosis. A poor prognosis may also mean that the patient has an increased risk of recurrence or metastasis as compared to a patient with a good prognosis. For example, the likelihood of five-year survival for a patient with a low risk tumor may be 90% or lower, such as 85%, 80%, 75%, 70%, 60% or lower, while the likelihood of five-year survival in the high risk group may be 50% or lower, such as 45%, 40%, 30%, 20%, 10% or lower. The median length of survival for patients with low risk tumors may likewise be 6 years or longer, such as 7 years, 8 years, 9 years, 10 years or longer, while the median length of survival in patients with high risk tumors may be 5 years or shorter, such as 4 years, 3 years, 2 years, 1 year or shorter.

In one embodiment of the invention the classification of a tumor may be used to improve survival prediction using clinical parameters. The inventors have for example shown (Example 3C) that when subtype classification by use of Signature 1 (VGLL3, IGFBP3 and F3) is added to conventional prediction models using only clinical parameters the accuracy of prediction is significantly improved.

In one aspect the invention provides a method for taking a decision on future treatment for the patient, the decision being dependent on the classification according to the invention. Patients that have a tumor that has been classified as being a high risk tumor need more radical or curative treatments than patients with low risk tumors, and also at an earlier stage. Radical or curative treatments include treatment regimes selected from prostatectomy, radiation, chemotherapy, castration or a combination thereof. Patients with tumors that have been classified as low risk tumors need less or no radical or curative treatment, but can be assigned to watchful-waiting or active surveillance. In certain embodiments of the invention patients with localized cancer of high risk or intermediate risk tumor subtype need radical or curative treatments without delay, while patients with localized cancer of low risk tumor subtype can be safely assigned to watchful waiting with minimal anxiety because castration therapy can be still a guarantee of long time survival in case of disease progression. For patients with advanced cancer at diagnosis, those of low risk subtype can get most benefit from castration therapy or anti-androgen therapy whereas patients of high risk and intermediate risk subtype may need to be treated by chemotherapy or other new therapies early.

In one aspect the invention further provides a method of treating the subject that has been diagnosed with prostate cancer, and whose tumor has been classified according to the invention, in accordance with the treatment decision made as above.

In one aspect the invention provides use of any of the genes IGFBP3, F3, VGLL3, c-MAF, WNT5B and/or CTGF or the proteins encoded therefrom as prognostic marker(s) for prostate cancer. In various embodiments of this aspect the invention provides use of a combination of two, three or more of the genes IGFBP3, F3, VGLL3, c-MAF, WNT5B and/or CTGF or the proteins encoded therefrom as prognostic markers for prostate cancer. One particularly useful embodiment provides use of a combination of the genes IGFBP3 and F3 and, optionally, either of VGLL3 and c-MAF, or the proteins encoded therefrom as prognostic markers for prostate cancer.

In one aspect the invention provides a solid support or a kit for classifying a tumor in a subject diagnosed with prostate cancer, comprising nucleic acid probes or antibodies that are useful for determining gene expression and are specific for a combination of at least two of the genes IGFBP3, F3, VGLL3, c-MAF, WNT5B and CTGF. In one embodiment thereof, said solid support or kit comprises nucleic acid probes or antibodies that are specific for IGFBP3 and F3. In another embodiment the solid support or kit comprises nucleic acid probes or antibodies that are specific for IGFBP3 and F3 and either or both of VGLL3 and c-MAF. In still another embodiment the solid support or kit further comprises nucleic acid probes or antibodies that are specific for EZH2, AMACR and MUC1.

The solid support may be an array, such as a cDNA microarray, a polynucleotide array or a protein array.

The nucleic acid probes for any of the kit embodiments may for example be selected from the sequences disclosed in Table 7. Such kit is particularly useful for determination of gene expression levels using multiplex PCR, e.g. multiplex quantitative PCR.

The kit may also comprise further reagents that are necessary for the measurement of gene expression level, such as secondary labeled probes or affinity ligands for detecting and/or quantifying bound or amplified nucleic acids or antibodies, depending on the selected method. Such labels may also be directly attached or linked to the nucleic acid probes or antibodies.

The kit may further comprise various auxiliary substances to enable the kit to be used easily and efficiently, e.g. solvents, wash buffers etc. In addition the kit may also advantageously comprise reference samples or information on reference gene expression level values obtained by use of the same method from patients with known high risk or low risk tumors.

TABLE 7

| Gene Symbol | Probe Sequence (5'-3') | SEQ ID NO: | Sense Primer sequence (5'-3') | SEQ ID NO: | Anti-sense Primer sequence (5'-3') | SEQ ID NO: |
|---|---|---|---|---|---|---|
| AMACR | CTGCTGGAGCCCTTCCGCCGC | 21 | CTGTGCAAGCGGTCGGATG | 22 | CACTCAGCCTGGCATAAATAAGC | 23 |
| CTGF | TGTGTGACGAGCCCAAGGACCAAACC | 24 | GGAAATGCTGCGAGGAGTGG | 25 | CGTGTCTTCCAGTCGGTAAGC | 26 |
| EZH2 | ACACGCTTCCGCCAACAAACTGGTCC | 27 | GCGGGACGAAGAATAATCATGG | 28 | TGTCTCAGTCGCATGTACTCTG | 29 |
| F3 | ACAACAGACACAGAGTGTGACCTCACCGA | 30 | AGTCAGGAGATTGGAAAAGCAAATG | 31 | CCGTGCCAAGTACGTCTGC | 32 |
| IGFBP3 | ACCCAGAACTTCTCCTCCGAGTCCAAGC | 33 | GACTACGAGTCTCAGAGCACAG | 34 | CTCTACGGCAGGGACCATATTC | 35 |
| IGFBP3 | ACAGATACCCAGAACTTCTCCTCCGAGTCCA | 36 | TACAAAGTTGACTACGAGTCTCAGAG | 37 | AGTGTGTCTTCCATTTCTCTACGG | 38 |
| c-MAF | TTTTCATAACTGAGCCCACTCGCAAGTTGG | 39 | AGCGACAACCCGTCCTCTC | 40 | GGCGTATCCCACTGATGGC | 41 |
| c-MAF | CAATCCATGAGCCAGACACCCATTCCCT | 42 | TCGAGTTTGTGGTGGTGGTG | 43 | CTAGCAAGTTATGGAGAATTTCAGATTG | 44 |
| c-MAF | TTTTCATAACTGAGCCCACTCGCAAGTTGG | 45 | AGCGACAACCCGTCCTCTC | 46 | GGCGTATCCCACTGATGGC | 47 |
| c-MAF | TTTTCATAACTGAGCCCACTCGCAAGTTGG | 48 | AGCGACAACCCGTCCTCTC | 49 | GGCGTATCCCACTGATGGC | 50 |
| MUC1 | CCCCTCCCCACCCATTTCACCACCA | 51 | CGCCTGCCTGAATCTGTTCTG | 52 | CTGTAAGCACTGTGAGGAGCAG | 53 |
| VGLL3 | AGACAGCTCAGCTCTCTCAAGCCAGC | 54 | AAAGCAAGATGGGGCTAACCC | 55 | TCCAAAAGGAAGTTGGGAAACTATTC | 56 |
| VGLL3 | TGCTGTAGACCTGTATCGAATCCCACGC | 57 | TGGAGCCTTTCATGGAACAGTAG | 58 | TACCACGGTGATTCCTTACTCTTG | 59 |
| VGLL3 | CTGAATACCGCTAACTTCTTCTGCTGGCC | 60 | CCCCACAGCCTACTATCAGC | 61 | GACTTCCAGAGAGTCCTGCATC | 62 |

TABLE 7-continued

| Gene Symbol | Probe Sequence (5'-3') | SEQ ID NO: | Sense Primer sequence (5'-3') | SEQ ID NO: | Anti-sense Primer sequence (5'-3') | SEQ ID NO: |
|---|---|---|---|---|---|---|
| VGLL3 | AGACAGCTCAGCTCTCTCAAGCCAGC | 63 | AAAGCAAGATGGGGCTAACCC | 64 | GGTCCAAAAGGAAGTTGGGAAAC | 65 |
| WNT5B | AGCCCTGCGACCGGCCTCGT | 66 | GGTGCTCATGAACCTGCAAAAC | 67 | AGGCTACGTCTGCCATCTTATAC | 68 |

DESCRIPTION OF THE FIGURES

FIG. 4A-K shows tables of results of multivariate analysis that was made in order to identify marker genes that show correlation to survival independent of all clinical parameters (see Example 3A).

FIG. 12A-D illustrates prediction of survival time by parametric model. Prediction of survival time was modeled by using the parametric model under the assumption of Weibull distribution. A. Overall (left part) and cancer specific (right part) survival was predicted by clinical parameters including PSA (>50 ng/ml vs. ≤50 ng/ml), clinical stage (advanced vs. localized), tumor grade (poorly vs. well+moderately differentiated) and age at diagnosis. B. Overall (left part) and cancer specific (right part) survival was predicted by clinical parameters together and tumor subtypes or groups classified by the ESCGP Signature 1. The Y axis represents actual survival time while the X axis represents predicted survival time. The 5 years survival and 8 years survival are marked on the graphs respectively for simplified interpretation. C. The table presents estimated improvement in the survival prediction by the addition of parameter of tumor subtype classification by ESCGP Signature 1. D. The table represents the contribution of the ESCGP Signature 1 and of clinical parameters respectively, in the prediction of overall and cancer survival.

EXAMPLES

Figures 1A, 1B, 1C:
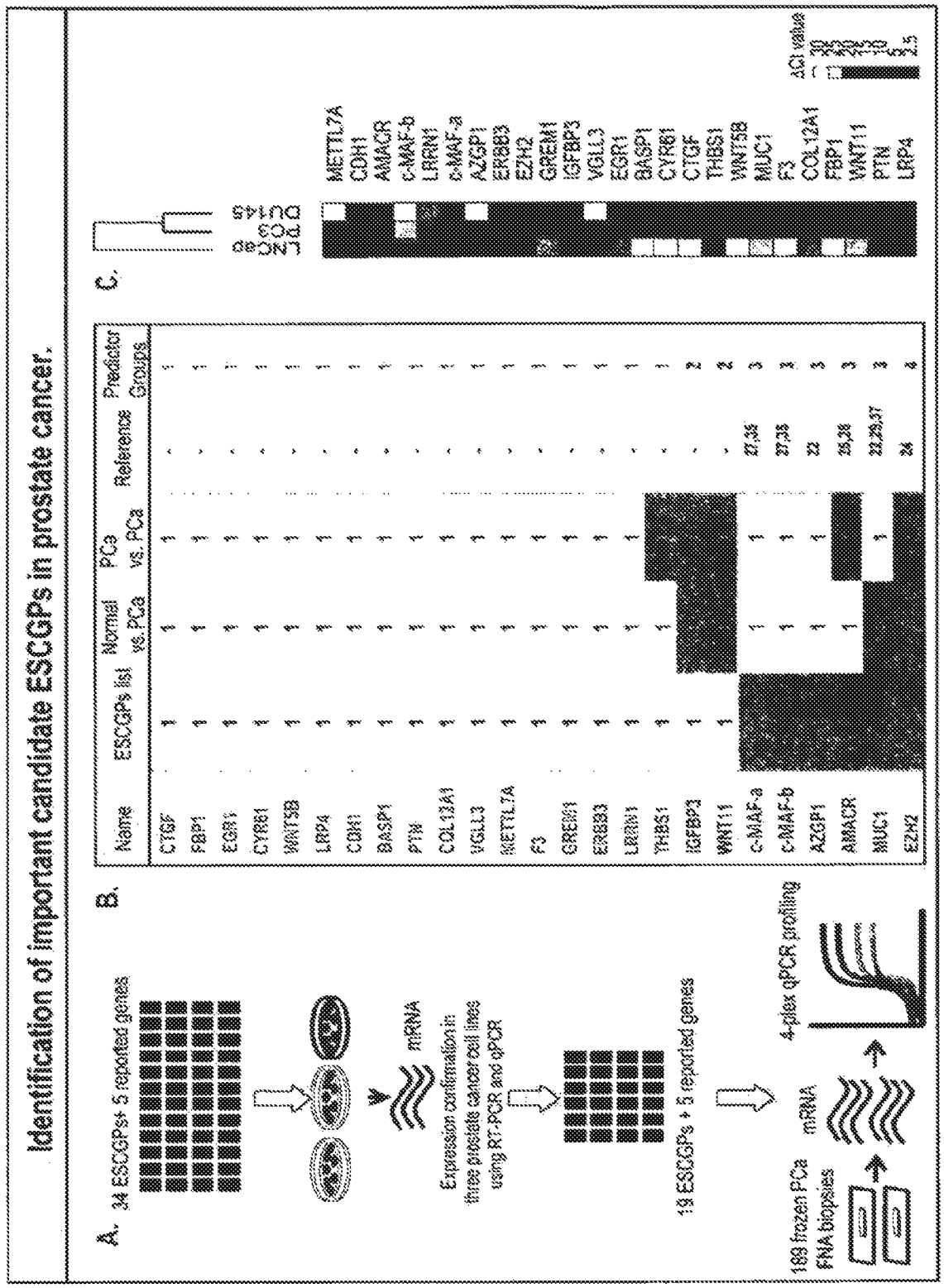
FIG. 1A-C illustrates the approach for identification of important candidate ESCGPs in prostate cancer. A. Stepwise identification of candidate ESCGPs for prostate cancer prognosis prediction. B. 19 high ranking ESCGPs and 5 control genes were selected according to 4 criterions as disclosed in Example 2A. C. The expression of these 24 genes was verified by qPCR in prostate cancer cell lines. The gene expression pattern was visualized by using Treeview software with gene-median centered delta Ct values. The level of gene expression was increasing from light grey to black while the delta Ct value was decreasing from light grey to black. White represents missing data.

General Methods
Bioinformatics Analysis

Bioinformatics analysis for identification of embryonic stem cell gene predictors (ESCGPs) has been described previously (WO 2008/013492 A1). Briefly, previously published cDNA microarray gene expression datasets were retrieved from the Stanford Microarray Database (SMD, http://smd.stanford.edu/). The criterions used for data retrieving were as following:

Gene/spot selection: all genes or clones on arrays were selected, control spots and empty spots were not included.

Data Collapse and Retrieval: row data were retrieved and averaged by SUID; UID column contains NAME.

Data Retrieved: Log(base2) of R/G Normalized Ratio (Mean).

Selected Data Filters: Spot is not flagged by experimenter.

Data filters for GENEPIX result sets: Channel 1 Mean Intensity/Median Background Intensity>1.5 AND Channel 2 Normalized (Mean Intensity/Median Background Intensity) >1.5.

Cluster program (version 3.0) was used to carry out unsupervised hierarchical average linkage clustering and TreeView program to visualize the cluster results (Eisen et al, Proc Natl Acad Sci USA 1998, 95:14863-8). SAM (significant analysis of microarrays) was carried out as previously described (Tusher et al, Proc Natl Acad Sci USA 2001, 98:5116-21).

Data Centering of Retrieved cDNA Microarray Dataset: The cDNA microarray data of 5 human ESC lines (Sperger et al, Proc Natl Acad Sci USA 2003, 100:13350-5) and 115 human normal tissues from different organs (Shyamsundar et al, Genome Biol 2005, 6:R22) were retrieved from the SMD according to parameters described in the above. The dataset was divided into subsets by different array batches. Genes were centered within each array batch by using the gene centering function of the Cluster program. The subsets were combined again and arrays were centered by using the array centering function of the Cluster program. After centering the dataset was saved and converted into Excel form.

Prostate Cancer Cell Lines

Three prostate cancer cell lines LNCaP, DU145 and PC3 were purchased from the American Type Culture Collection (ATCC). Cell culture was carried out with medium and methods according to the instruction by ATCC. LNCaP, DU145 and PC3 Cells are maintained by Iscove's Modified Dulbecco's Medium (IMDM, Cat No. 21980-032, Invitrogen) supplemented by 10% Fetal Bovine Serum (Cat No. 10082-147, Invitrogen) and 50 unit/ml and 50 ug/ml Penicillin/Streptomycin (Cat No. 15140-163, Invitrogen).

FNA Samples

Prostate FNA (fine needle aspiration) samples were taken by routine procedure for cytology diagnosis at the Department of Clinical Cytology and Pathology, Karolinska Hospital, Stockholm, Sweden. FNA samples were obtained from 241 patients at the time of diagnosis before any treatments. At least one fresh cytology spread from each patient was Giemsa stained for clinical cytology diagnosis. Remaining duplicate fresh spreads were transferred to deep freezer and had been kept fresh frozen at 80° C. until the isolation of RNA samples. Most FNA cytology spreads with prostate cancer diagnosis were estimated to contain over 80% of tumor cells due to the well known selecting effect that the aspiration sampling process can enrich cancer cells due to their decreased cell adhesion. Of the 241 patients, isolation of RNA with good quality was successful in samples from 193 patients. Of those 189 were diagnosed with prostate cancer while 4 patients did not have prostate cancer.

Clinical Characteristics of the Cohort

In total freshly frozen FNA samples from 189 prostate cancer patients were analyzed in the present study. These 189 prostate cancer patients were diagnosed during years 1986-2001. All the 189 patients had clinical symptoms which led to the diagnosis of prostate cancer. Under oncologist supervision an internship doctor collected relevant clinical data such as age at diagnosis, date of diagnosis, cytology and biopsy diagnosis, serum PSA at diagnosis, clinical stage, primary treatment, etc. Table 8 presents details about clinical characteristics of these 189 patients.

Data for date of diagnosis, date of death and causes of death for all patients were first obtained from regional as well national registries and then verified by available original medical journals. The date for data censoring was the 31 Dec. 2008. By this time, of the 189 patients 22 were still alive, 163 were deceased and 4 were without data in the registries. Prostate cancer specific death was defined as that the primary or secondary cause of death was prostate cancer or metastases. Death due to other causes was defined as the primary and secondary causes of death were not prostate cancer or metastases. These cases included even patients who died of diseases or conditions that could become worse due to prostate cancer or related to side effects and complications of treatments.

All the 189 patients had clinical symptoms which led to digital rectal examination, PSA test and subsequent prostate FNA. Castration therapy was the only primary treatment for most patients (77.9%) when the disease became advanced.

were considered as qualified. In the present study, qualified total RNA was isolated from 193 of the 241 FNA samples for further cDNA synthesis and qPCR experiments.

RT-PCR

Figure 2:
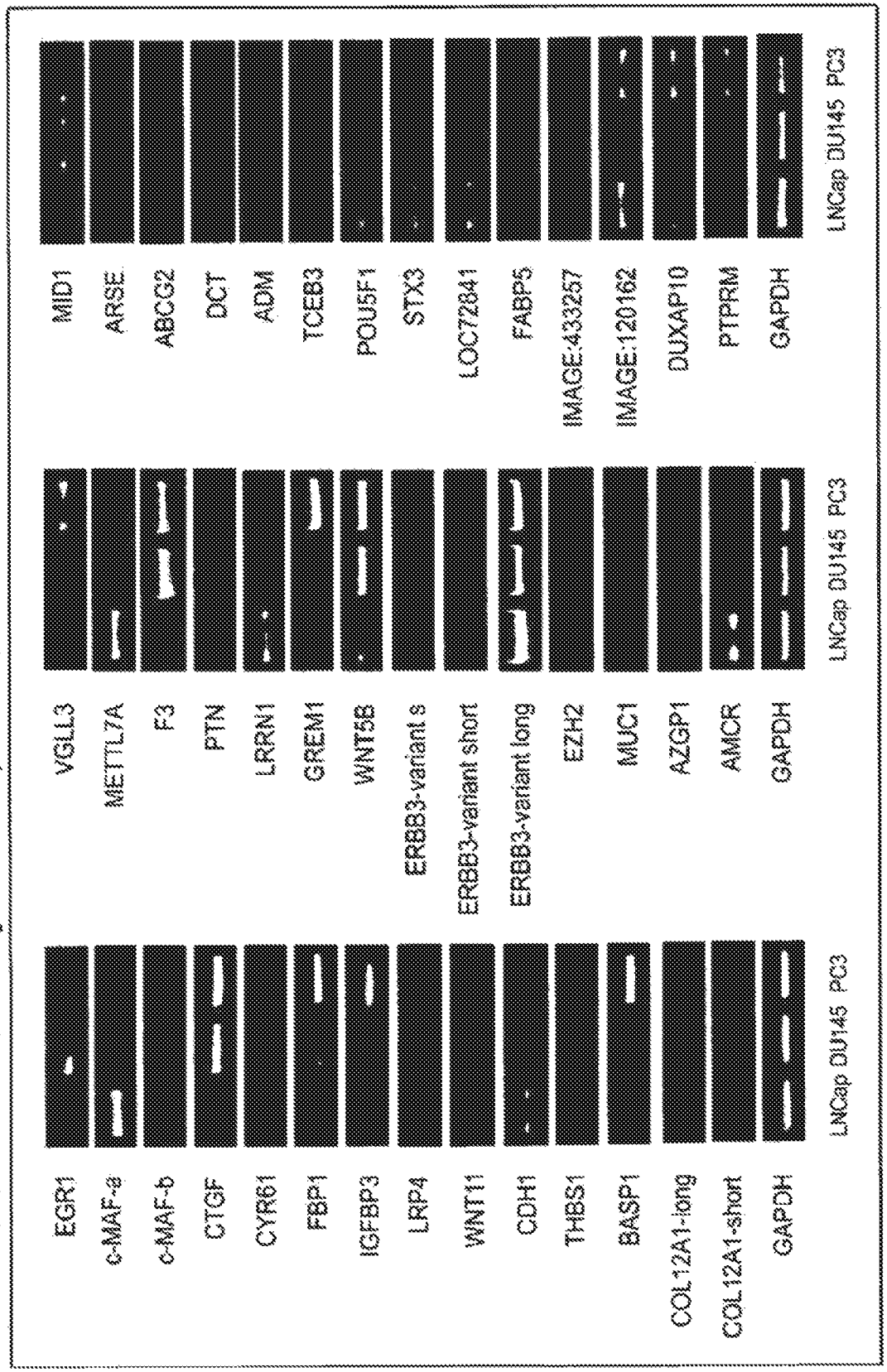
FIG. 2 illustrates expression of ESCGPs by RT-PCR in Prostate Cancer Cell Lines as described in Example 2B. The expression patterns of 34 ESCGPs and 5 control genes (c-MAF, AZGP1, AMACR, MUC1 and EZH2) were verified in the three prostate cancer lines (LNCaP, DU145 and PC3) by RT-PCR with 50 ng cDNA as template for each reaction. Glyceraldehyde-3-phosphate dehydrogenase (GAPDH) was used as internal loading control gene.

For reverse transcription (RT) reactions, cDNA synthesis for PCR (polymerase chain reaction) was carried out by using a Cloned AMV First-Strand cDNA Synthesis Kit (Cat No. 12328-032, Invitrogen) according to the manufacturer's instruction. Maximally 2 ug total RNA was used for RT in 20 ul reaction volume. The expression patterns of 33 ESCGPs and 5 control genes in prostate cancer cell lines were validated by RT-PCR using gene specific primer pairs (FIG. 2). For each PCR reaction 50 ng cDNA was used and the experiment was repeated three times. Conventional methods for primer design and PCR cycling conditions were used.

4-Plex Real Time qPCR

First-strand cDNA synthesis for quantitative PCR (qPCR) was run using a QuantiTect® Reverse Transcription Kit (Cat

TABLE 8

Clinical characteristics of the subjects.

| Characteristic | Training set | Validation set 1 | Validation set 2 | Complete set |
|---|---|---|---|---|
| Fine Needle Aspiration (FNA) Samples | | | | |
| Gene-profiled FNA, No. (%) | 36 | 65 | 88 | 189 |
| Median survival (Min-Max), yr | 7.65 (0.07-17.80) | 4.00 (0.21-15.67) | 4.32 (0.19-15.08) | 4.32 (0.07-17.80) |
| Prostate specific death, No. (%) | 13 (36.1) | 40 (61.5) | 45 (51.1) | 98 (51.8) |
| Other death, No. (%) | 19 (52.8) | 21 (32.3) | 25 (28.4) | 65 (34.4) |
| Alive, No. (%) | 3 (8.3) | 3 (4.6) | 16 (18.2) | 22 (11.6) |
| Missing, No. (%) | 1 (2.8) | 1 (1.5) | 2 (2.3) | 4 (2.1) |
| Age, yr * | | | | |
| Mean age, yr | 70.4 ± 7.8 | 72.1 ± 8.7 | 73.8 ± 8.9 | 72.6 ± 8.7 |
| Missing | 1 | 1 | 2 | 4 |
| PSA level (ng/ml), No. (%) † | | | | |
| >50.0 | 10 (35.7) | 23 (43.4) | 35 (43.8) | 68 (42.2) |
| ≤50.0 | 18 (64.3) | 30 (56.6) | 45 (56.3) | 93 (57.8) |
| Missing | 8 | 12 | 8 | 28 |
| Clinical Stage, No. (%) ‡ | | | | |
| Advanced | 13 (40.6) | 32 (54.2) | 53 (60.7) | 96 (54.9) |
| Localized | 19 (59.4) | 27 (45.8) | 31 (39.3) | 79 (45.1) |
| Missing | 4 | 6 | 4 | 14 |
| Tumor WHO Grade, No. (%) § | | | | |
| Poorly | 14 (38.9) | 31 (50.0) | 54 (62.1) | 99 (53.5) |
| Moderate/Well | 22 (61.1) | 31 (50.0) | 33 (37.9) | 86 (46.5) |
| Missing | 0 | 3 | 1 | 4 |
| Treatment No. (%) ‖ | | | | |
| Radical prostatectomy | 1 (3.2) | 3 (5.0) | 4 (4.9) | 8 (4.7) |
| Radiation | 5 (16.1) | 2 (3.3) | 11 (13.6) | 18 (10.5) |
| Hormone/Ablatio testis | 19 (61.3) | 53 (88.3) | 62 (76.5) | 134 (77.9) |
| Never treated | 6 (19.4) | 2 (3.3) | 4 (4.9) | 12 (7.0) |
| Missing | 5 | 5 | 7 | 17 |

RNA Isolation

AliPrep DNA/RNA Mini Kit (Cat No. 80204, QIAGEN) was used for total RNA isolation in prostate cancer cell lines. RNAqueous®-Micro Kit (Cat No. 1931, Ambion) for isolation of total RNA less than 100 ng was used to isolate total RNAs from freshly frozen FNA samples from prostate cancer patients. RNA quantity and quality were controlled by using Agilent RNA 6000 Nano Kit (Cat No. 5067-1511, Agilent) on a 2100 RNA Bioanalyzer (Agilent). RNA samples with RNA integrity number (RIN) larger than 7

No. 205311, QIAGEN). Up to 1 ug total RNA was used for each qPCR in 20 ul reaction volume. The reaction was run on an ABI 7500 real time cycler that could in real time simultaneously monitor the densities of four different fluorescent dyes (4-plex). None passive reference was selected in this four-dye combination. The condition for 4-plex qPCR was at 50° C. for 2 minutes in 1 cycle; at 94° C. for 10 minutes in 1 cycle; at 94° C. for 1 minutes in 40 cycles and at 60° C. for 1.5 minutes in 1 cycle. Fixed baseline start value and end value were chosen for Ct value analysis (Schmittgen and Livak, Nat Protoc 2008, 3:1101-8; Wittwer et al, Methods 2001, 25:430-42).

Optimization of 4-Plex Real Time qPCR

A 4-plex qPCR contains four pairs of gene specific primers and four gene specific Taqman probes each of which was dual-labeled with a fluorophore on the 5' end and a quencher on the 3' end. In our study, Cy5, FAM, Texas Red and VIC were used for the 5' end labeling while BHQ-3, BHQ-1, BHQ-2 and TAMRA were used as the 3' quenchers. The four different combinations of the fluorophore-quencher pair enabled specific detection of PCR products of the 4 different genes. In total, For 19 ESCGPs and 5 control genes, 45 predicted 4-plex probes and 24 pairs of primers were designed by Beacon Designer 7.0 software (Primer Biosoft). Sequence information of probes and primers for the genes of the present invention is presented in Table 7.

Figure 3:
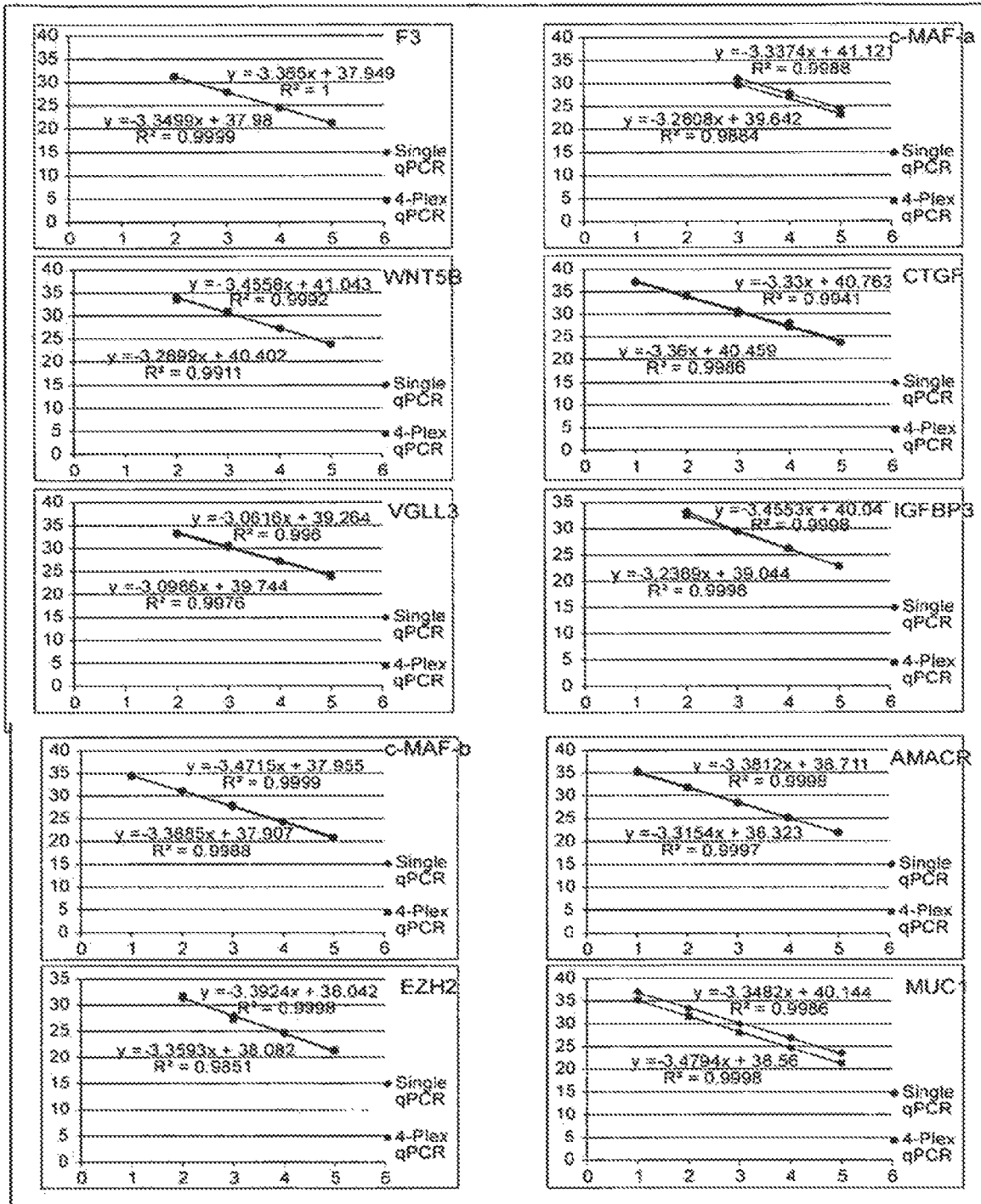
FIG. 3 illustrates verification of accuracy of 4-plex qPCR by comparison with single qPCR. In a series of cDNA dilution assay (the cDNA standard curve method), the results of single qPCR and 4-plex qPCR were compared. The optimized condition of 4-plex qPCR was defined as the one that gave the result most similar to the result of single qPCR.

To validate whether 4-plex qPCR has the same specificity and efficiency with single probe qPCR, cDNA standard curve method was used. cDNAs derived from total RNAs purified from LNCap, DU145 and PC3 cells were diluted to a series of concentrations at 10 pg, 100 pg, 1000 pg, 10000 pg, 100000 pg were used as templates for both single probe qPCR and 4-plex qPCR respectively. Standard curves are made based on the Ct value of each probe and the amount of cDNAs. The values of slope and r of cDNA standard curves derived from single probe qPCR and 4-plex qPCR of the same genes were compared. Optimization of concentrations of probes and primer pairs was carried out until there was no significant difference in these values between single and 4-plex qPCR. The results showed that 0.2 uM probes and 0.2 uM primer pairs were the best concentrations for 4-plex qPCR. Validation results of 4-plex qPCR are presented in FIG. 3.

Normalization and Centering of qPCR Result Ct Value

Ct (cycle threshold) is a measure of the number of PCR cycles (in real-time PCRs) needed to obtain a fluorescent signal or enough PCR products. In the present study, Ct value of a gene in a sample after real time PCR was generated by using 7500 software (version 2.0.5, ABI). In order to normalize the Ct values of each gene, delta Ct value was calculated according to an equation $\Delta Ct = Ct_{geneX} - Ct_{GAPDH}$ where $Ct_{geneX}$ was the Ct value of the gene to be analyzed and $Ct_{GAPDH}$ was the Ct value of the housekeeping gene GAPDH (glyceraldehyde-3-phosphate dehydrogenase) (Schmittgen and Livak, Nat Protoc 2008, 3:1101-8; Wittwer et al, Methods 2001, 25:430-42). Thus, the expression level of each gene in a sample was normalized by the expression level of GAPDH. The $\Delta Ct$ was reversely correlated with the gene expression level. Each panel of 4-plex qPCR contains one specific GAPDH probe respectively. Samples with weak signals were excluded from analysis (Ct value of GAPDH>28). Samples with weak signals of genes to be analyzed, their Ct values were set as 40 (set as the maximal value of Ct). Delta Ct values of genes in all samples were centered by using the gene median center function of a Cluster program (version 3.0) (Eisen et al, Proc Natl Acad Sci USA 1998, 95:14863-8). The centered delta Ct value was used for statistical analyses.

Statistical Analysis of Survival Correlation

Overall survival and prostate cancer specific survival were used as the endpoints respectively in survival analysis for the correlation with molecular and clinical parameters. Survival time was defined as the time from the date of diagnosis to the date of death and was used as continuous variable. For simplified interpretation, long, intermediate or short survival was defined as survival time>8, 5-8 or <5 years respectively. For patients treated primarily only by castration therapy the leading time before the treatment was defined as the time from the date of diagnosis to the date of start of castration treatment and was used as continuous variable. The centered delta Ct value of each gene, age at diagnosis and serum PSA value at diagnosis were used as continuous variables. By unsupervised hierarchical clustering analysis samples were classified into three groups or subtypes and the grouping was used as non-continuous variable. PSA was also analyzed as non-continuous variable by two categories ≤50 ng/ml or >50 ng/ml. The WHO tumor grade was integrated into two categories: well-moderate differentiated or poorly differentiated. The clinical stage was integrated into two categories: advanced (any T≥T3 or N1 or M1 or PSA≥100 ng/ml) or localized (T<T3 and N0 and M0 and PSA<100 ng/ml). Univariate as well as multivariate analyses of Cox proportional hazard ratio and Cox regression were performed by Stata (Version 10.1, StataCorp LP) statistics software. Kaplan-Meier analysis as well as statistic box plots were carried out by using JMP® statistics software (version 8.0.1, SAS Institute Inc).

Study Set Up

The study was carried out in three steps:
1) identification of an embryonic stem cell gene predictor (ESCGP) signature of 641 genes.
2) selection of a subset of important candidate genes from the ESCGP signature for classification of prostate cancer subtype and optimization of multiplex qPCR in prostate cancer cell lines.
3) verification of the clinical importance by measuring the expression levels of these selected genes in FNA samples of prostate cancer patients with 7-20 years survival data.

This resulted in identification of a subset of gene markers that show a significant correlation to either overall or cancer specific survival.

Example 1

Identification of an ESCGP Signature

An ESCGP signature for classification of various types of cancers was identified as disclosed in patent document WO 2008/013492 A1. Briefly, previously published datasets of whole genome cDNA microarray data derived from 5 human ESC lines and 115 human normal tissues from different organs were retrieved from the Stanford Microarray Database (SMD) according to parameters described above. Data centering of the retrieved datasets was also carried out as described above. Data from the normal tissues were used to aid the data centering. After centering the sub-dataset of the ESC lines was isolated from the whole dataset. A one class SAM was carried out by using only this ESC line dataset, by which all genes were ranked according to the consistency of their expression levels across the 5 ESC lines. By using a q-value 0.05 as cut-off the analysis identified 328 genes with consistently high and 313 genes consistently low expression levels in the ESCs. The 641 genes were named as embryonic stem cell gene predictors (ESCGPs).

Example 2A

Selection of Important Candidate ESCGPs in Prostate Cancer

From the list of 641 ESCGPs a subset of 33 ESCGPs as well as 5 control genes were selected as candidates that may enable classification of prostate cancers using fewer ESCGPs. The candidates were selected according to four criteria (see FIG. 1B), i) ranking position in the 641 gene ESCGP list (denoted "ESCGPs list" in FIG. S1 B); ii) ranking position in the gene list identified by Lapointe et al (Proc Natl Acad Sci USA 2004, 101:811-816) comprising significant genes for classification of prostate cancer subtypes (denoted "PCa vs. PCa" in FIG. 1B), iii) ranking position in the gene list identified by Lapointe et al (Proc Natl Acad Sci USA 2004, 101:811-816) comprising significant genes distinguishing between prostate cancer and normal tissues (denoted "Normal vs. PCa" in FIG. 1B): and iv) genes from previous important publications (Lapointe et al, Proc Natl Acad Sci USA 2004, 101:811-816; Varambally et al, Nature 2002, 419:624-629; Rubin et al, JAMA 2002, 287:1662-70). In FIG. 1B genes were marked with "1" if present and "0" if not present in the respective gene lists. Thus some genes fulfilled all four criteria, while other genes fulfilled 1-3 of the four criteria. AZGP1, c-MAF, AMACR, MUC1 and EZH were not identified in the list of ESCGPs but were included as important control genes because they have been identified as having importance in prostate cancer by previous studies. A few genes such as c-MAF have different RNA transcripts (http://www.ncbi.nlm.nih.gov/gene/4094). Primers and probes were designed targeting these different RNA transcripts respectively.

Example 2B

Verification of Expression of the Selected Genes in Prostate Cancer Cell Lines

Expression of the 33 selected ESCGPs and 5 control genes in three different prostate cancer cell lines were validated by RT-PCR using gene specific primer pairs (see FIG. 2). The cell lines used for analysis were LNCap, which derives from a less aggressive cancer, and DU145 and PC3, both of which derive from aggressive cancers. Of the 38 genes analyzed, 14 had a similar expression in all three cell lines and were regarded as less likely to be valuable for tumor classification. The remaining 24 genes had different expression patterns in the less aggressive cell line LNCap and the aggressive cell lines DU145 and PC3, and therefore were considered being more likely to be useful for tumor classification to distinguish between less aggressive and more aggressive cancers. Thus, in total 24 genes (25 gene markers) were selected for the optimization of multiplex qPCR and evaluation of capability to classify prostate cancer.

Example 3A

Focused Gene Expression Profiling of Prostate Cancer FNA Samples and Identification of Significant ESCGPs that Correlate with Survival Expression of the 24 genes (25 gene markers) was analyzed in fine needle aspiration (FNA) samples from 189 prostate cancer patients by use of multiplex qPCR, and then analyzed for correlation with survival data. Clinical characteristics of the patient cohort as well as the statistical analysis is described above.

All candidate genes could not be analyzed in every FNA sample due to small amount of total RNA from most FNA samples. To compromise the limitation, the cohort of 189 patients was divided into three sets according to the experiment time order. The three sets contained samples from 36, 65 and 88 patients respectively (Table 8). Only genes that showed significant correlation with survival in the first subset were included together with new candidate genes in the subsequent subset. Survival analysis was carried out in each of the three subsets as well as in the final complete cohort (Table 1, FIGS. 5-7). This compromised screen process ensured the discovery of most significant gene markers but may miss a few gene markers with modest significance.

Analysis of correlation with survival was carried out for both clinical parameters known for the patients and for gene expression of the selected candidate genes. In univariate analysis all clinical parameters showed significant correlation with both overall and cancer specific survival (Table 1). Ten of the 25 gene markers, F3 (coagulation factor III), WNT5B (wingless-type MMTV integration site family, member 5B), VGLL3 (vestigial like 3 (*Drosophila*)), CTGF (connective tissue growth factor), IGFBP3 (insulin-like growth factor binding protein 3), c-MAF-a (long form of v-maf musculoaponeurotic fibrosarcoma oncogene homolog (avian)), c-MAF-b (short form of v-maf musculoaponeurotic fibrosarcoma oncogene homolog (avian)), AMACR (alpha-methylacyl-CoA racemase), MUC1 (mucin 1, cell surface associated) and EZH2 (enhancer of zeste homolog 2 (*Drosophila*)) showed significant correlation with either overall and/or cancer specific survival (Table 1). A p-value<0.05 is considered significant throughout the study. The expression levels (reversely correlated to the delta Ct value) of all these significant genes but EZH2 showed positive correlation with survival times (value<1 in Table 1).

Each of the ten gene markers with significant correlation with survival in univariate analysis was analyzed together with clinical parameters including age at diagnosis, two-category PSA, tumor grade and clinical stage in multivariate analysis (FIG. 4A-K). Multivariate analysis indicates how much the significance of the gene variable is influenced by clinical parameters. The number of patients included in the multivariate analysis was smaller than that in the univariate analysis due to missing data of different parameters. In summary, 4 genes (F3, IGFBP3, CTGF and AMACR) showed correlation to both overall and cancer specific survival independent of all clinical parameters. All the 4 genes but AMACR were from the list of ESCGPs. Two genes (WNT5B and EZH2) showed independent correlation to cancer specific survival and one gene (VGLL3) showed independent correlation to overall survival.

Example 3B

Identification of Significant ESCGP Signatures that Correlate with Survival

Figure 5A:
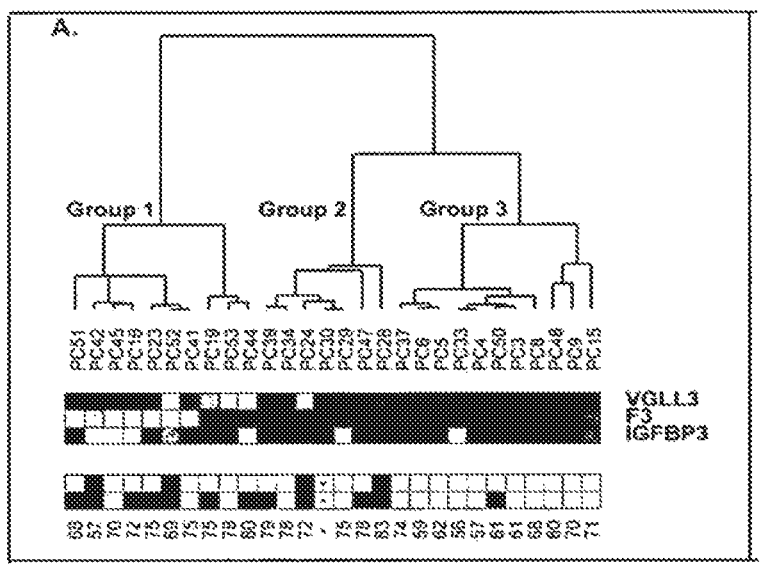
FIG. 5A-B illustrates tumor subtype classification of the training set of patients by ESCGP Signature 1 (A) and ESCGP Signature 2 (B). In the training set, 28 of 36 FNA samples had expression data for the four significant genes (F3, IGFBP, VGLL3 and c-MAF-a). A series of cluster analyses by different gene combinations showed that two gene combinations or signatures could in a similar manner classify samples into three subtypes with strong correlation to survival. The first one (ESCGP Signature 1; A) included F3, IGFBP3 and VGLL3 and the second one (ESCGP Signature 2; B) included F3, IGFBP3 and c-MAF-a. The level of gene expression increases with decreasing ΔCt value.
Figure 5B:
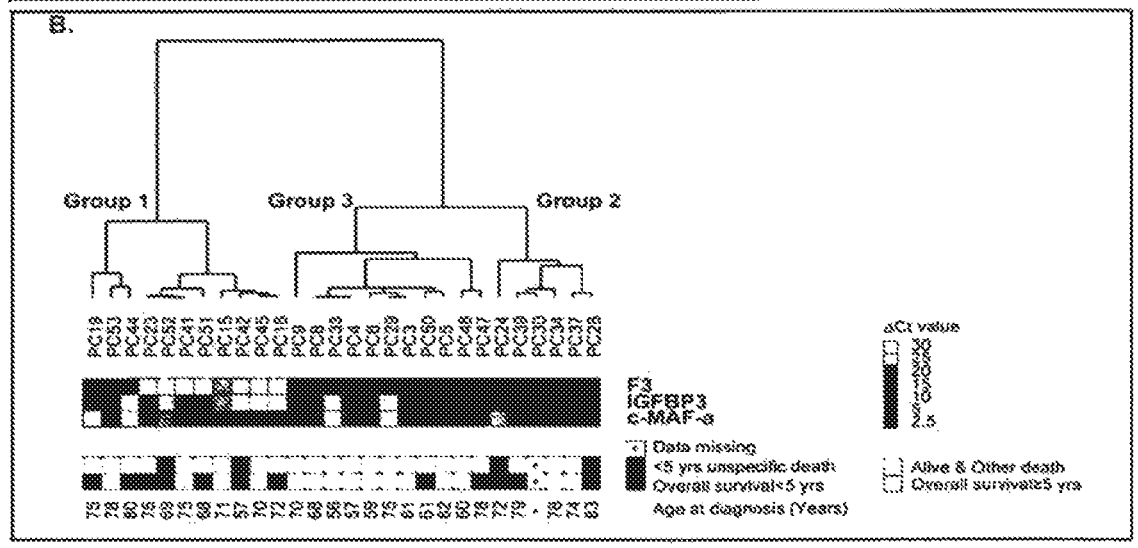
Figure 6A:
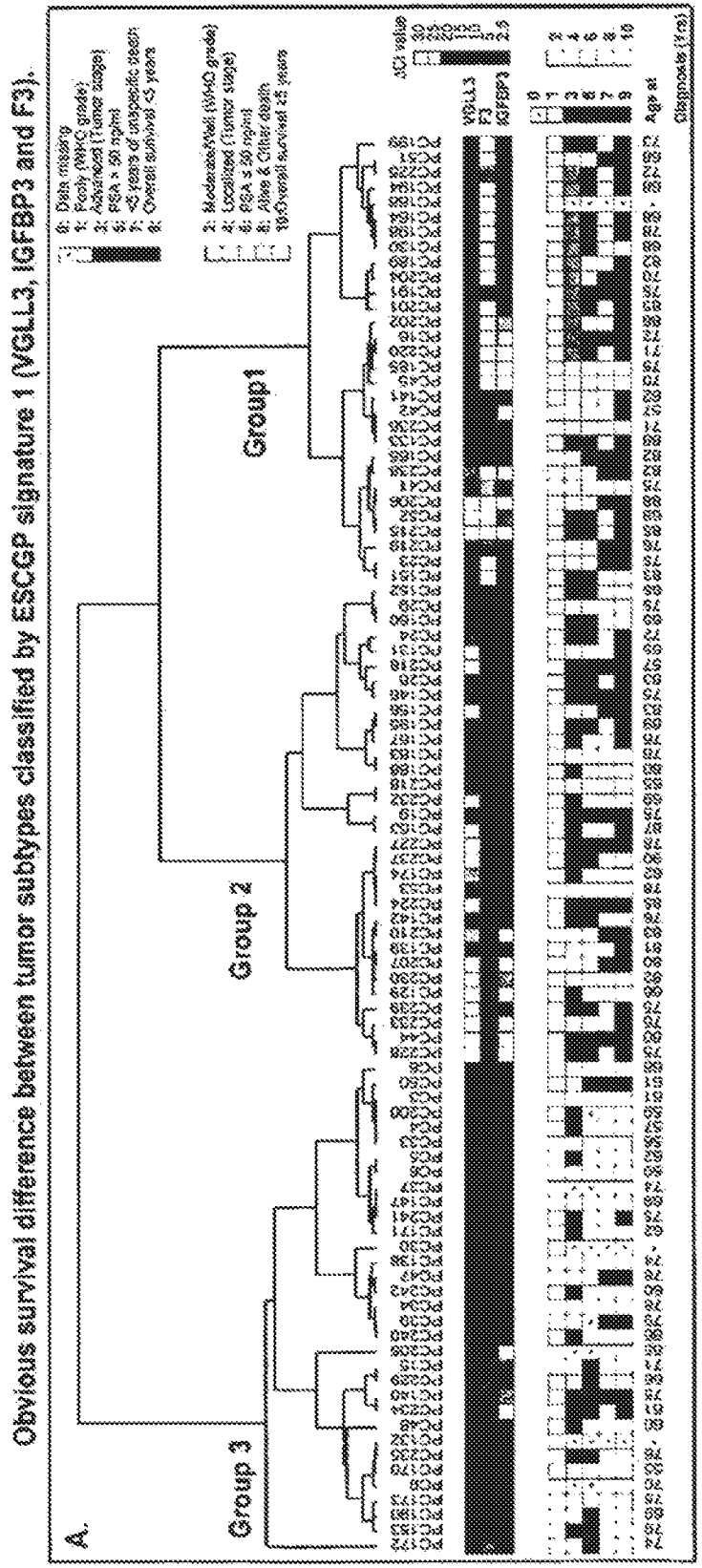
FIG. 6A-F illustrates survival differences between tumor subtypes classified by ESCGP Signature 1 (F3, IGFBP3 and VGLL3). A. FNA samples of 95 patients were classified into three tumor subtypes or groups (Group1, Group 2 and Group 3) by the ESCGP Signature 1 (VGLL3, IGFBP3 and F3) as described in Example 3B. The clinical parameters of each patient are marked as represented by different squares. Blank squares represented longer survival, lower PSA level, localized clinical stage or well/moderate differentiated tumor grade respectively. Squares with different fillings represented shorter survival, higher PSA level, advanced clinical stage, poorly differentiated tumor grade. The level of gene expression increases with decreasing ΔCt value. B. Overall and cancer specific survival analysis of three subgroups was shown by Kaplan-Meier curves. C. Kaplan-Meier survival curves of patients with PSA≤50 ng/ml at diagnosis. D. Kaplan-Meier survival curves of patients with age≤73 at diagnosis. E and F were statistic box plots showing the survival difference between the three subtypes or groups. The ends of box are 25th and 75th quartiles and the line across the middle of box presented the median value with the 95% confidence interval (CI). The p values were calculated by t-test and the p values marked with a star behind were of statistical significance.
Figures 6B, 6C:
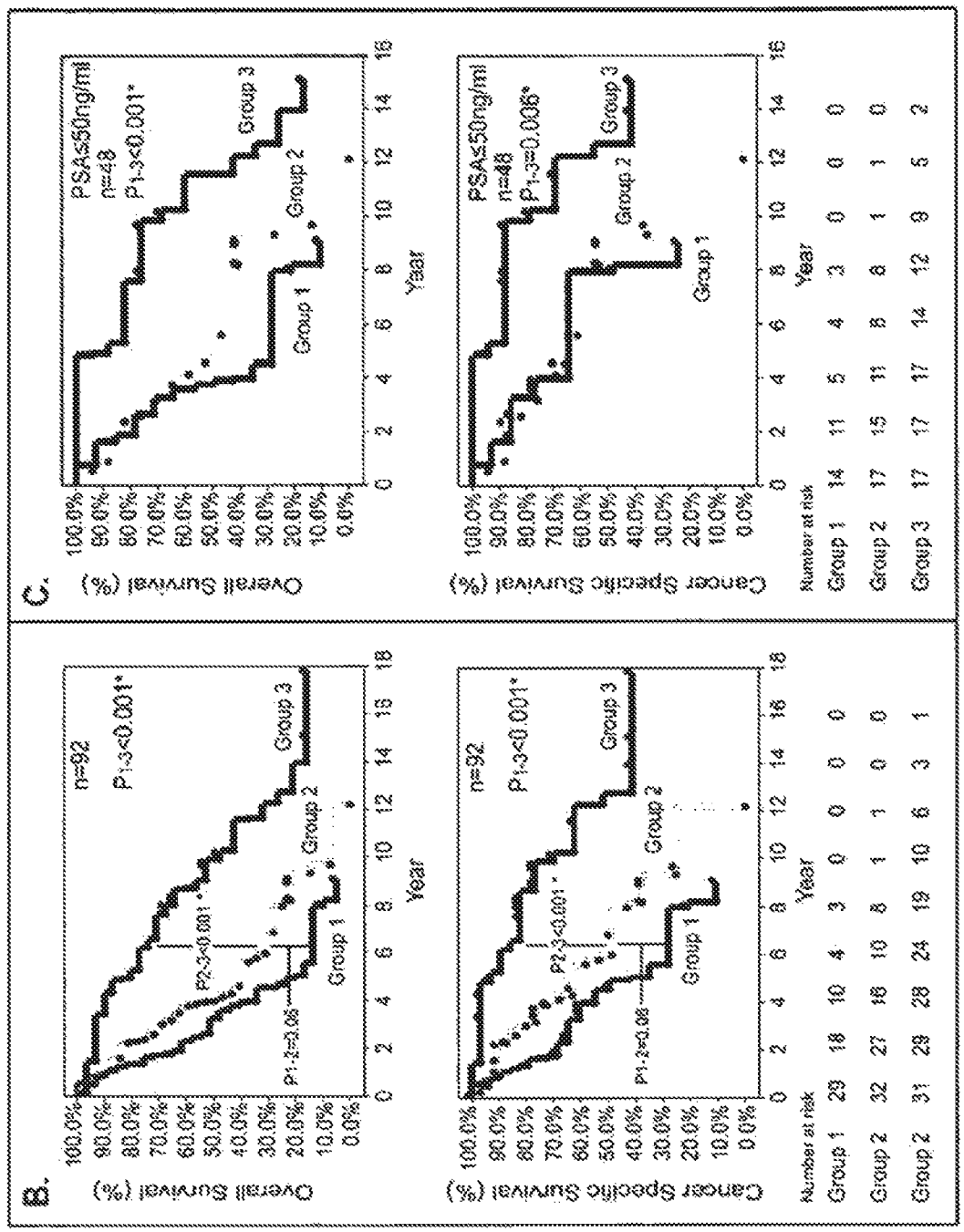

In order to study possible additive or synergic effects of multiple genes in the prediction of survival, the inventors tested different combinations of the ten significant genes in a series of unsupervised hierarchical clustering analyses using the data of patients in the first set (training set). Two signatures could in a similar manner classify tumors into three subgroups or subtypes with significant difference in overall and cancer specific survival (FIG. 5). The first ESCGP signature (Signature 1) includes the marker genes VGLL3, IGFBP3 and F3. The second ESCGP signature (Signature 2) includes the marker genes c-MAF-a, IGFBP3 and F3. The tumor subtype classification by use of the respective signature was confirmed by using the data of patients in the complete set (FIGS. 6 and 7).

The ESCGP Signature 1 (VGLL3, IGFBP3 and F3) showed better results than the ESCGP Signature 2 (c-MAFa, IGFBP3 and F3) (Tables 2 and 3). Of the 189 patients, 87 had data for both all clinical parameters and for the subtype classification by Signature 1. Multivariate analysis for overall and cancer specific survival showed that the subtype classification by Signature 1 was the most significant parameter and independent of age, PSA level, tumor grade and clinical stage (Table 2).

Median overall survival was 2.60 years in the high risk, 3.85 years in the intermediate risk and 7.98 years in the low risk subtype (FIG. 6E), corresponding to a hazard ratio of 5.86 (95% CI 2.91-11.78, P<0.001) for the high risk and 3.45 (95% CI 1.79-6.66, P<0.001) for the intermediate risk over the low risk subtype (Table 3). The difference of overall survival was attributed to both cancer specific and non-cancer specific survival (FIG. 6E).

Figures 6D, 6E, 6F:
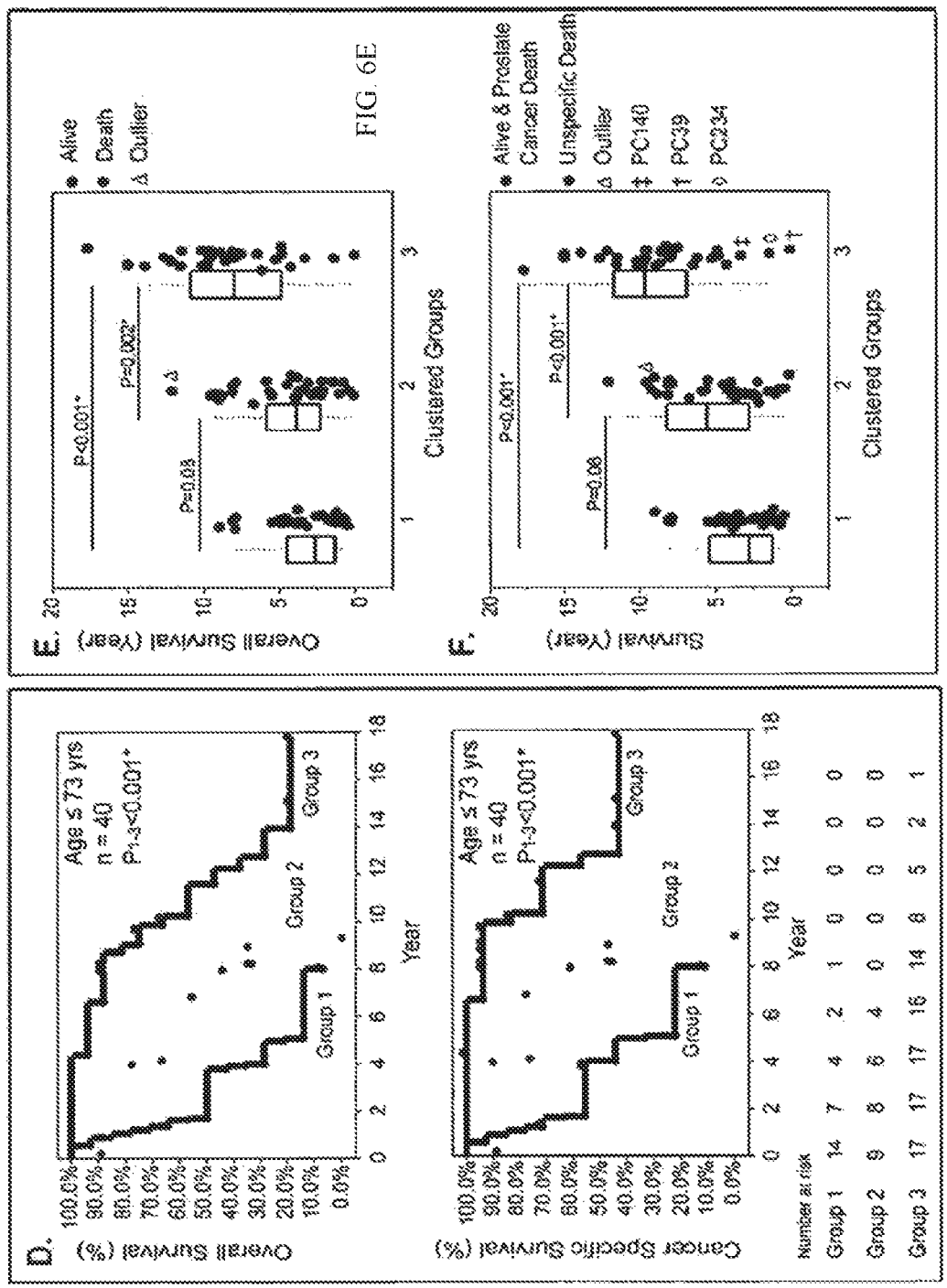
Figure 7:
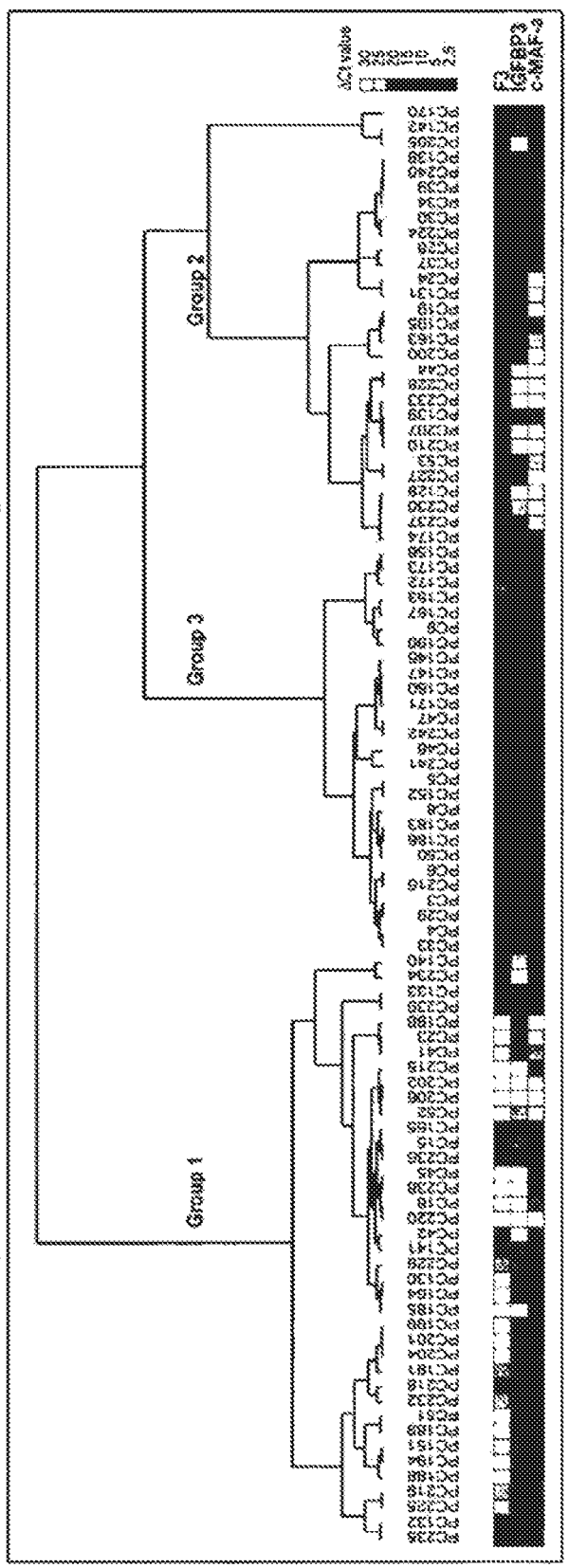
FIG. 7 illustrates tumor subtype classification of the complete set of patients by ESCGP Signature 2. The same 95 FNA samples were classified into three main tumor subtypes or groups (Group 1, Group 2 and Group 3) by ESCGP Signature 2 (F3, IGFBP3 and c-MAF-a). The level of gene expression increases with decreasing ΔCt value.
Figures 8A, 8B:
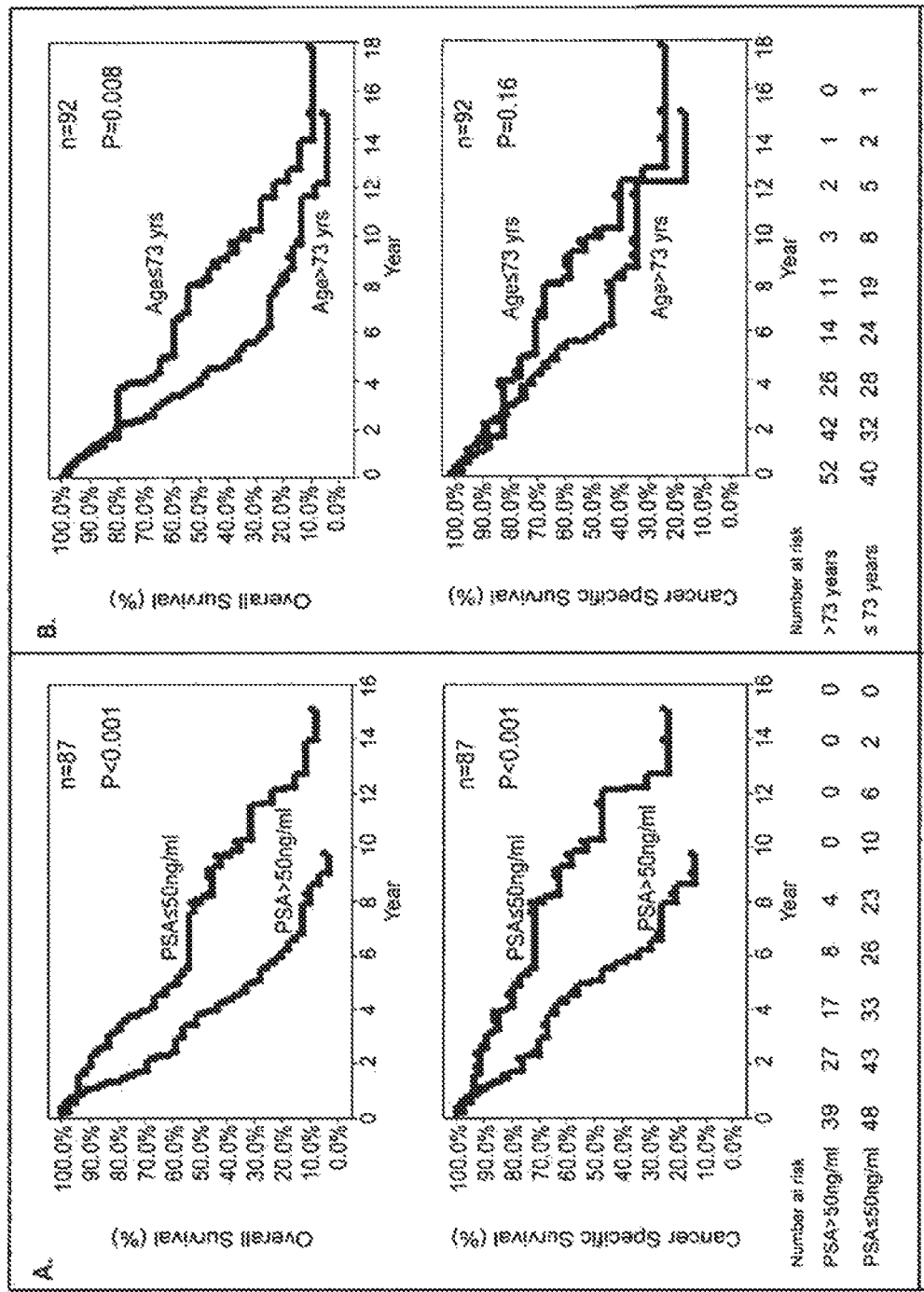
FIG. 8A-D illustrates Kaplan-Meier survival curves of patient groups defined by PSA, age, clinical stage and tumor grade. A. 87 of the 95 patients in FIG. 6 had data of serum PSA at diagnosis and survival. The patients were divided into two groups, one with PSA>50 ng/ml and the other with PSA≤50 ng/ml. B. 92 of the 95 patients in FIG. 6 had data of age at diagnosis and survival. The patients were divided into two groups, one with age≤73 years and the other with age>73 years. C. 89 of the 95 patients in FIG. 6 had data of clinical stage and survival. The patients were divided into two groups by clinical stage, one with localized stage (T≤T2 and N0 and M0 and PSA≤100 ng/ml) and the other with advanced stage (T>T2 or N1 or M1 or PSA>100 ng/ml). D. 92 of the 95 patients in FIG. 6 had data for tumor grade and survival. The patients were divided into two groups, one with poorly differentiated cancer and the other with well or moderately differentiated cancer information. All p values were calculated by Log-Rank test method.
Figures 8C, 8D:
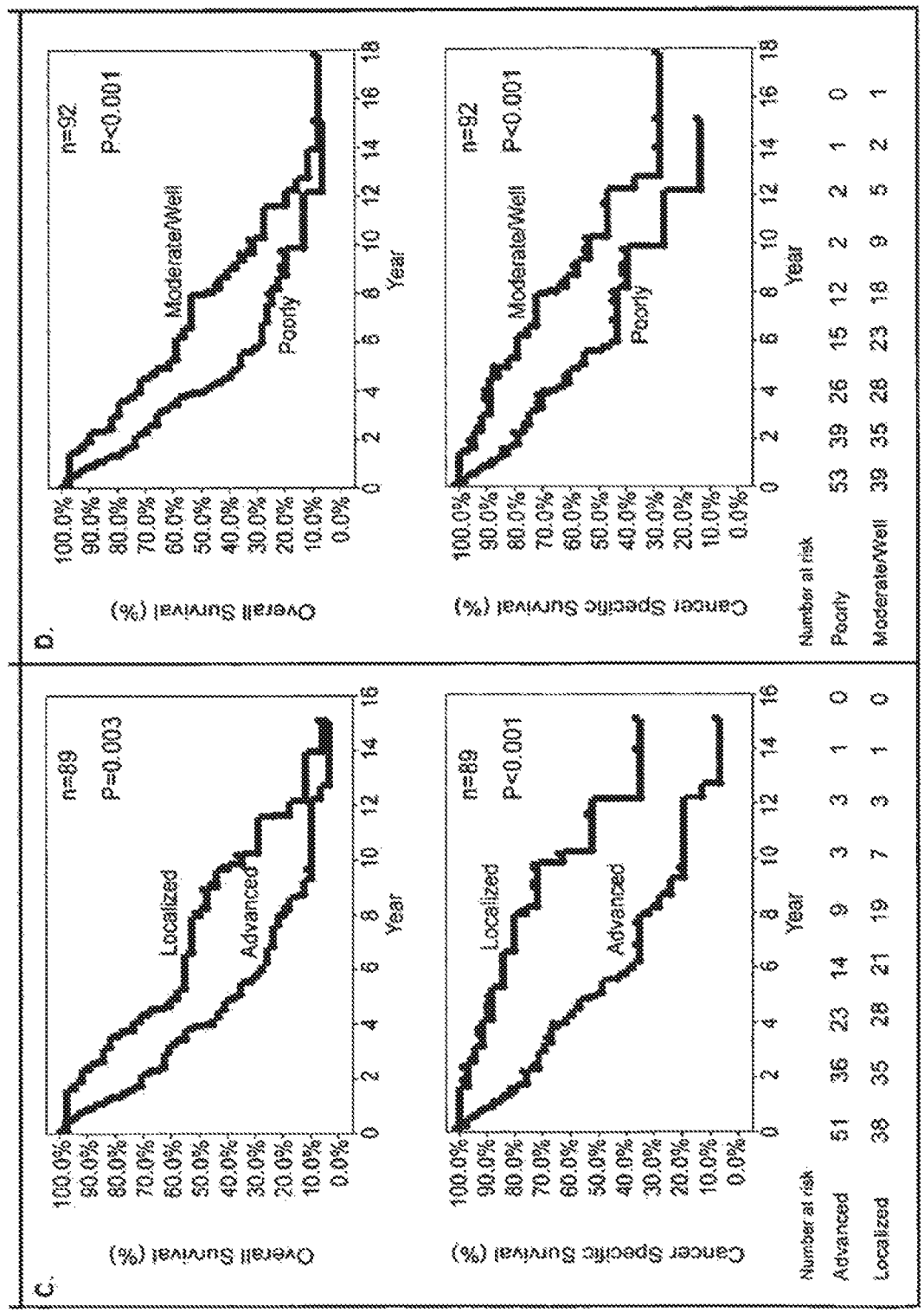
Figures 9A, 9C:
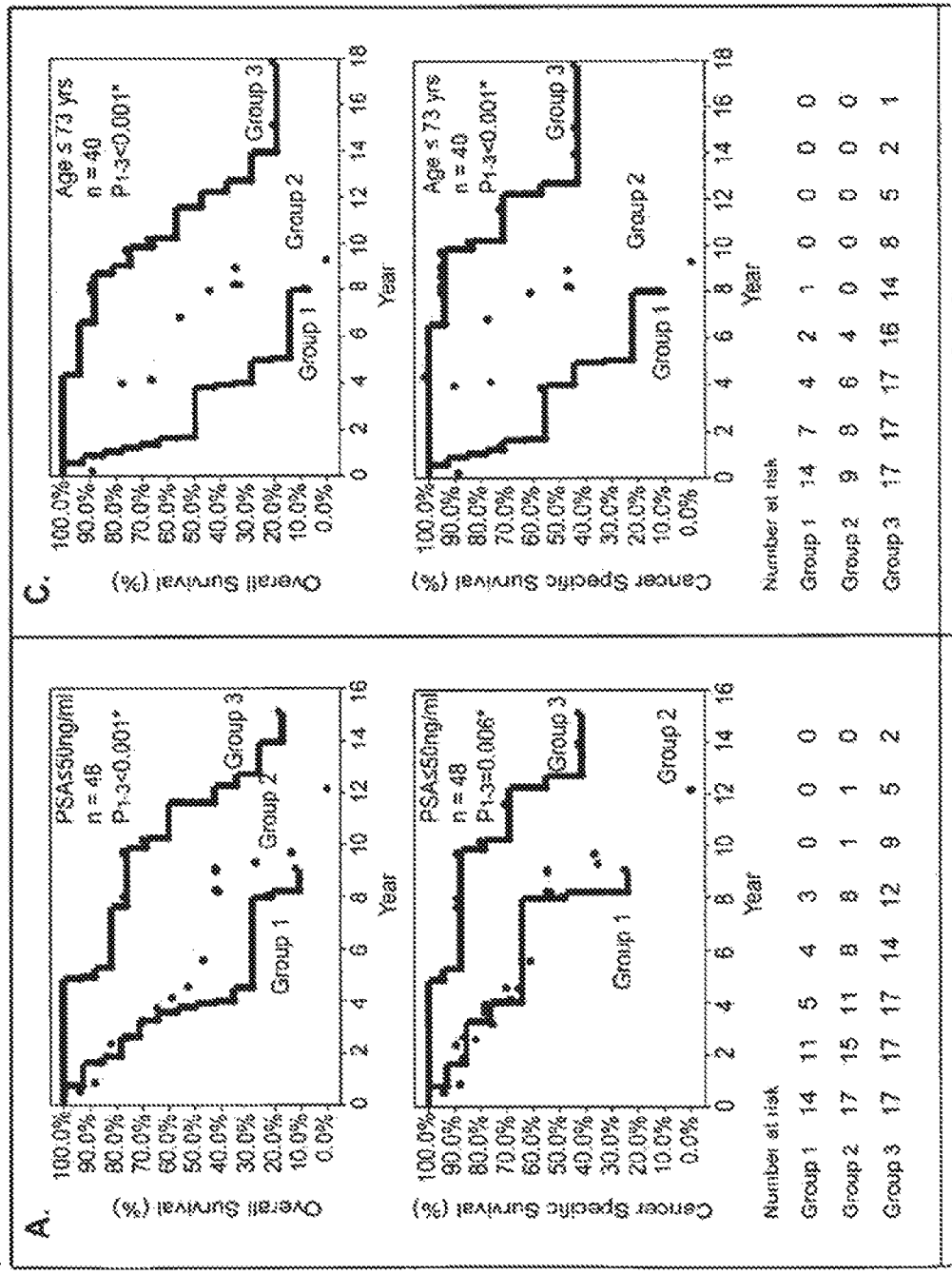
FIG. 9A-H illustrates Kaplan-Meier survival curves of the three tumor subtypes classified by ESCGP Signature 1 in Patients within the same group defined by clinical parameters. Of the 95 patients in FIG. 6, 48 of the 95 patients had PSA≤50 ng/ml (A), 39 had PSA>50 ng/ml (B), 40 were with age≤73 (C), 52 were with age>73 (D), 38 had localized stage (E), 51 had advanced stage (F), 39 had well or moderately differentiated cancer (G) and 53 had poorly differentiated cancer (H). Patients within the group of same clinical parameter could still classified by ESCGP Signature 1 (F3, IGFBP3 and VGLL3) into high risk (Group 1), intermediate risk group (Group 2) and low risk subtypes (Group 3) with obviously different survivals. Upper, lower part of each panel showed overall and cancer specific survival respectively. Log-Rank test was used to calculate significance or p value for the survival difference between the subtypes or groups.
Figures 9B, 9D:
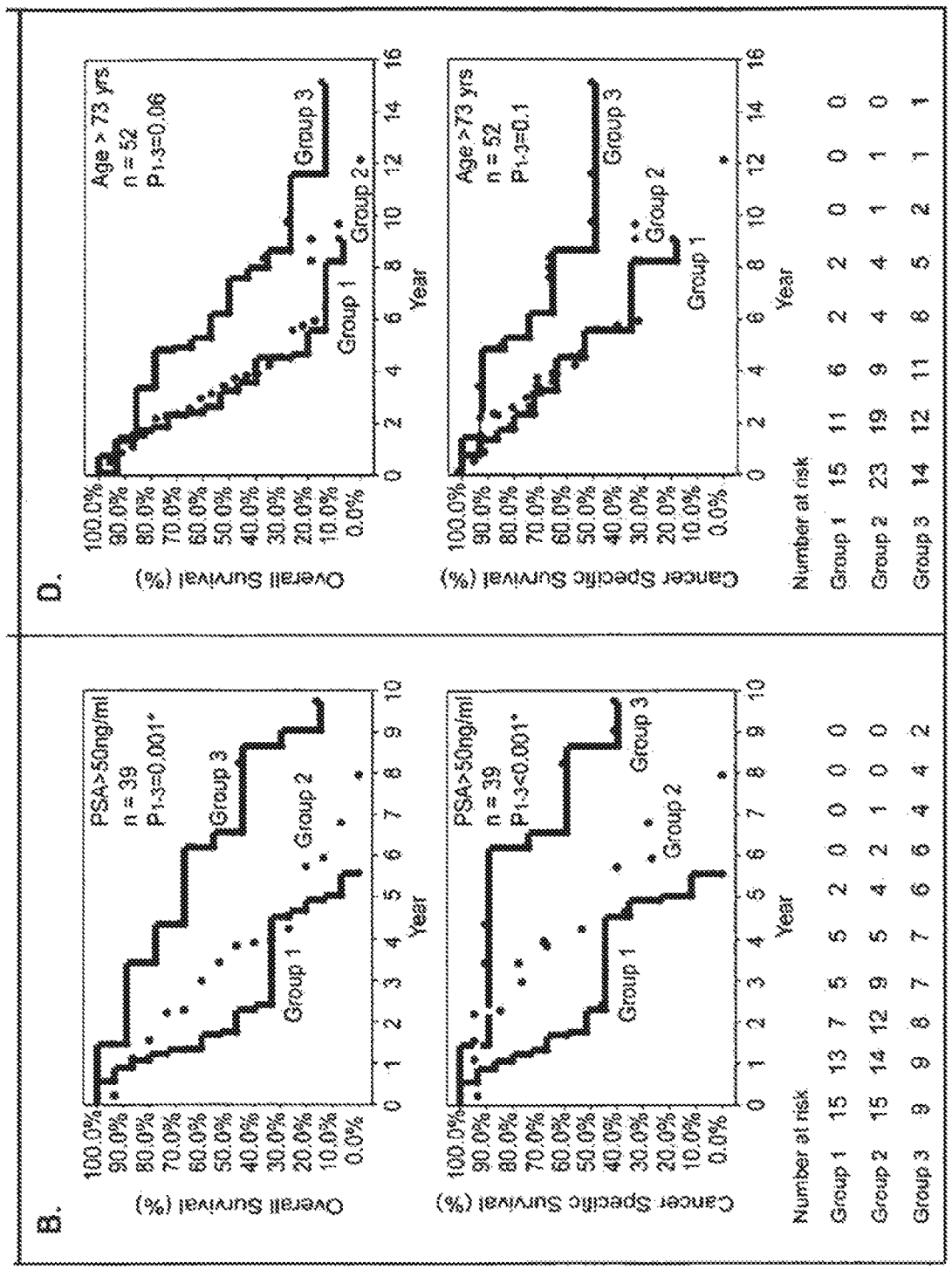
Figures 9E, 9G:
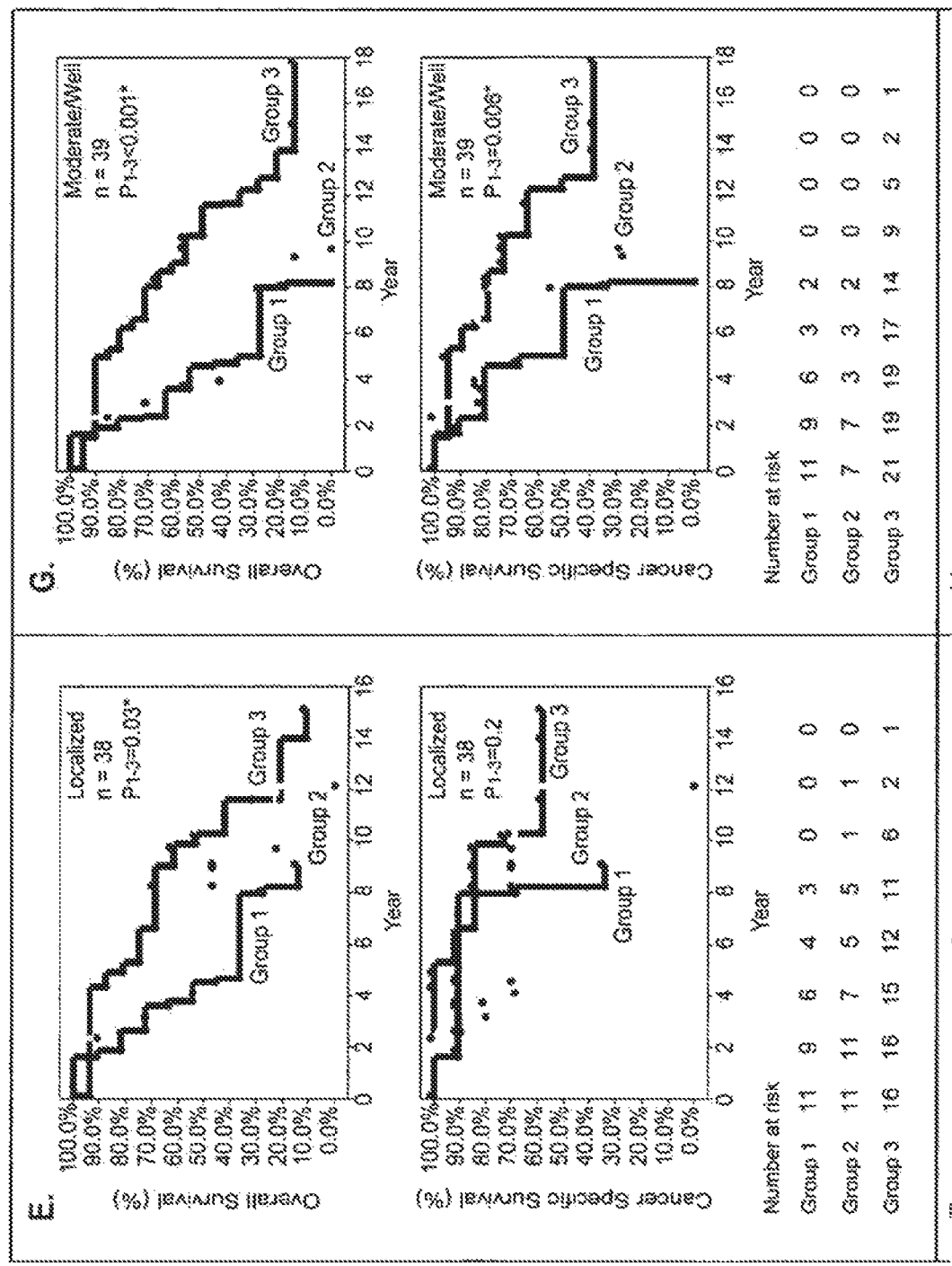
Figures 9F, 9H:
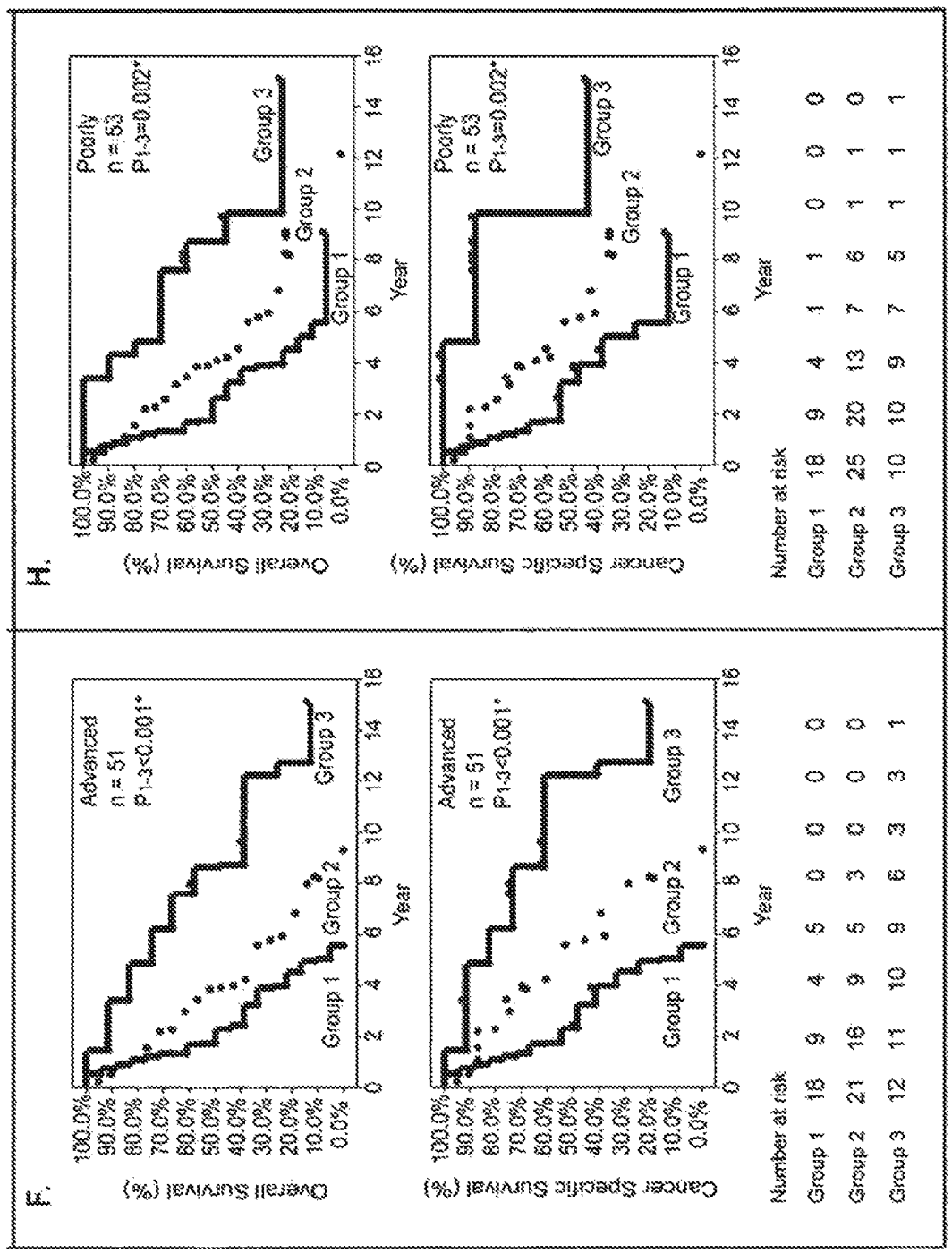
Figures 10A, 10B:
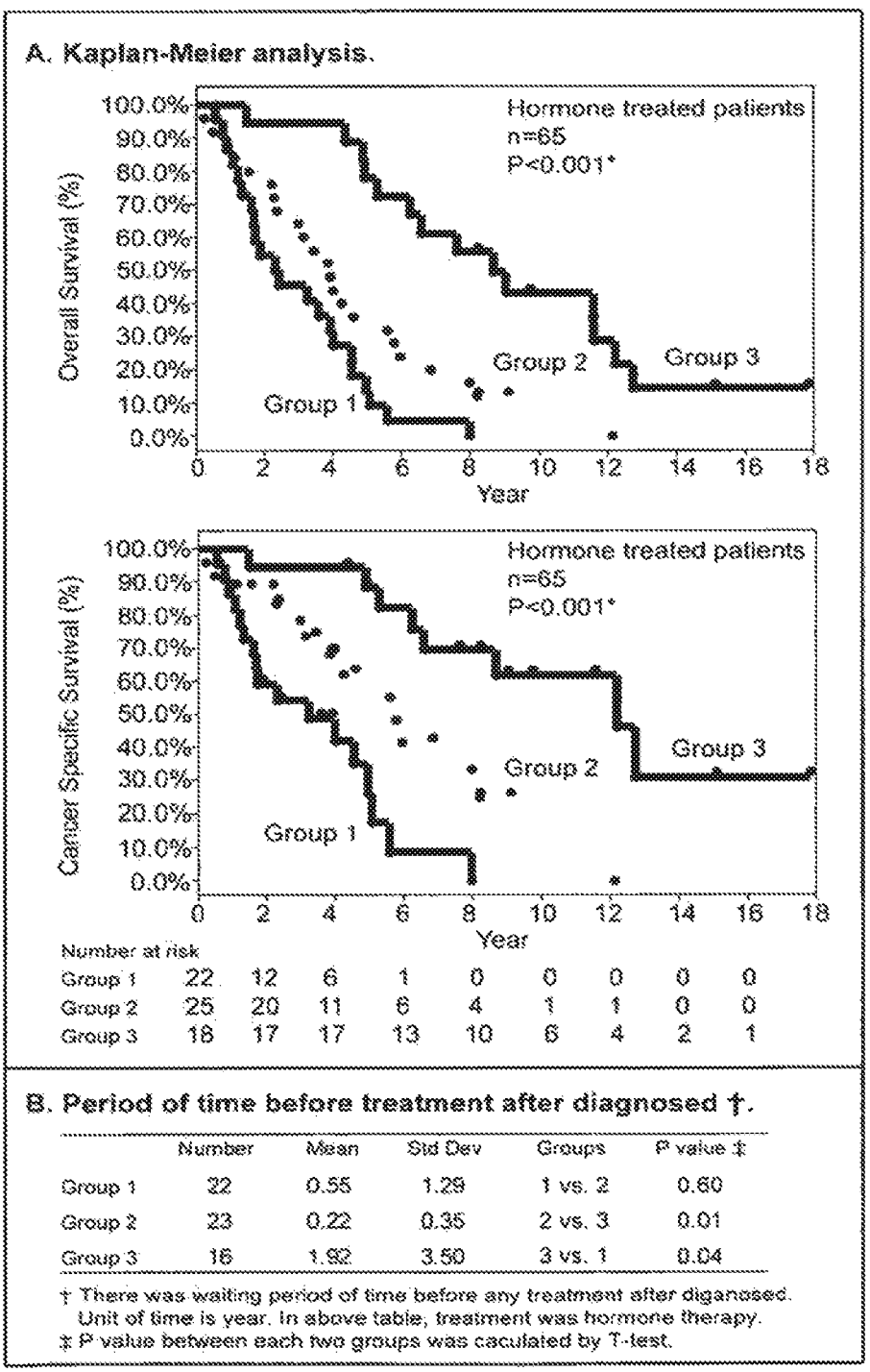
FIG. 10A-B illustrates Kaplan-Meier survival curves of the three tumor subtypes classified by the ESCGP Signature 1 in patients primarily treated only by castration therapy. Of the 95 patients in FIG. 6, 65 had castration therapy as the primary treatment (A). Obvious survival difference could still be seen between the three tumor subtypes classified by the ESCGP Signature 1 (B).
Figures 11A, 11C:
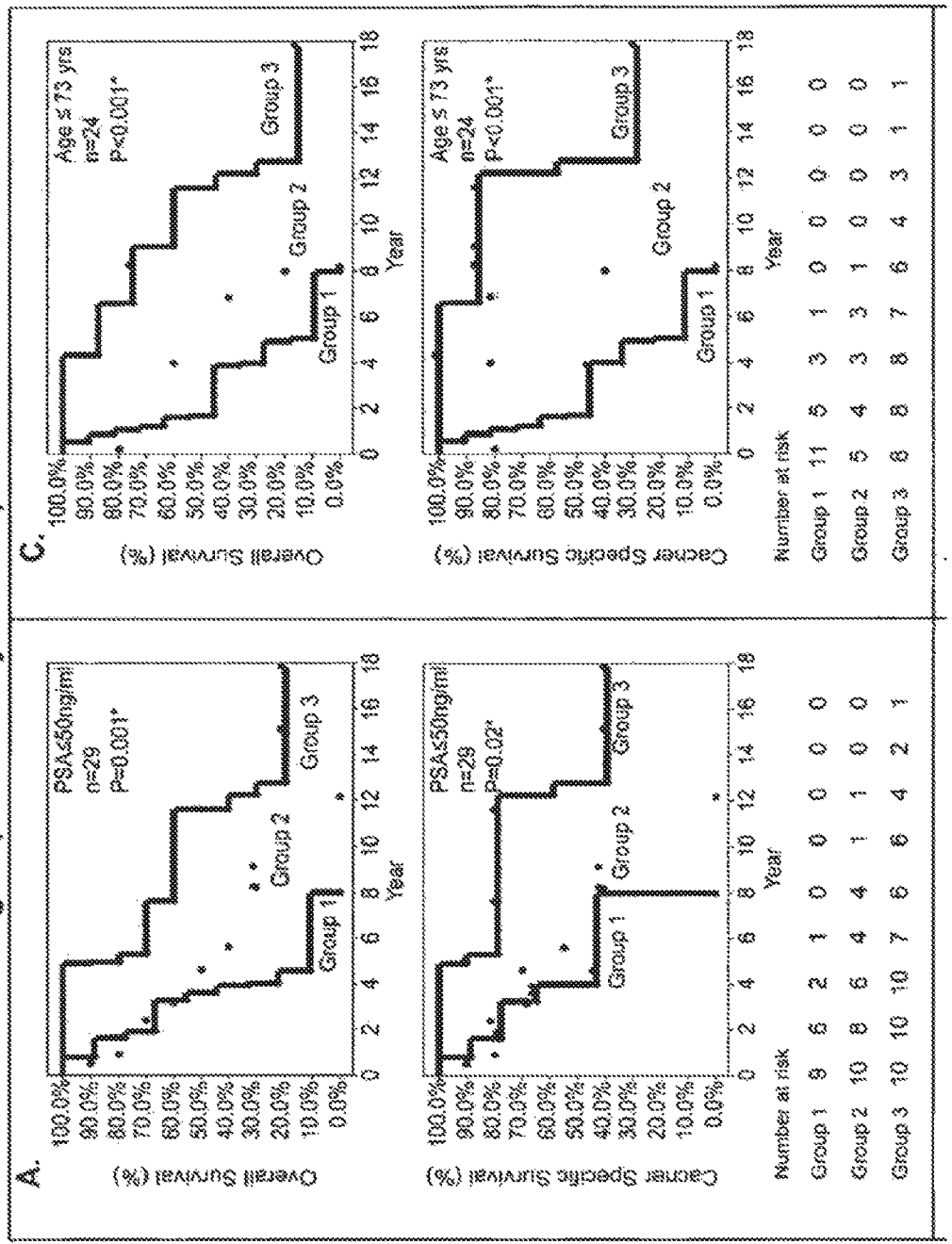
FIG. 11A-H illustrates Kaplan-Meier survival curves of the three tumor subtypes classified by the ESCGP Signature 1 in patients primarily treated only by castration therapy and within the same group defined by clinical parameters. Of 95 patients in FIG. 6, 65 had castration therapy as the primary treatment. Of these 65 patients, 29 had PSA≤50 ng/ml (A), 37 had PSA>50 ng/ml (B), 24 were with age≤73 (C), 41 were with age>73 (D), 22 had localized stage (E), 44 had advanced stage (F), 26 had well or moderately differentiated cancer (G) and 39 had poorly differentiated cancer (H). Obvious survival difference could still be seen between the high risk (Group 1) and low risk (Group 3) subtype in patients within the same group of clinical parameter.
Figures 11B, 11D:
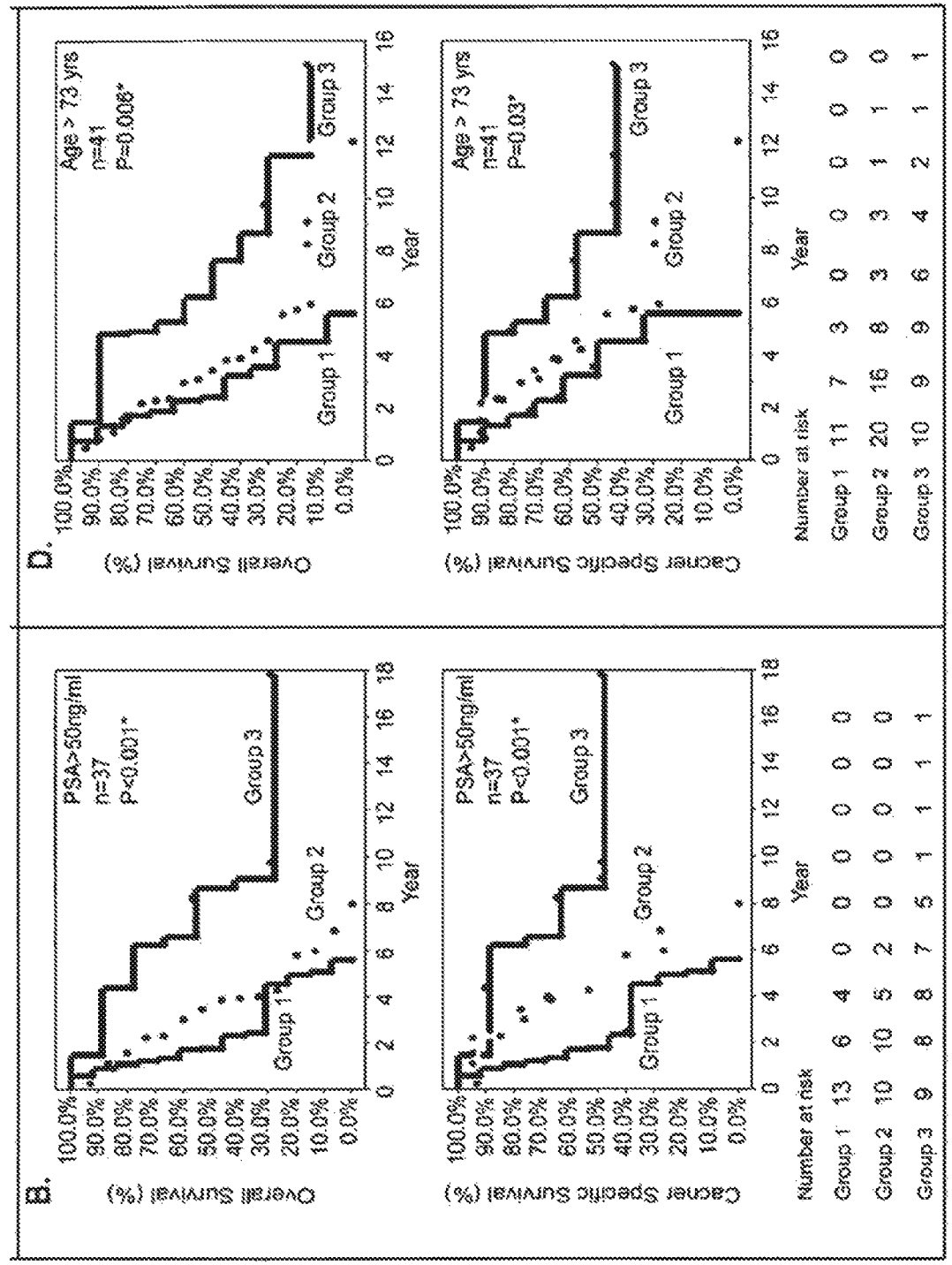
Figures 11E, 11G:
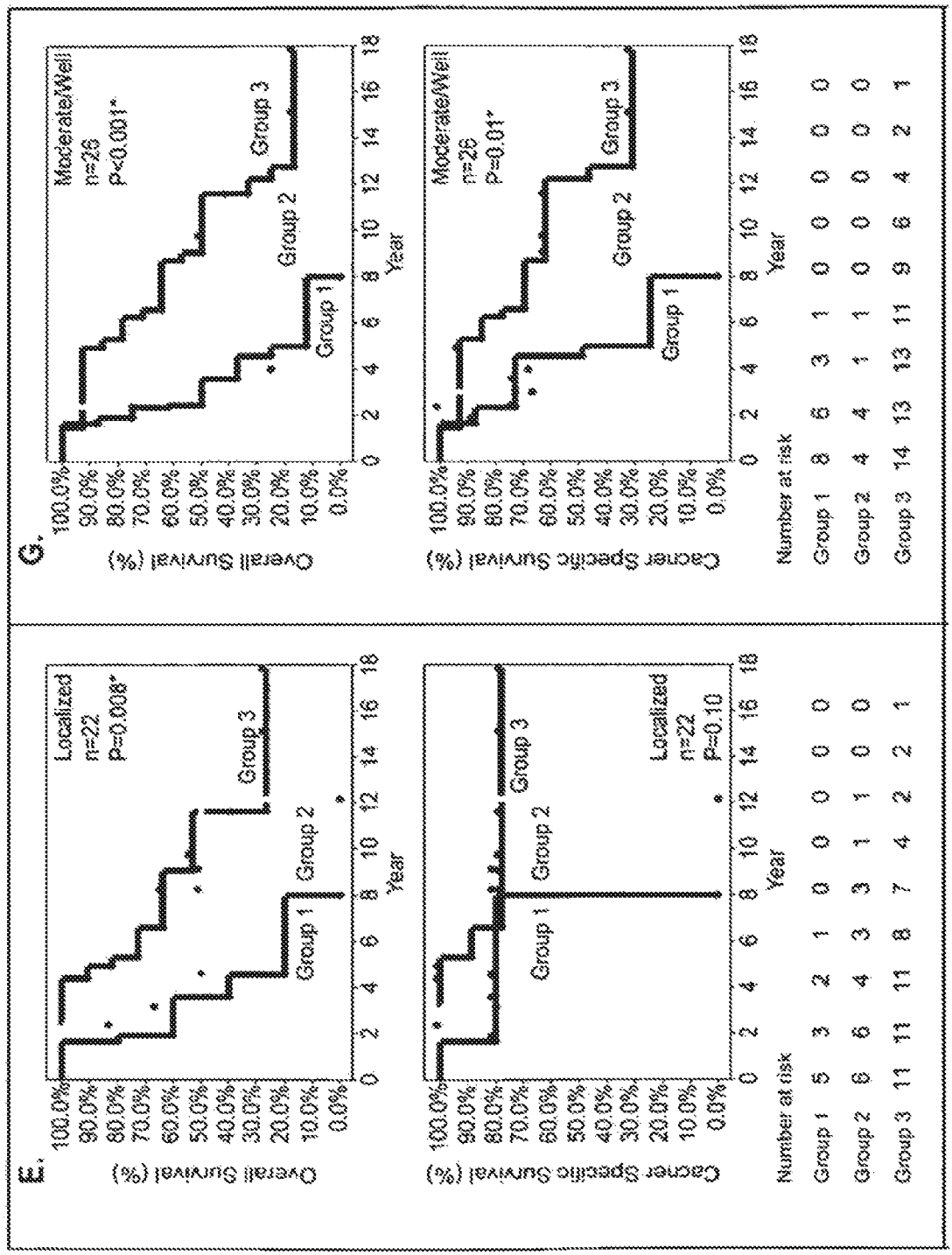
Figures 11F, 11H:
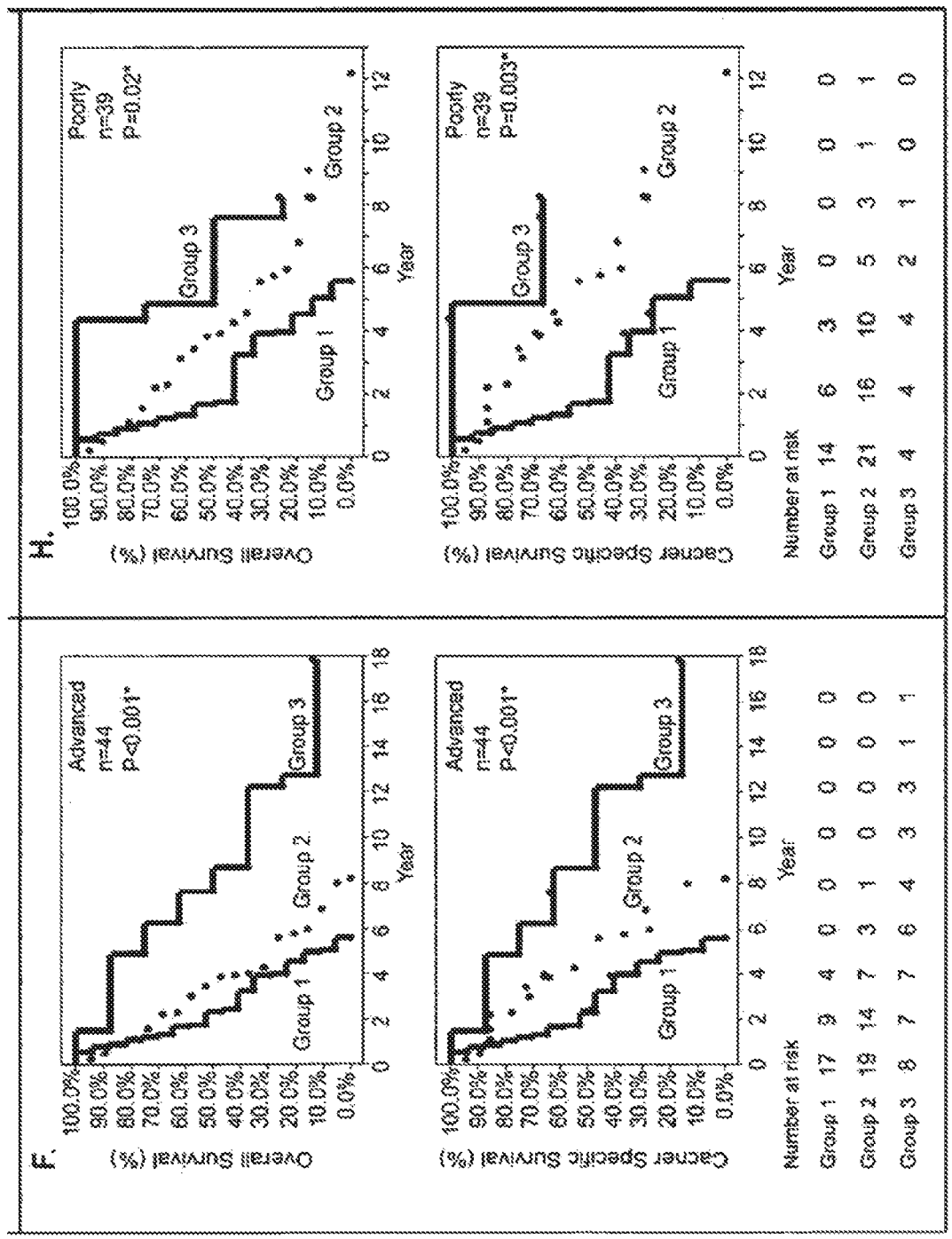

Interestingly, median survival time of unspecific deaths was 3.54 years in the high risk, 3.70 years in the intermediate risk and 7.98 years in the low risk subtype (FIG. 6E). Within 5 years after diagnosis, deaths not directly due to prostate cancer were only 4/31 cases (12.9%) in the low risk as compared to 9/31 (29%) in the high risk and 9/32 (28%) in the intermediate risk subtype respectively. Of the three cases with shortest survival time in the low risk subtype (symbolized spots), PC39 and PC140 were never treated after prostate cancer diagnosis and died of other diseases, and PC234 was diagnosed at 81 years old, treated only by castration therapy and died of prostate cancer.

Kaplan-Meier curves further presented obvious survival difference between the three subtypes classified by the tumor ESCGP Signature 1. Overall survival rate of high risk (Group 1), intermediate risk (Group 2) and low risk (Group 3) subtype was 20%, 40% and 80% at 5 years, and 10.3%, 25.0% and 64.4% at 8 years respectively (FIG. 6B).

The survival difference between the high risk and the low risk subtype was much more impressive than the results by any clinical parameters, and was still seen within each patient group or became further more obvious within the same patient group defined by PSA, clinical stage, tumor grade or age (FIG. 6C-D). For instance, 48 of the 92 patients had serum PSA≤50 ng/ml at diagnosis. Of these 48 patients, overall survival at 8 years was 21.4% for the high risk, 47.1% for the intermediate risk and 76.5% for the low risk subtype respectively. Most impressively, 40 of the 92 patients were with age≤73. Of these 40 young patients, overall survival at 8 years was 7.1% for the high risk, 44.4% for the intermediate risk and 88.2% for the low risk subtype respectively. Moreover, the survival difference between the classified groups was also seen in patient groups treated only by castration therapy (FIGS. 6-11).

Example 3C

Improved Survival Prediction by Adding the ESCGP Signature to Clinical Parameters Parametric model was used for survival prediction to estimate how much the subtype classification by the signature of VGLL3, IGFBP3 and F3 (Signature 1) could improve the prediction by using all clinical parameters (FIG. 12). Compared with the prediction model that only used clinical parameters, addition of the subtype classification by use of Signature 1 improves the accuracy of prediction for overall survival from 70.1% up to 78.2% and for cancer specific survival from 65.5% to 71.3% at 5 years (FIG. 12C). Based on Cox regression analysis, likelyhood ratio (LR) nest tests show that the subtype classification by Signature 1 significantly contributes to the improvement of regression degree in multivariate model together with clinical parameters (FIG. 12D).

Example 3D

Clear Survival Difference According to Tumor Subtype Classification Based on ESCGP Signature 3 (IGFBP3 and F3)

Figure 13:
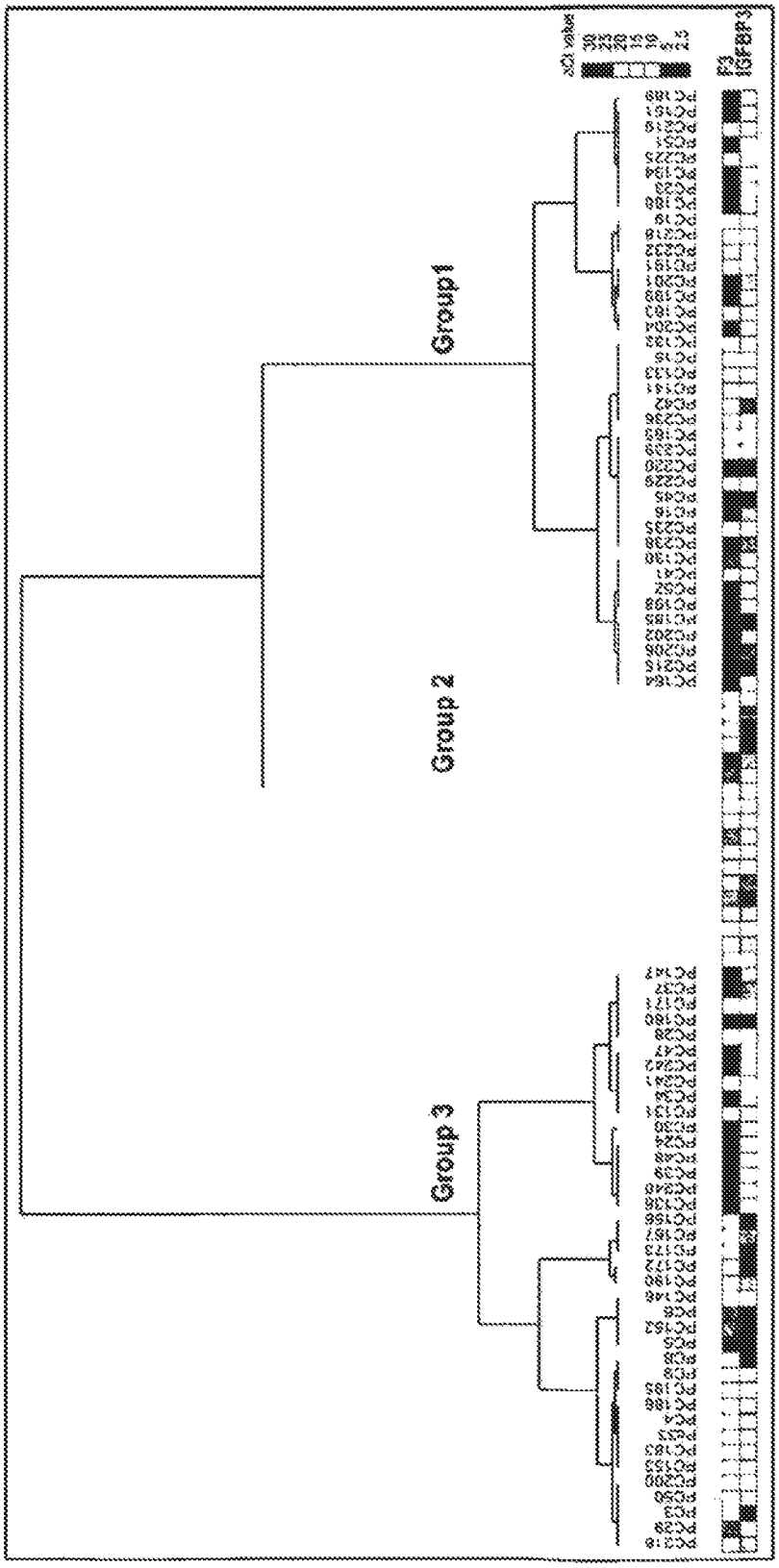
FIG. 13 illustrates tumor subtype classification of the complete set of patients by ESCGP Signature 3 (IGFBP3 and F3). Out of 189 patients, 95 had data available for the evaluation of ESCGP signature 3. Three tumor subtypes (Group 1, Group 2 and Group 3) were classified by unsupervised hierarchical clustering method using the median-centered delta Ct values of the two genes (F3 and IGFBP3) measured in the FNA samples. The results were visualized by using the Treeview software. The gene expression level is represented by a grey scale. The level of gene expression increases with decreasing ΔCt value.

Out of 189 patients, 95 had data available for the evaluation of ESCGP signature 3 (IGFBP3 and F3). Three tumor subtypes (Group 1, Group 2 and Group 3) were classified by unsupervised hierarchical clustering method using the median-centered delta Ct values of the two genes (F3 and IGFBP3) measured in the FNA samples. The results were visualized by using the Treeview software (FIG. 13). The gene expression level is represented by a grey scale. The clinical parameters of each patient are marked by various symbols as presented in the figure. As presented in Table 4-5 the three-group classification by the two gene-signature shows correlation to overall and cancer specific survival significantly stronger than any one of the two genes alone.

The invention claimed is:

1. A process comprising the steps of
providing a sample from a prostate tumor in a subject; and
measuring the level of expression in the sample of a set of genes consisting of the F3, IGFBP3, and VGLL3 genes, and optionally one of the genes WNTB5 and CTGF or both.

2. The process of claim 1, where the tumor sample is obtained by fine needle aspiration (FNA), needle biopsy, or surgery.

3. The process of claim 1, wherein the level of expression is measured by quantifying the amount of RNA or mRNA expressed from the genes.

4. The process of claim 3, wherein the amount of RNA or mRNA is determined by use of microarray technology, or by use of Northern blotting and quantitative PCR.

5. The process of claim 4, wherein the quantitative PCR is real time quantitative PCR or multiplex PCR.

6. The process of claim 1, wherein the level of expression is measured by measuring the amount of protein which is encoded by the gene(s) in the sample.

7. The process of claim 6, wherein the amount of protein is measured by immunohistochemistry, Western blotting, ELISA, RIA, or mass spectrometry.

* * * * *